(12) United States Patent
Paulson et al.

(10) Patent No.: US 8,357,671 B2
(45) Date of Patent: Jan. 22, 2013

(54) HIGH AFFINITY SIGLEC LIGANDS

(75) Inventors: James Paulson, Del Mar, CA (US);
Brian Collins, Encinitas, CA (US);
Shoufa Han, San Diego, CA (US)

(73) Assignee: James Paulson, Del Mar, CA (US)

( * ) Notice: Subject to any disclaimer, the term of this patent is extended or adjusted under 35 U.S.C. 154(b) by 844 days.

(21) Appl. No.: 12/084,723

(22) PCT Filed: Nov. 10, 2006

(86) PCT No.: PCT/US2006/043661
§ 371 (c)(1),
(2), (4) Date: May 28, 2009

(87) PCT Pub. No.: WO2007/056525
PCT Pub. Date: May 18, 2007

(65) Prior Publication Data
US 2009/0238837 A1    Sep. 24, 2009

Related U.S. Application Data

(60) Provisional application No. 60/736,039, filed on Nov. 10, 2005, provisional application No. 60/738,043, filed on Nov. 21, 2005, provisional application No. 60/832,630, filed on Jul. 21, 2006.

(51) Int. Cl.
*A01N 43/04* (2006.01)
*A61K 31/715* (2006.01)
*C13K 5/00* (2006.01)
*C13K 7/00* (2006.01)

(52) U.S. Cl. .................. 514/53; 536/123.13

(58) Field of Classification Search .......... None
See application file for complete search history.

(56) References Cited

U.S. PATENT DOCUMENTS

| | | | |
|---|---|---|---|
| 5,264,567 A * | 11/1993 | Numata et al. ................ | 536/53 |
| 5,908,766 A | 6/1999 | Yamamoto et al. | |
| 6,875,737 B1 | 4/2005 | Bachovchin | |
| 7,033,594 B2 | 4/2006 | Low et al. | |
| 2004/0185054 A1 | 9/2004 | Mullis | |
| 2005/0069549 A1 | 3/2005 | Herman | |
| 2006/0040856 A1 | 2/2006 | DeFrees et al. | |
| 2008/0139485 A1* | 6/2008 | Bochner et al. ................ | 514/25 |

FOREIGN PATENT DOCUMENTS

| WO | WO-01/74382 A1 | 10/2001 |
|---|---|---|
| WO | WO-03/028634 A2 | 4/2003 |
| WO | WO-2007/056525 A2 | 5/2007 |

OTHER PUBLICATIONS

"International Application Serial No. PCT/US06/43661, International Search Report mailed Sep. 24, 2007", 2 pgs.
"International Application Serial No. PCT/US06/43661, Written Opinion mailed Sep. 24, 2007", 6 pgs.
Bertozzi, C., et al., "C-Glycosyl compounds bind to receptors on the surface of *Escherichia coli* and can target proteins to the organism", *Carbohydrate Research*, 223,(1992), 243-253.
Blixt, O., et al., "Potent Sialoside Inhibitors of Human and Murine CD22", Poster presentation at the Society for Glycobiology Meeting, Nov. 2003, 1 pg.
Collins, B. E., et al., "High-Affinity Ligand Probes of CD22 Overcome the Threshold Set by *cis* Ligands to Allow for Binding, Endocytosis, and Killing of B Cells", *The Journal of Immunology*, 177, (2006), 2994-3003.
Collins, B. E., et al., "Masking of CD22 by cis ligands does not prevent redistribution of CD22 to sites of cell contact", *Proc. Natl. Acad. Sci. USA*, 101(16), (2004), 6104-6109.
Crocker, P. R., et al., "Siglecs and their roles in the immune system", *Nature Reviews Immunology*, 7(4), (2007), 255-266.
Crocker, P. R., et al., "Siglecs in innate immunity", *Current Opinion in Pharmacology*, 5(4), (2005), 431-437.
Crocker, P. R., "Siglecs: Sialic-Acid-Binding Immunoglobulin-Like Lectins in Cell-Cell Interactions and Signalling", *Current Opinion in Structural Biology*, 12(5), (2002), 609-615.
Furman, R. R., et al., "Epratuzumab in non-Hodgkin's lymphomas", *Current Treatment Options in Oncology*, 5(4), (2004), 283-288.
Haas, K., et al., "CD22 Ligand Binding Regulates Normal and Malignant B Lymphocyte Survival In Vivo", *The Journal of Immunology*, 177(5), (2006), 3063-3073.
Han, S., et al., "Chapter 1—Synthesis of 9-Substituted Sialic Acids As Probes for CD22-Ligand Interactions on B cells.", *In: Frontiers in Modern Carbohydrate Chemistry.*, (ACS Symposium Series 960), Demchenko, A. V., Editor, American Chemical Society, (2007), 2-14.
Kelm, S., et al., "The Ligand-binding Domain of CD22 Is Needed for Inhibition of the B Cell Receptor Signal, as Demonstrated by a Novel Human CD22-specific Inhibitor Compound", *The Journal of Experimental Medicine*, 195(9), (2002), 1207-1213.
Leonard, J. P., et al., "Epratuzumab, a Humanized Anti-CD22 Antibody, in Aggressive Non-Hodgkin's Lymphoma: phase I/II Clinical Trial Results", *Clinical Cancer Research*, 10(16), (2004), 5327-5334.
Lu, Y., et al., "Folate Receptor-Targeted Immunotherapy of Cancer: Mechanism and Therapeutic Potential", *Advanced Drug Delivery Reviews*, 56, (2004), 1161-1176.
Lu, Y., et al., "Folate receptor-targeted immunotherapy: induction of humoral and cellular immunity against hapten-decorated cancer cells", *Int. J. Cancer*, 116, (2005), 710-719.
Lu, Y., et al., "Folate Targeting to Haptens to Cancer Cell Surfaces Mediates Immunotherapy of Syngeneic Murine Tumors", *Cancer Immunology and Immunotherapy*, 51(3), (2002), 153-162.
Razi, N., et al., "Masking and unmasking of the sialic acid-binding lectin activity of CD22 (Siglec-2) on B lymphocytes", *Proc Natl Acad Sci USA*, 95, (1998), 7469-7474.
Shokat, K. M., et al., "Redirecting the Immune Response: Ligand-Mediated Immunogenicity", *J. Am. Chem. Soc..* 113, (1991), 1861-1862.

(Continued)

*Primary Examiner* — Traviss C McIntosh, III
(74) *Attorney, Agent, or Firm* — Schwegman Lundberg & Woessner, P.A.

(57) ABSTRACT

The invention relates to high affinity Siglec ligands that are useful for isolating cells that express Siglecs and for delivering agents to cells that express Siglecs. In one embodiment, the invention provides a method for treating cancer in a mammal that involves administering a Siglec ligand of the invention to the mammal, where the Siglec ligand is linked to a therapeutic agent.

52 Claims, 27 Drawing Sheets

OTHER PUBLICATIONS

Steinfeld, S., et al., "Epratuzumab (humanised anti-CD22 antibody) in primary Sjögren's syndrdome: an open-label phase I/II study", *Arthritis Research & Therapy*, 8(4): R129, [online]. Retrieved from Internet: <URL:http://www.biomedcentral.com/content/pdf/ar2018.pdf>, (2006), 11 pgs.

Tateno, H., et al., "Distinct Endocytic Mechanisms of CD22 (Siglec-2) and Siglec-F Reflect Roles in Cell Signaling and Innate Immunity", *Molecular and Cellular Biology*, 27(16), (2007), 5699-5710.

Zaccai, N. R., et al., "Structure-Guided Design of Sialic Acid-Based Siglec Inhibitors and Crystallographic Analysis in Complex with Sialoadhesin", *Structure*, 11(5), (2003), 557-567.

"European Application Serial No. 06844306.8, Response filed Nov. 17, 2011 to Office Action mailed Jul. 8, 2011", 46 pgs.

"European Application Serial No. 06844306.8 Office Action mailed Feb. 19, 2010", 1 pg.

Chen, W. C., et al., "In vivo targeting on B-cell lymphoma with glycan ligands of CD22", *Blood*, 115(23), (2010), 4778-4786.

Hashimoto, Y., et al., "A Streptavidin-Based Neoglycoprotein Carrying More Than 140 GT1b Oligosaccharides: Quantitative Estimation of the Binding Specificity of Murine Sialoadhesin Expressed on CHO Cells", *J. Biochem.* 123, (1998), 468-478.

Nakamura, K., et al., "Lymph node macrophages, but not spleen macrophages, express high levels of unmasked sialoadhesin: implication for the adhesive properties of macrophages in vivo", *Glycobiology*, 12(3), (2002), 209-216.

Sackstein, R., "Hitting the sweet spot for lymphoma", *Blood*, 115(23), (2010), 4626-4627.

"U.S. Appl. No. 12/084,723, Restriction Requirement mailed Jun. 28, 2011", 6 pgs.

"European Application Serial No. 06844306.8, Office Action mailed Jul. 8, 2011", 4 pgs.

Han, Shoufa, et al., "Homomultimeric Complexes of CD22 in B Cells Revelated by Protein-Glycan Cross-Linking", Nature Chemical Biology, doi:10.1038/nchembio713, (2005), 1-5.

"European Application Serial No. 06844306.8, Response filed Aug. 27, 2010 to Office Action mailed Feb. 19, 2010", 21 pgs.

"Ring opening metathesis polymerisation", [online]. [retrieved Aug. 20, 2010]. Retrieved from the Internet: <URL: http://en.wikipedia.org/wiki/Ring_opening_metathesis_polymerisation, 4 pgs.

"European Application Serial No. 06844306.8, Extended European Search Report Mailed Sep. 17, 2009", 4 pgs.

Blixt, O., et al., "Sialoside Specificity of the Siglec Family Assessed Using Novel Multivalent Probes", *The Journal of Biological Chemistry*, 278(33), (2003), 31007-31019.

\* cited by examiner

SEQUENCE LISTING

```
<160> NUMBER OF SEQ ID NOS: 1

<210> SEQ ID NO 1
<211> LENGTH: 847
<212> TYPE: PRT
<213> ORGANISM: Homo sapiens

<400> SEQUENCE: 1
```

| Met | His | Leu | Leu | Gly | Pro | Trp | Leu | Leu | Leu | Val | Leu | Glu | Tyr | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ala | Phe | Ser | Asp | Ser | Ser | Lys | Trp | Val | Phe | Glu | His | Pro | Glu | Thr | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Ala | Trp | Glu | Gly | Ala | Cys | Val | Trp | Ile | Pro | Cys | Thr | Tyr | Arg | Ala |
|     |     |     | 35  |     |     |     | 40  |     |     |     |     | 45  |     |     |     |

| Leu | Asp | Gly | Asp | Leu | Glu | Ser | Phe | Ile | Leu | Phe | His | Asn | Pro | Glu | Tyr |
|     | 50  |     |     |     |     | 55  |     |     |     |     | 60  |     |     |     |     |

| Asn | Lys | Asn | Thr | Ser | Lys | Phe | Asp | Gly | Thr | Arg | Leu | Tyr | Glu | Ser | Thr |
| 65  |     |     |     |     | 70  |     |     |     |     | 75  |     |     |     |     | 80  |

| Lys | Asp | Gly | Lys | Val | Pro | Ser | Glu | Gln | Lys | Arg | Val | Gln | Phe | Leu | Gly |
|     |     |     |     | 85  |     |     |     |     | 90  |     |     |     |     | 95  |     |

| Asp | Lys | Asn | Lys | Asn | Cys | Thr | Leu | Ser | Ile | His | Pro | Val | His | Leu | Asn |
|     |     |     |     | 100 |     |     |     |     | 105 |     |     |     |     | 110 |     |

| Asp | Ser | Gly | Gln | Leu | Gly | Leu | Arg | Met | Glu | Ser | Lys | Thr | Glu | Lys | Trp |
|     |     |     | 115 |     |     |     |     | 120 |     |     |     |     | 125 |     |     |

| Met | Glu | Arg | Ile | His | Leu | Asn | Val | Ser | Glu | Arg | Pro | Phe | Pro | Pro | His |
|     | 130 |     |     |     |     | 135 |     |     |     |     | 140 |     |     |     |     |

| Ile | Gln | Leu | Pro | Pro | Glu | Ile | Gln | Glu | Ser | Gln | Glu | Val | Thr | Leu | Thr |
| 145 |     |     |     |     | 150 |     |     |     |     | 155 |     |     |     |     | 160 |

| Cys | Leu | Leu | Asn | Phe | Ser | Cys | Tyr | Gly | Tyr | Pro | Ile | Gln | Leu | Gln | Trp |
|     |     |     |     | 165 |     |     |     |     | 170 |     |     |     |     | 175 |     |

| Leu | Leu | Glu | Gly | Val | Pro | Met | Arg | Gln | Ala | Ala | Val | Thr | Ser | Thr | Ser |
|     |     |     | 180 |     |     |     |     | 185 |     |     |     |     | 190 |     |     |

| Leu | Thr | Ile | Lys | Ser | Val | Phe | Thr | Arg | Ser | Glu | Leu | Lys | Phe | Ser | Pro |
|     |     | 195 |     |     |     |     | 200 |     |     |     |     | 205 |     |     |     |

| Gln | Trp | Ser | His | His | Gly | Lys | Ile | Val | Thr | Cys | Gln | Leu | Gln | Asp | Ala |
|     | 210 |     |     |     |     | 215 |     |     |     |     | 220 |     |     |     |     |

| Asp | Gly | Lys | Phe | Leu | Ser | Asn | Asp | Thr | Val | Gln | Leu | Asn | Val | Lys | His |
| 225 |     |     |     |     | 230 |     |     |     |     | 235 |     |     |     |     | 240 |

| Thr | Pro | Lys | Leu | Glu | Ile | Lys | Val | Thr | Pro | Ser | Asp | Ala | Ile | Val | Arg |
|     |     |     |     | 245 |     |     |     |     | 250 |     |     |     |     | 255 |     |

| Glu | Gly | Asp | Ser | Val | Thr | Met | Thr | Cys | Glu | Val | Ser | Ser | Ser | Asn | Pro |
|     |     |     | 260 |     |     |     |     | 265 |     |     |     |     | 270 |     |     |

| Glu | Tyr | Thr | Thr | Val | Ser | Trp | Leu | Lys | Asp | Gly | Thr | Ser | Leu | Lys | Lys |
|     |     |     | 275 |     |     |     |     | 280 |     |     |     |     | 285 |     |     |

| Gln | Asn | Thr | Phe | Thr | Leu | Asn | Leu | Arg | Glu | Val | Thr | Lys | Asp | Gln | Ser |
|     |     | 290 |     |     |     |     | 295 |     |     |     |     | 300 |     |     |     |

| Gly | Lys | Tyr | Cys | Cys | Gln | Val | Ser | Asn | Asp | Val | Gly | Pro | Gly | Arg | Ser |
| 305 |     |     |     |     | 310 |     |     |     |     | 315 |     |     |     |     | 320 |

| Glu | Glu | Val | Phe | Leu | Gln | Val | Gln | Tyr | Ala | Pro | Glu | Pro | Ser | Thr | Val |
|     |     |     |     | 325 |     |     |     |     | 330 |     |     |     |     | 335 |     |

| Gln | Ile | Leu | His | Ser | Pro | Ala | Val | Glu | Gly | Ser | Gln | Val | Glu | Phe | Leu |
|     |     |     |     | 340 |     |     |     |     | 345 |     |     |     |     | 350 |     |

```
Cys Met Ser Leu Ala Asn Pro Leu Pro Thr Asn Tyr Thr Trp Tyr His
        355                 360                 365

Asn Gly Lys Glu Met Gln Gly Arg Thr Glu Glu Lys Val His Ile Pro
        370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
        435                 440                 445

Pro Ser Val Thr Arg Tyr Glu Trp Lys Pro His Gly Ala Trp Glu Glu
    450                 455                 460

Pro Ser Leu Gly Val Leu Lys Ile Gln Asn Val Gly Trp Asp Asn Thr
465                 470                 475                 480

Thr Ile Ala Cys Ala Arg Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
        515                 520                 525

Cys Asp Phe Ser Ser Ser His Pro Lys Glu Val Gln Phe Phe Trp Glu
    530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
            580                 585                 590

Pro Arg Arg Leu Arg Val Ser Met Ser Pro Gly Asp Gln Val Met Glu
        595                 600                 605

Gly Lys Ser Ala Thr Leu Thr Cys Glu Ser Asp Ala Asn Pro Pro Val
    610                 615                 620

Ser His Tyr Thr Trp Phe Asp Trp Asn Asn Gln Ser Leu Pro His His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
        675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
        755                 760                 765

Glu Met Asn Ile Pro Arg Thr Gly Asp Ala Glu Ser Ser Glu Met Gln
```

```
                770                 775                 780
Arg Pro Pro Arg Thr Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
                820                 825                 830

Arg Pro Gln Ala Gln Glu Asn Val Asp Tyr Val Ile Leu Lys His
                835                 840                 845
```

HIGH AFFINITY SIGLEC LIGANDS

RELATED APPLICATIONS

This application is a U.S. National Stage filing under 35 U.S.C. from International Application No. PCT/2006/043661 filed Nov. 10, 2006 and published as WO 2007/056525 A2/A3 on May 18, 2007, which claims benefit of the filing date of U.S. Provisional Application Ser. No. 60/736,039, filed Nov. 10, 2005, U.S. Provisional Application Ser. No. 60/738043, filed Nov. 21, 2005, and U.S. Provisional Application Ser. No. 60/832,630, filed Jul. 21, 2006, the contents of each of which publication and applications are incorporated herein by reference in their entireties.

GOVERNMENT FUNDING

The invention described herein was made with United States Government support under Grant Numbers GM060938 and AI050143 awarded by the National Institutes of Health. The United States Government has certain rights in this invention.

FIELD OF THE INVENTION

The invention relates to ligands for Siglecs that effectively bind to cells that express Siglecs. In some embodiments, the Siglec is CD22, which is expressed on B cells, or Siglec-8 (related to mouse Siglec-F) which, is expressed on human eosinophils. As illustrated herein, the Siglec ligands can be linked or bound to therapeutic agents and, upon administration, the ligand-bound therapeutic agent can be delivered into a cell. Also, as shown herein, the ligands can be linked or bound to molecules that lead to cell destruction, for example, to toxins or to antigens recognized by antibodies. Therefore, the Siglec ligands of the invention can be used as delivery agents useful for treating diseases, including B cell-related cancers (e.g. leukemia) and eosinophil-related diseases (e.g. asthma).

BACKGROUND OF THE INVENTION

B-Cell lymphomas, such as the B-cell subtype of non-Hodgkin's lymphoma, are significant contributors to cancer mortality. The response of B-cell malignancies to various forms of treatment is mixed. For example, in cases in which adequate clinical staging of non-Hodgkin's lymphoma is possible, field radiation therapy can provide satisfactory treatment. Still, about one-half of the patients die from the disease. Devesa et al., J. Nat'l Cancer Inst. 79:701 (1987).

The majority of chronic lymphocytic leukemias are of B-cell lineage. Freedman, Hematol. Oncol. Clin. North Am. 4:405 (1990). This type of B-cell malignancy is the most common leukemia in the Western world. Goodman et al., Leukemia and Lymphoma 22:1 (1996). The natural history of chronic lymphocytic leukemia falls into several phases. In the early phase, chronic lymphocytic leukemia is an indolent disease, characterized by the accumulation of small mature functionally-incompetent malignant B-cells having a lengthened life span. Eventually, the doubling time of the malignant B-cells decreases and patients become increasingly symptomatic.

While treatment can provide symptomatic relief, the overall survival of the patients is only minimally affected. The late stages of chronic lymphocytic leukemia are characterized by significant anemia and/or thrombocytopenia. At this point, the median survival is less than two years. Foon et al., Annals Int. Medicine 113:525 (1990). Due to the very low rate of cellular proliferation, chronic lymphocytic leukemia is resistant to treatment. Traditional methods of treating B-cell malignancies, including chemotherapy and radiotherapy, have limited utility due to toxic side effects. Using an antibody that binds to a surface component on the B cell is an alternate approach of directing an immune response to cancer cells. The use of monoclonal antibodies to direct radionuclides, toxins, or other therapeutic agents also offers the possibility that such agents can be delivered selectively to tumor sites, thus limiting toxicity to normal tissues. However, antibodies are typically not taken up by cells. Thus, even when an antibody is linked to a toxin, the toxin may only be delivered to the surface of a cell.

A need therefore exists for new agents that can bind to and be internalized within Siglec-expressing cells, including malignant B-cells.

The accumulation of eosinophil leukocytes is a characteristic feature of IgE-mediated allergic reactions such as allergic asthma, rhinitis and eczema. Eosinophil accumulation also occurs in non-allergic asthma. The immediate bronchoconstriction in response to a provoking stimulus in the asthmatic involves mast cell activation and the release of constrictor mediators. This is followed after several hours in some individuals by a late bronchoconstrictor response associated with a massive influx of eosinophils. Repeated provocation results in chronic inflammation in the airways and a marked hyper-responsiveness to constrictor mediators. The magnitude of both the late response and the chronic hyper-responsiveness correlates with the numbers of eosinophils present in the lung.

The global prevalence of asthma continues to increase, affecting millions of peoples' daily lives, but treatment is far from ideal. Clinical responses to current therapies, such as inhaled corticosteroids and leukotriene modifiers are heterogeneous and even with optimal treatment there is a substantial burden of unaddressed disease. Therefore, a need also exists for agents that can control eosinophil-related diseases such as asthma.

SUMMARY OF THE INVENTION

The invention relates to high affinity Siglec ligands that can be used to detect, and deliver agents to, cells that express Siglecs. Because distinct Siglecs are expressed on different cell types, these different cell types can be targeted for therapy by selecting a Siglec ligand that specifically binds to the specific type of Siglec expressed on a selected cell type. Thus, different cell-type specific diseases and conditions can be treated by administration of a Siglec-specific ligand that can deliver a therapeutic agent to a Siglec expressed on a specific cell type.

One aspect of the invention is a Siglec ligand compound of formula Ia, Ib, Ic or Id:

  Ia

  Ib

  Ic

  Id wherein:

$R_5$ and $R_9$ are independently each a hydrogen, hydroxyl, acetylamine, alkyl, alkylamide, cycloalkyl, heteroalkyl, cycloheteroalkyl, aryl, arylalkyl, arylamide or heteroaryl group that can be substituted with one to five alkyl, halo, sulfate or hydroxy groups;

Sia is a sialic acid;

Sac is a neutral saccharide;

Y is a covalent bond to Carrier, a linker that can be attached to Carrier or an antigen that can bind to an antibody Carrier;

the symbol ~ is a non-covalent bond;

n is an integer of from 5 to 500; and

Carrier is a polymer, protein, antibody, antigen, multi-subunit protein, protein complex, glycan or solid support; and wherein at least one of $R_5$ or $R_9$ is an alkyl, alkylamide, cycloalkyl, heteroalkyl, cycloheteroalkyl, aryl, arylalkyl, arylamide or heteroaryl group that can be substituted with one to five alkyl, halo, or sulfate groups.

The compounds of formula Ia, Ib, Ic or Id can be covalently attached to the carrier either directly or indirectly through a linker. Covalent attachment is represented by a straight line or hyphen leading to the carrier. Alternatively, these compounds can bind to the carrier through non-covalent (~) interactions, which are represented by a wavy line (~). For example, Y can be an antigen (e.g. nitrophenyl) that can be recognized and bound by an antibody that acts as a carrier (e.g. an IgM antibody that can bind up to ten antigen-Siglec ligands). Such non-covalent antigen-antibody interactions can occur in vitro or in vivo.

In some embodiments, the sialic acid is N-acetylneuraminic acid (Neu5Ac) or N-glycolylneuraminic acid (Neu5Gc). Another aspect of the invention is a compound of formula IIa:

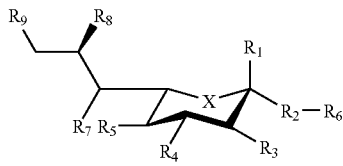

wherein:

X is a methylene or a heteroatom;

$R_1$ is a carboxylate, carboxy, phosphate or sulfate;

$R_2$ is a neutral saccharide;

$R_3$, $R_4$, $R_7$ and $R_8$ are each independently a hydrogen, a hydroxyl or an acetylamine;

$R_5$ is a hydrogen, hydroxyl, acetylamine, alkyl, alkylamide, cycloalkyl, heteroalkyl, cycloheteroalkyl, aryl, arylalkyl, arylamide or heteroaryl group that can be substituted with one to five alkyl, halo, or sulfate group;

$R_6$ is hydrogen, a Y group, an alkyl, or a carrier;

$R_9$ is a hydrogen, hydroxyl, acetylamine, alkyl, alkylamide, cycloalkyl, heteroalkyl, cycloheteroalkyl, aryl, arylalkyl, arylamide or heteroaryl group that can be substituted with one to five alkyl, halo, sulfate or hydroxy groups; and wherein at least one of $R_5$ or $R_9$ is an alkyl, alkylamide, cycloalkyl, heteroalkyl, cycloheteroalkyl, aryl, arylalkyl, arylamide or heteroaryl group that can be substituted with one to five alkyl, halo, or sulfate group.

Another aspect of the invention is a compound of formula IIb:

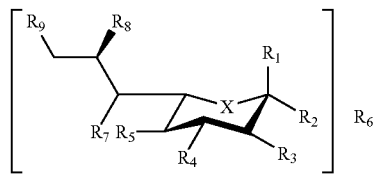

wherein: X, $R_1$, $R_2$, $R_3$, $R_4$, $R_5$, $R_7$, $R_8$ and $R_9$ are as defined above; and $R_6$ is a carrier.

Compounds of formulae Ia, Ib, IIa and IIb are Siglec ligands. In some embodiments, the $R_2$ and $R_6$ substituents of formulae IIa and/or IIb are joined by a linker. In other embodiments, the $R_2$ and $R_6$ substituents of formulae IIa and/or IIb are joined by a covalent bond. In further embodiments, $R_6$ is a carrier that is non-covalently associated with at least a portion of the Siglec ligand, where such a non-covalent association is depicted by a ~ symbol or by brackets ([ ]).

In some embodiments, the neutral saccharide of formulae Ia, Ib, IIa and/or IIb is of formula IIIa:

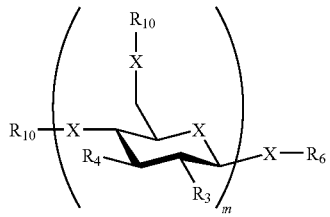

wherein:

X is methylene or a heteroatom (for example, O, N, or S);

$R_3$ and $R_4$ are each independently a hydrogen, a hydroxyl or a acetylamine;

$R_6$ is hydrogen, a Y group, an alkyl, or a carrier;

m is an integer of from 1 to 10; and each $R_{10}$ is sugar residue, a saccharide, [$R_5$-Sia] or [$R_9$-Sia], wherein $R_5$ and $R_9$ are as defined herein; and Sia is a sialic acid.

In other embodiments, the neutral saccharide has formula IIIb:

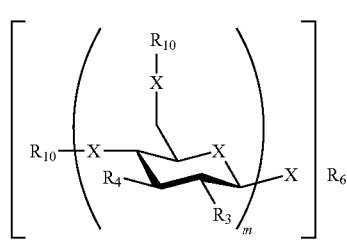

wherein: X, $R_3$, $R_4$, and $R_{10}$ are as defined above; and $R_6$ is a non-covalently associated carrier.

Another aspect of the invention is a compound of the following formula:

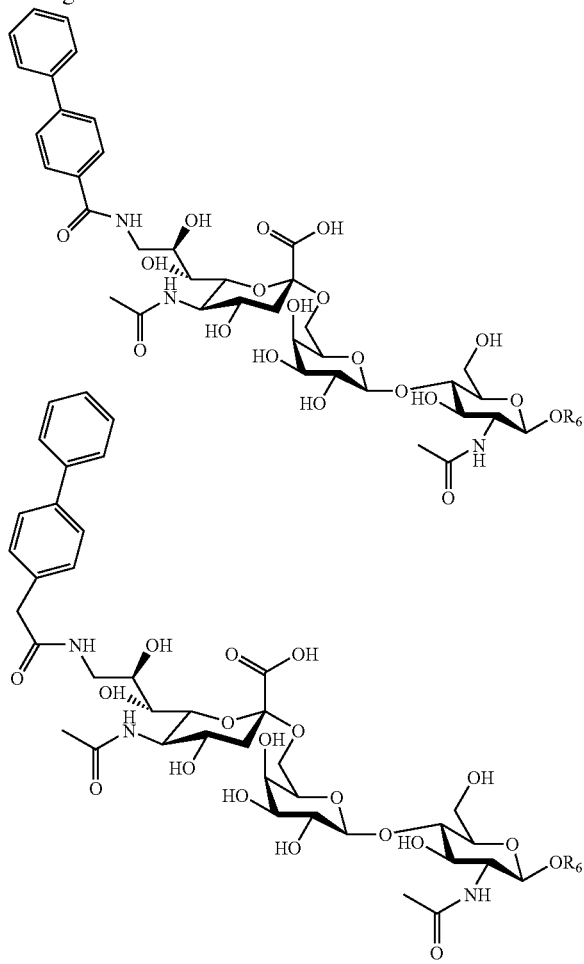

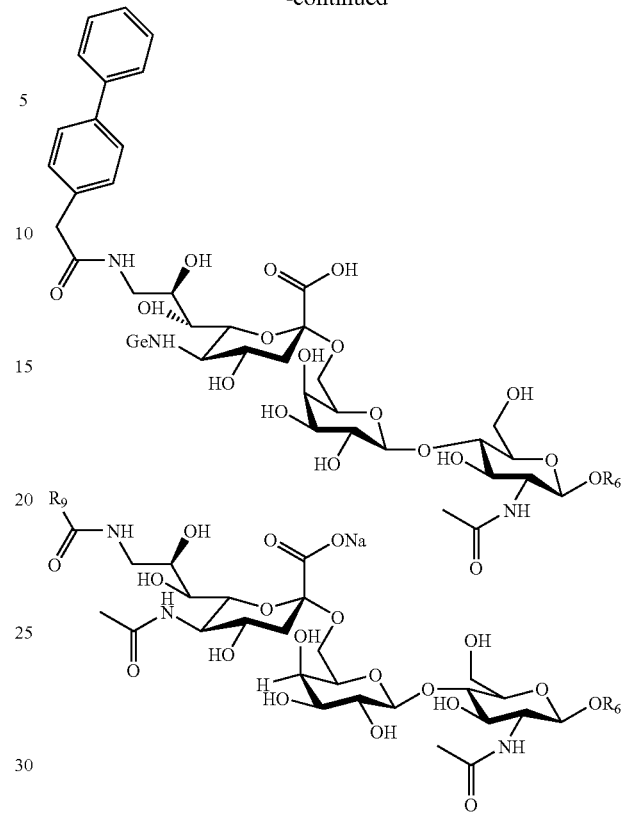

wherein $R_6$ is hydrogen, a Y group, an alkyl, or a carrier; and $R_9$ is an alkyl, alkylamide, cycloalkyl, heteroalkyl, cycloheteroalkyl, aryl, arylalkyl, arylamide or heteroaryl group that can be substituted with one to five alkyl, halo, sulfate or hydroxy groups.

Another aspect of the invention is a Siglec ligand compound of the following formula:

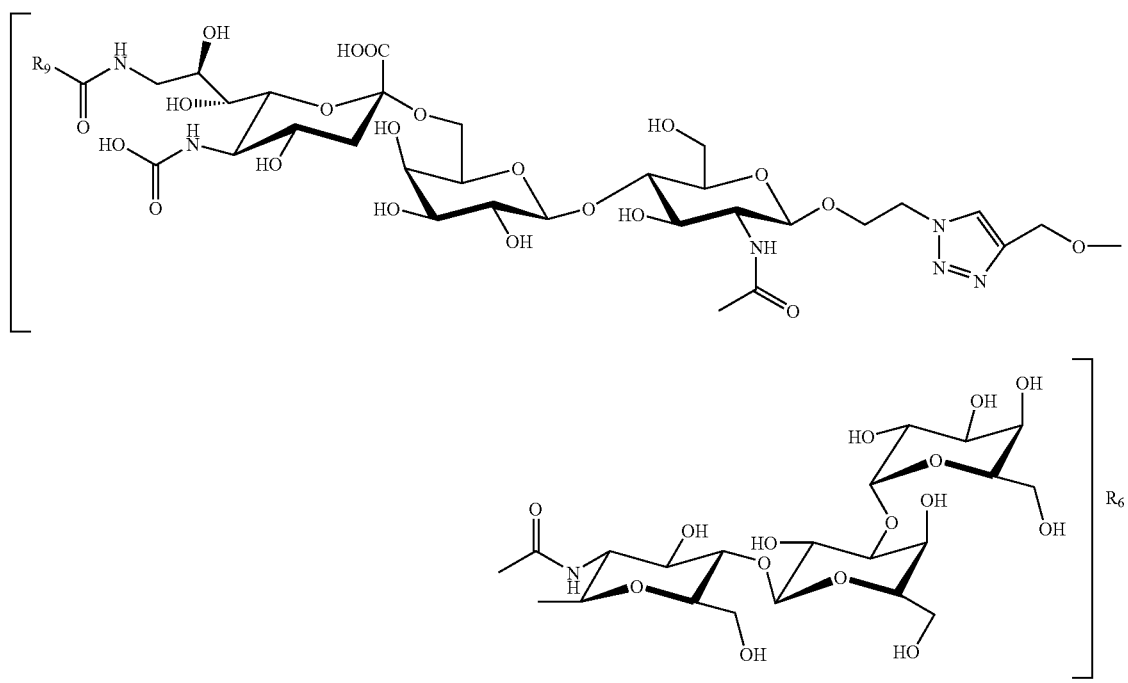

Wherein $R_9$ is as defined herein and $R_6$ is a non-covalently bound carrier.

Another aspect of the invention is a multivalent carrier to which 5 to 500 Siglec ligands are covalently attached or non-covalently bound. The Siglec ligands can share the same $R_6$ carrier, for example, by covalent attachment or binding to different sites on the carrier.

Another aspect of the invention is a multivalent carrier to which 5 to 500 Siglec ligands are attached (covalently or non-covalently), where the Siglec ligands include the moiety [$R_9$-Sia-Sac] or [$R_5$-Sia-Sac]. In some embodiments, the multi-subunit carrier is an antibody, for example, an IgM antibody that can bind several Siglec ligands. When the carrier is an antibody it can bind to an antigen attached to the Siglec ligand. In other embodiments, the multi-subunit carrier is an antigen or a serum amyloid protein carrier.

Another aspect of the invention is an article that includes a solid support and a compound of the invention. Examples of solid supports that can be used in the articles of the invention include magnetic beads and chromatographic matrices.

Another aspect of the invention is a method of isolating a cell that expresses a Siglec that involves: (a) contacting a mixture of cells that may express a Siglec with an article of invention (that is attached to a Siglec ligand of the invention); (b) washing the article; and (c) eluting cells from the article. While the inventive methods can be practiced with any of the present Siglec ligands and using any source of Siglec-expressing cells, in some embodiments, the Siglec is CD22, CD33, Siglec-8 or myelin associated glycoprotein (MAG; Siglec-4).

Another aspect of the invention is a composition comprising a pharmaceutically acceptable carrier and a therapeutically effective amount of a compound of the invention.

Another aspect of the invention is a method for intracellular delivery of an agent comprising contacting the cell with a compound of the invention, wherein the cell expresses a Siglec and the compound is linked to the agent. While the Siglec can be any Siglec, in some embodiments, the Siglec is CD22. In other embodiments, the Siglec is CD33, Siglec-8 or myelin associated glycoprotein (MAG; Siglec-4). For example, a therapeutic agent can be incorporated into a carrier such as a liposome, or the agent can be covalently or non-covalently attached to a carrier such as a polymer, a multi-subunit protein (e.g., IgM or serum amyloid protein) or an antigen. These liposomes, multi-subunit proteins, polymers or antigens can then be linked to a Siglec compound of the invention. When the cell is contacted with the Siglec ligand-carrier-therapeutic agent, the therapeutic agent is bound by and internalized into the cell.

Another aspect of the invention is a method of treating cancer in a mammal comprising administering to the mammal an effective amount of a compound of the invention that is linked or joined to an anti-tumor agent. The cancer involves cancer cells that express a Siglec. While the Siglec can be any Siglec, in some embodiments, the Siglec is CD22. In some embodiments, the cancer is a lymphoma or leukemia. For example, a therapeutic agent can be incorporated into a carrier such as a liposome, or the agent can be attached to a carrier such as a polymer, a multi-subunit protein (e.g., IgM or serum amyloid protein) or an antigen. These liposomes, multi-subunit proteins, polymers or antigens can then be linked to a Siglec compound of the invention. When the Siglec ligand-carrier-therapeutic agent is administered to the mammal, the Siglec ligand will bind to cancer cells that express Siglecs and the therapeutic agent will be internalized into the cell. For example, the anti-tumor agent can be attached to a carrier or incorporated into a liposome to which the Siglec ligand compounds of the invention are attached. Alternatively, the anti-tumor agent can be attached to a polymer or dendrimer carrier to which the Siglec ligand compound is attached. In another embodiment, the Siglec ligand can be attached to an antigen that is recognized by the mammal's immune system. When the Siglec ligand binds to the cancer cell, the associated antibody can activate complement, which leads to lysis of the cancer cell.

Another aspect of the invention is a method of treating cancer in a mammal comprising administering to the mammal an effective amount of a Siglec ligand linked to an antibody, wherein a Siglec on a cancer cell recognizes and binds to the Siglec ligand. The antibody in turn, activates the immune system (e.g., complement, opsonization of the antibody-Siglec expressing cell complex, antibody-dependent cell-mediated cytotoxicity of natural killer lymphocytes, etc.) which leads to lysis of the cancer cell(s). In some embodiments, the cancer is a lymphoma or leukemia. For example, the antibody can be an IgM antibody that acts as a carrier to which the Siglec ligand compounds of the invention are attached.

Another aspect of the invention is a method of treating an eosinophil-related disease or condition in a mammal comprising administering to the mammal an effective amount of a Siglec ligand covalently or non-covalently linked to a therapeutic agent, wherein a Siglec on an eosinophil cell recognizes and binds to the Siglec ligand. Upon delivery to the eosinophil, the therapeutic agent can modulate or inhibit the activity of the eosinophil. For example, if the therapeutic agent is an antibody, the antibody can induce apoptosis or complement, thereby leading to eosinophil cell death. In some embodiments, the disease or condition is asthma, rhinitis or eczema. For example, the antibody can be an IgG or IgM antibody. Thus, an antibody, or antigen-antibody complex can act as a carrier for the Siglec ligand compounds of the invention.

DESCRIPTION OF THE FIGURES

FIG. 1A shows the structures of some of the compounds tested and analyzed herein. FIG. 1B graphically illustrates competitive inhibition of selected sialoside inhibitors. Inhibitors were added with soluble CD22-Fc chimeras to block the chimera binding to immobilized NeuAcα2-6Galβ1-4GlcNAc (NeuAc-LN, human CD22, hCD22) or NeuGcα2,6Galβ1-4GlcNAc (NeuGc-LN, mouse CD22, mCD22). Data are the average +/−S.D. of triplicate determinations and are representative of two individual assays.

FIG. 2A provides the results for murine splenocytes. Murine splenocytes were mock-treated (grey shaded peak) or actually treated with *A. ureafaciens* sialidase to cleave sialic acid-containing glycans from cell surfaces and thereby 'unmask' surface CD22. The cells were then incubated with NeuGc-LN-PAA alone (rightmost Black line, where PAA refers to a polyacrylamide carrier) or in the presence of 5 uM (light line to the right of center), 200 uM (central grey line) or 2 mM (leftmost dark grey line) of the indicated inhibitor for 1.5 h on ice, then washed. Bound probe was detected with streptavidin-PE, and B cells stained with anti-B220. Data are for B220+ cells only. FIG. 2B provides results for Daudi Cells. Daudi cells were mock-treated (grey shaded peak) or actually treated with *A. ureafaciens* sialidase. Cells were then incubated with NeuAc-LN-PAA in the presence of 0 (rightmost black line), 10 uM (disperse small central grey peak), 30 uM (tall central grey peak), 200 uM (leftmost tall grey peak) of the indicated sialoside ligand. Bound probe was detected with streptavidin-PE and measured by flow cytometry.

FIG. 3A graphically illustrates that high molecular weight (HMW) NeuGc-LN-PAA strongly binds to CD22, whereas low molecular weight (LMW) NeuGc-LN-PAA does not. In this experiment, mouse CD22-Fc chimera was immobilized onto protein A coated microtiter plates and overlayered with the indicated amounts of the PAA probe. After washing bound probe was detected with alkaline-phosphatase labeled streptavidin and developed with pNPP measured at OD 405. Data are the average +/−triplicate determinants and are representative of three experiments. FIG. 3B further illustrates that high molecular weight NeuGc-LN-PAA strongly binds to CD22. Murine splenocytes were mock-treated (shaded peak) or actually treated with 50 mU (thin lines) or 200 mU (thick lines) *A. ureafaceins* sialidase to 'unmask' CD22, washed and then incubated on ice with low molecular weight (LMW) or high molecular weight (HMW) NeuGc-LN-PAA probes for 1.5 h. After washing the cells, cell-bound probe was detected with PE-labeled streptavidin and B cells detected with anti-B220. Data are of B220+ cells only. FIG. 3C graphically illustrates that high molecular weight biphenyl-derivatized NeuGc-LN-PAA strongly binds to mouse CD22 (siglec-2) immobilized onto protein A coated microtiter plates and overlayered with the indicated amounts of the PAA probes. After washing, bound probe was detected with Alkaline-phosphatase labeled streptavidin and developed with pNPP measured at OD 405. Data are the average +/−triplicate determinants. FIG. 3D illustrates that high molecular weight (HMW) biphenyl-derivatized NeuGc-LN-PAA strongly competes for CD22 on B cells even when the cells are not treated with sialidase to strip sialic acid-containing glycans from the surface of the cells. CD22 null (shaded) or wild type splenocytes (thick and thin lines) were mock (thick lines) or *A. ureafaciens* sialidase treated (thin lines and shaded) to 'unmask' CD22 and incubated on ice with the indicated probe for 1.5 h. After washing the splenocytes, bound probe was detected with PE-labeled streptavidin and B cells were detected with anti-B220. Data are of B220+ cells only. Similarly, FIG. 3E illustrates that high molecular weight biphenyl-derivatized NeuAc-LN-PAA strongly competes for CD22 on human B cells even when the cells are not treated with sialidase to strip sialic acid containing glycans from the surface of the cells. BJAB cells were mock (thick or shaded) or *A. ureafaciens* sialidase treated (dotted) to 'unmask' CD22 and then incubated on ice with the indicated probe (control =LN-PAA probe) for 1.5 h. After washing the splenocytes, bound probe was detected with PE-labeled streptavidin FIG. 4C graphically illustrates that greater than 40% recovery of CD22+ cells was achieved with 95% cell purity.

FIG. 7A shows a heterobifunctional ligand of CD22 ligand (BPC-NeuAcα-2, 6LacNAc, referred to as "BPC") attached to nitrophenyl ("NP"). FIG. 7B shows self-assembly of the heterobifunctional ligand (NP-BPC) with the decavalent IgM anti-NP antibody molecule, which can bind to CD22 in ELISA-type assays and on B cells. FIG. 7C shows IgM/NP-BPC/CD22 complex formation as a function of NP or NP-BPC concentration. CD22-Fc chimeras were immobilized onto protein A coated wells. After washing, the indicated amount of either NP, or NP-BPC was added along with the anti-NP IgM was added and allowed to bind for 30 min at room temperature. After washing, bound IgM was detected with HRP-conjugated anti-IgM and developed with OPD. Data are the average ±S.D. of triplicates, and are representative of 3 independent experiments.

FIG. 8B shows that self-assembled complex binding to native BJAB cells is blocked by increasing amounts of free NP. Free NP, the heterobifunctional ligand, and the IgM anti-NP were all added to BJAB cells and allowed to incubate on ice before washing. Bound IgM was detected as described for FIG. 5B. FIG. 8C shows that the self assembled IgM complex was internalized into cells. After binding of a self-assembled complex of NP-BPC and Alexa Fluor-labeled anti-NP IgM antibodies to BJAB cells on ice, the cells were washed and allowed to internalize the complex for the indicated period of time. After a brief acid wash to remove any surface IgM, internalized IgM was quantified by flow cytometry.

FIG. 10C graphically illustrates internalization of antibody-Siglec F complexes. Data are expressed as internalized mean fluorescence intensity (MFI) of PE-anti-Siglec-F measured as using the data obtained in FIG 10B. Data are the average +S.D. of triplicate determinants.

FIG. 1A is a schematic diagram of wild type and mutant Siglec-F polypeptides. For FIG. 1B, CHO cells that stably expressed wild type and mutant forms of Siglec-F were incubated with PE-anti-Siglec-F (thin line, thick line) or isotype control (shaded) for 30 min on ice. After washing, the cells were allowed to internalize bound antibodies/ligands at 37° C. for the indicated period of time. Following the incubation, cells were washed with 0.2 M glycine buffer pH 2.0 (solid =intracellular) to remove surface bound antibody. As a control, PBS/BSA (shaded, dotted =total probe) was used to wash the cells—thus this control shows both bound and internalized Siglec-F complexed with antibody. Bound and/or internalized antibody was measured by flow cytometry. Representative data of wild-type and double-tyrosine mutant (Y538F and Y561F) Siglec-F are shown. FIG. 11C shows the percent internalization of different Siglec-F polypeptide complexes calculated as (intracellular mean fluorescence intensity/total mean fluorescence intensity)×100 and expressed as a percent of internalization in CHO cells expressing wild-type Siglec-F. Data are the average ±SD of triplicate determinants.

DETAILED DESCRIPTION OF THE INVENTION

Figure 1A:
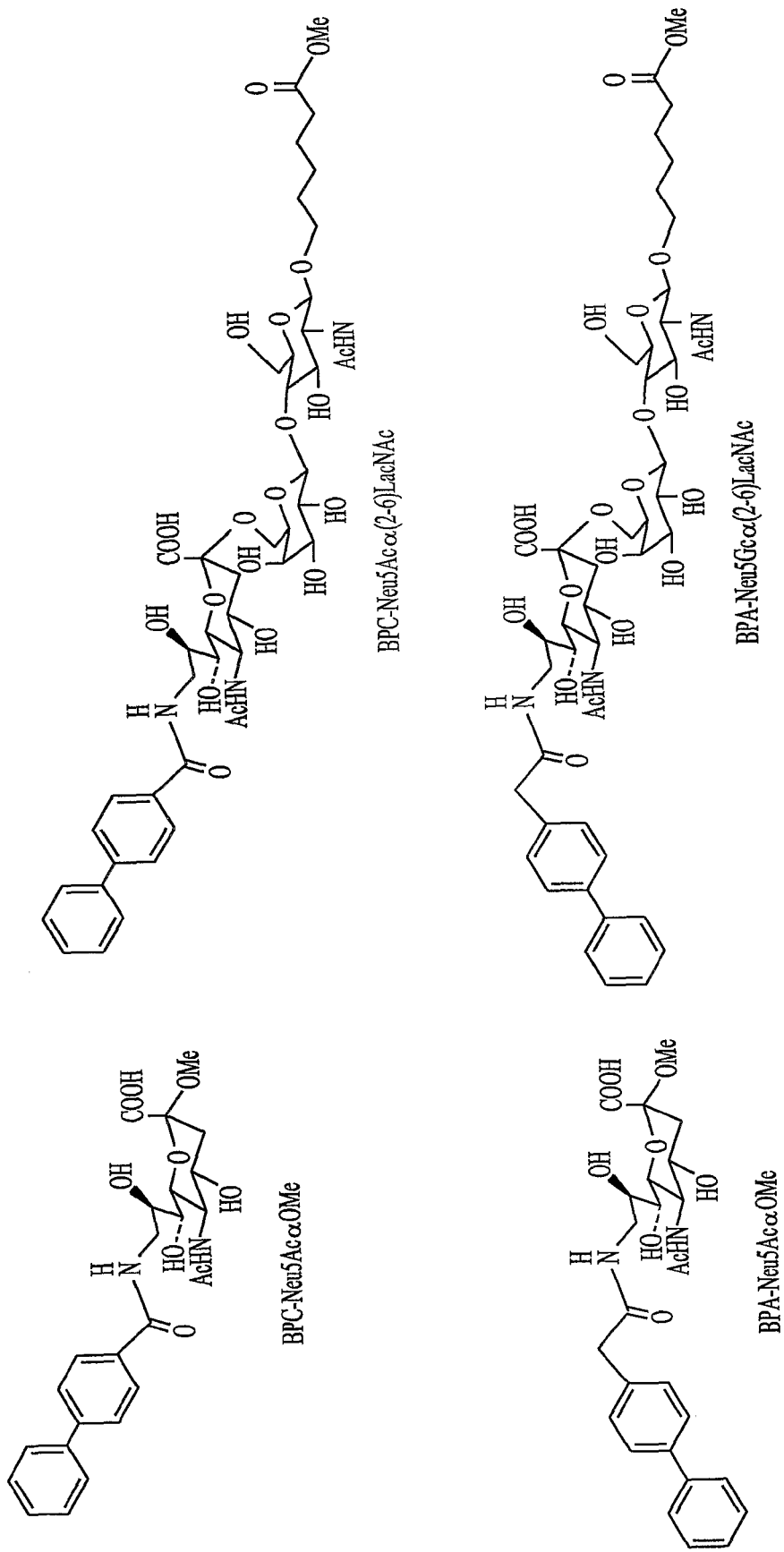
FIG. 1A-B illustrate that sialosides with derivation at position 9 that includes a neutral core and a hydrophobic moiety are potent inhibitors for CD22. Similar inhibitors can be made by derivation at position 5.
Figure 1B:
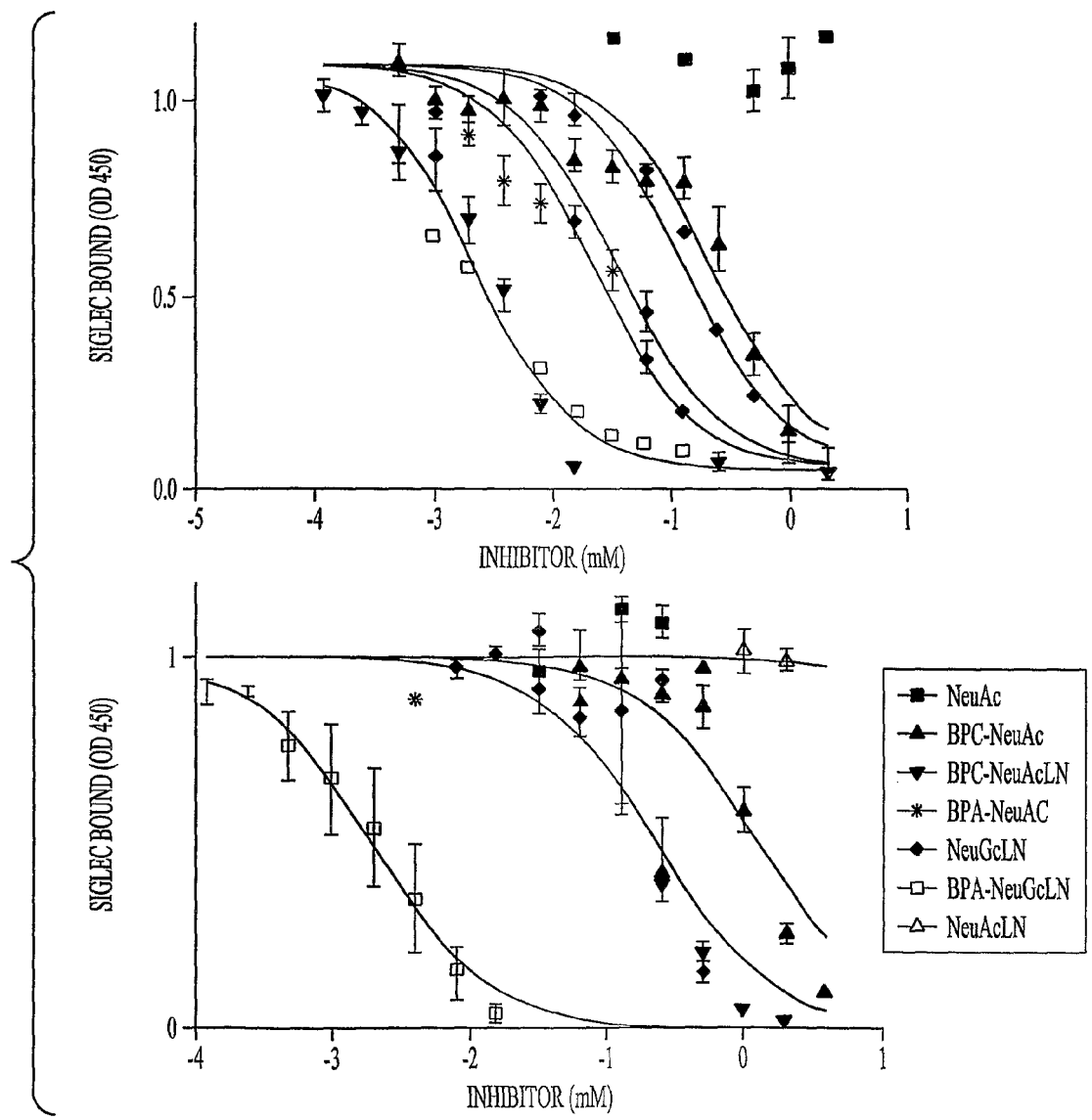

The invention relates to Siglec ligands that have an increased affinity for Siglec receptors. The invention also relates to pharmaceutical compositions that contain the present Siglec ligands and to methods for intracellular delivery of therapeutic agents that involve contacting the cell with a Siglec ligand of the invention that is linked or can be linked to a therapeutic agent. Another aspect of the invention is a method of treating diseases or conditions that are associated with cells that express specific Siglec receptors. These methods involve administering to the mammal an effective amount of a Siglec ligand of the invention that has been linked or binds to a therapeutic agent (e.g., an antibody, anti-tumor agent or anti-cancer agent). In some embodiments, the disease is cancer, asthma, or eczema. A further aspect of the invention is a method for isolating cells that express a Siglec that involves contacting a mixture of cells with a Siglec ligand of the invention that is attached or stably adsorbed to a solid support, and washing the solid support to remove unbound cells. The cells that bind to the Siglec ligands on the solid support express Siglecs and can be eluted as desired.

Siglec Ligands

One aspect of the invention is a Siglec ligand that binds to a Siglec, with high affinity. In one embodiment, the Siglec ligand is a compound of formula Ia, Ib, Ic or Id:

[R$_9$-Sia-Sac-Y]$_n$-Carrier      Ia

[R$_9$-Sia-Sac-Y]$_n$~Carrier      Ib

[R$_5$-Sia-Sac-Y]$_n$-Carrier      Ic

[R$_5$-Sia-Sac-Y]$_n$~Carrier      Id wherein:
$R_5$ and $R_9$ are independently each a hydrogen, hydroxyl, acetylamine, alkyl, alkylamide, cycloalkyl, heteroalkyl, cycloheteroalkyl, aryl, arylalkyl, arylamide or heteroaryl group that can be substituted with one to five alkyl, halo, sulfate or hydroxy groups;
Sia is a sialic acid;
Sac is a neutral saccharide;
Y is a covalent bond to Carrier, a linker that can be attached to Carrier or an antigen that can bind to an antibody Carrier;
the symbol ~ is a non-covalent bond;
n is an integer of from 5 to 500; and Carrier is a polymer, protein, antibody, antigen, multi-subunit protein, protein complex, glycan or solid support; and wherein at least one of $R_5$ or $R_9$ is an alkyl, alkylamide, cycloalkyl, heteroalkyl, cycloheteroalkyl, aryl, arylalkyl, arylamide or heteroaryl group that can be substituted with one to five alkyl, halo, or sulfate groups.

The compounds of formulae Ia, Ib, Ic and Id are covalently attached to the carrier when the symbol— is used and bind to the carrier through non-covalent interactions when the symbol ~ is used.

The compounds of formulae Ia, Ib, Ic and Id are Siglec ligands. Siglecs to which the ligands of the invention can bind include any of Siglecs 1-11. In some embodiments, the Siglec ligands bind, for example, to CD22, Siglec-8, myelin-associated glycoprotein and/or sialoadhesin.

According to the invention, the $R_9$ and/or $R_5$ groups helps provide Siglec binding specificity. Thus, the selection of a $R_9$ and/or $R_5$ group can influence the type of Siglec to which the Siglec ligand will bind. For example, CD22 binds with greater affinity to Siglec ligands when the $R_9$ and/or $R_5$ includes a bulky aromatic group. Such an aromatic group can have about five to about fourteen ring atoms in which at least one ring is aromatic. Examples include a phenyl ring, a bicyclic ring (e.g., biphenyl), or tricyclic ring. Bicyclic and tricyclic rings can be ortho-fused but, as used herein, the bicyclic and tricyclic rings need not be fused and can be separate rings linked together by a covalent bond or a short alkyl (e.g. $C_1$-$C_3$ alkyl). Examples of aromatic groups include groups such as benzene, phenyl, biphenyl, naphthalene, anthracene, or a combination thereof.

Because the $R_9$ and/or $R_5$ groups influence Siglec binding specificity at least one the $R_9$ or $R_5$ groups is an alkyl, alkylamide, cycloalkyl, heteroalkyl, cycloheteroalkyl, aryl, arylalkyl, arylamide or heteroaryl group (that can be substituted with one to five alkyl, halo, or sulfate groups). The other $R_9$ or $R_5$ group can be hydrogen, hydroxy or acetylamine. The alkyl, alkylamide, cycloalkyl, heteroalkyl, cycloheteroalkyl, aryl, arylalkyl, arylamide or heteroaryl group (that can be substituted with one to five alkyl, halo, or sulfate groups) can therefore be placed at the position of either the $R_9$ or $R_5$ group, using procedures described herein (see also, Paulson et al., Nature Chemical Biology 2(5): 238-248 (2006) (especially FIG. 5).

The aryl groups of the $R_9$ or $R_5$ substituents can be substituted with one to five alkyl groups. "Alkyl" is a hydrocarbon having up to 25 carbon atoms. Alkyls can be branched or unbranched moieties, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

As described above, the Siglec ligands of the invention contain sialic acids. Sialic acid is a generic term for a family of 9-carbon atom sugars that include derivatives of neuraminic acid (Neu) or keto-deoxy-nonulsonic acid (KDN). There are approximately 40 naturally occurring sialic acids. The most common sialic acid found in humans is N-acetylneuraminic acid (Neu5Ac or Neu9Ac2). In most other animals (with the notable exception of chickens) Neu5Ac co-exists with N-glycolylneuraminic acid (Neu5Gc), which has a hydroxyl group at the N-acyl position.

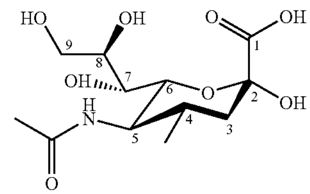

Neu5Ac

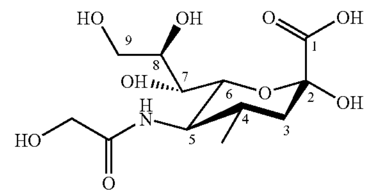

Neu5Gc

Neutral (Sac) saccharides used in the Siglec ligands of the invention have 1-10 sugar residues. The sugar residues can be hexoses or pentoses. The sugar residues of the neutral saccharides can have a variety of substituents including, alkyl, hydroxyalkyl, acyl, N-acyl, ether, amino and other substituents. Sugar residues used in the neutral saccharides can be glucose, glucuronic acid, N-acetylglucose, mannose, mannuronic acid, galactose, galacturonic acid, N-acetylgalactose, gulose, guluronic acid, fucose, xylose, N-acetylneuraminic acid, N-acetyl glucosamine, N-acetyl galactosamine or other sugar units. In some embodiments, the saccharide is an oligosaccharide such as a disaccharide or a trisaccharide. Thus, the saccharide can also be lactose, maltose, sucrose, N-acetyl lactosamine, N-acetyl maltosamine and the like.

As used herein, a "carrier" is a polymer, antibody, antigen, protein, multi-subunit protein, protein complex, glycan or solid support to which a Siglec ligand can bind or is covalently attached. A carrier can be covalently linked directed to one or more Siglec ligands of the invention, or bind non-covalently to one or more Siglec ligands of the invention. When non-covalent association between the present Siglec ligands is contemplated, the non-covalent association can be established prior to administration to or exposure of a subject to a carrier-Siglec ligand complex. Alternatively, when non-covalent association between the present Siglec ligands is contemplated, the non-covalent association can be established during or after administration of a carrier-Siglec ligand complex to a subject. Thus, the carrier-Siglec ligand complex can be assembled in vivo or during an assay.

In addition to being linked to, or associated with, Siglec ligands, carriers can also carry agents to be delivered to cells that express one or more Siglecs. As illustrated herein the present compounds (with or without carriers and therapeutic agents) are bound by and incorporated into Siglec-expressing cells. Carriers used with the Siglec ligands of the invention include any convenient natural or synthetic carrier. Examples of carriers that can be used with the compounds of the invention include polymers, glycans, antigens, peptides, proteins, antibodies, nucleic acids, lipids (e.g. liposomes), polysaccharides, glycoproteins, glycolipids, lipoproteins, beads, chromatography matrices and the like. In some embodiments, the carriers are polyacrylamides, antigens, antibodies, ROMP, TRIS, glycoproteins and derivatives thereof.

Another aspect of the invention is a Siglec ligand of formula IIa:

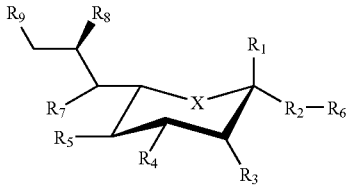

wherein:
X is a methylene or a heteroatom (for example, O, N, or S);
$R_1$ is a carboxylate, carboxy, phosphate or sulfate;
$R_2$ is a neutral saccharide;
$R_3$, $R_4$, $R_7$ and $R_8$ are each independently a hydrogen, a hydroxyl or a acetylamine;
$R_5$ is a hydrogen, hydroxyl, acetylamine, alkyl, alkylamide, cycloalkyl, heteroalkyl, cycloheteroalkyl, aryl, arylalkyl, arylamide or heteroaryl group that can be substituted with one to five alkyl, halo, or sulfate group;
$R_6$ is hydrogen, a Y group, an alkyl, or a carrier; and wherein $[R_5\text{-Sia-Sac-Y}]_n$, $[R_5\text{-Sia-Sac-Y}]_n$, $[R_9\text{-Sia-Sac-Y}]_n$ or $[R_9\text{-Sia-Sac-Y}]_n$ moieties can be attached to the carrier, and wherein n is an integer of from 5 to 500; and
$R_9$ is an alkyl, alkylamide, cycloalkyl, heteroalkyl, cycloheteroalkyl, aryl, arylalkyl, arylamide or heteroaryl group that can be substituted with one to five alkyl, halo, sulfate or hydroxy groups; and
wherein at least one of $R_5$ or $R_9$ is an alkyl, alkylamide, cycloalkyl, heteroalkyl, cycloheteroalkyl, aryl, arylalkyl, arylamide or heteroaryl group that can be substituted with one to five alkyl, halo, or sulfate groups.

Another aspect of the invention is a Siglec ligand of formula IIb:

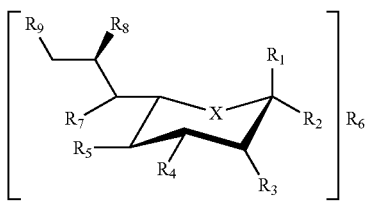

IIb wherein: X, $R_1$, $R_2$, $R_3$, $R_4$, $R_5$, $R_7$, $R_8$ and $R_9$ are as defined above; and $R_6$ is a non-covalently bound carrier.

In some embodiments the $R_2$ and $R_6$ substituents are joined by a linker (e.g., a Y linker group). Linkers or spacer groups that can be used to join $R_2$ and $R_6$ substituents include fairly stable (e.g. substantially chemically inert) chains or polymers. For example, the linkers or spacer groups can be alkylene groups. One example of an alkylene group is —$(CH_2)_q$—, where q is an integer of from 1 to 50. One or two of the ends of the linkers can include functional groups or leaving groups that permit easy attachment of the linker to glycans, carriers or solid supports. Functional groups include carboxylate, amino, esters, and the like. Suitable leaving groups are available in the art and include, for example, alkynes, such as —C≡CH; halides, such as chloride, bromide, and iodide; aryl- or alkylsulfonyloxy, substituted arylsulfonyloxy (e.g., tosyloxy or mesyloxy); substituted alkylsulfonyloxy (e.g., haloalkylsulfonyloxy); phenoxy or substitute phenoxy; and acyloxy groups.

Further examples of neutral saccharides that can be used in the invention include saccharides of formula IIIa:

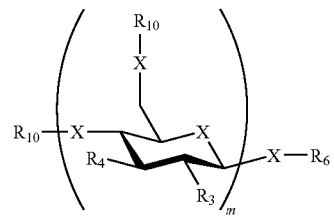

wherein:
X is methylene or a heteroatom (for example, O, N, or S);
$R_3$ and $R_4$ are each independently a hydrogen, a hydroxyl or a acetylamine;
$R_6$ is hydrogen, a Y group, an alkyl, or a carrier;
m is an integer of from 1 to 10; and
each $R_{10}$ is sugar residue, a saccharide or [$R_9$-Sia], wherein R9 is as defined herein; and
Sia is a sialic acid.

Additional examples of neutral saccharides that can be used in the invention include saccharides of formula IIIb:

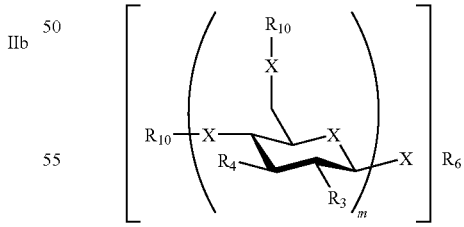

wherein: X, $R_3$, $R_4$ and $R_{10}$ are as defined above; and $R_6$ is a non-covalently associated carrier.

Specific examples of Siglec ligands of the invention include the following, wherein $R_6$ and $R_9$ are as defined herein.

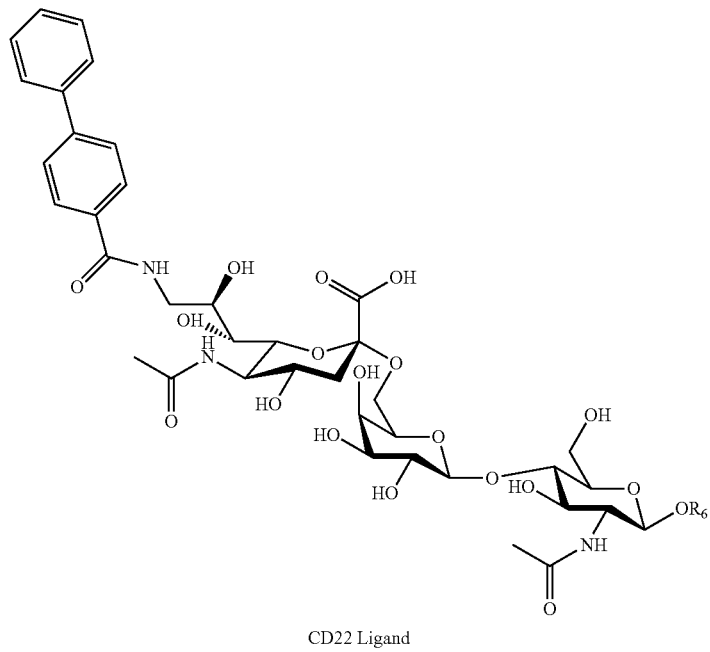
CD22 Ligand
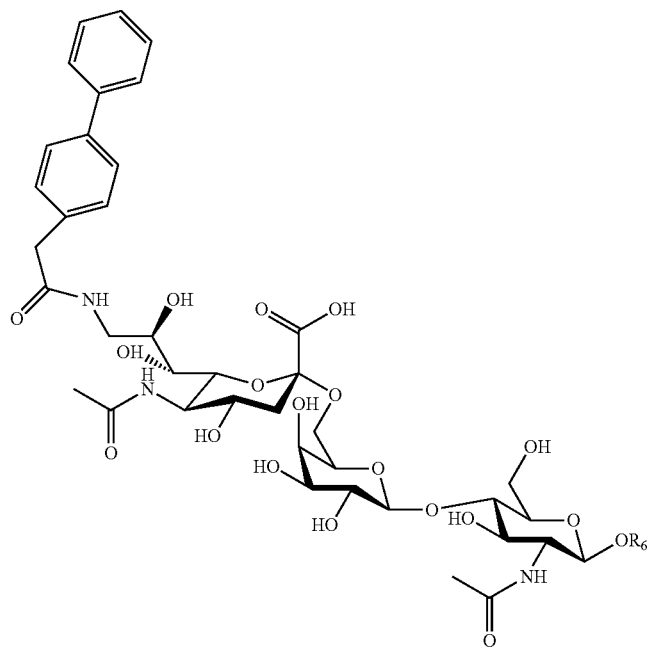
CD22 Ligand

-continued
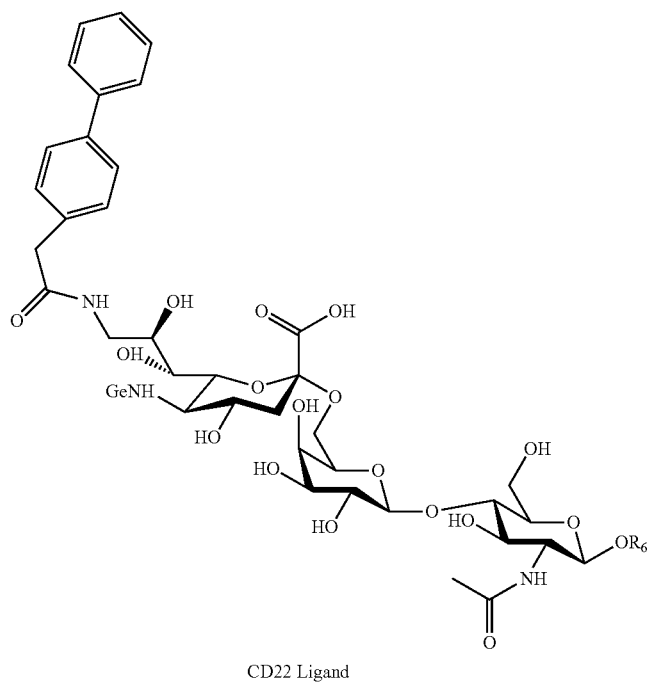
CD22 Ligand
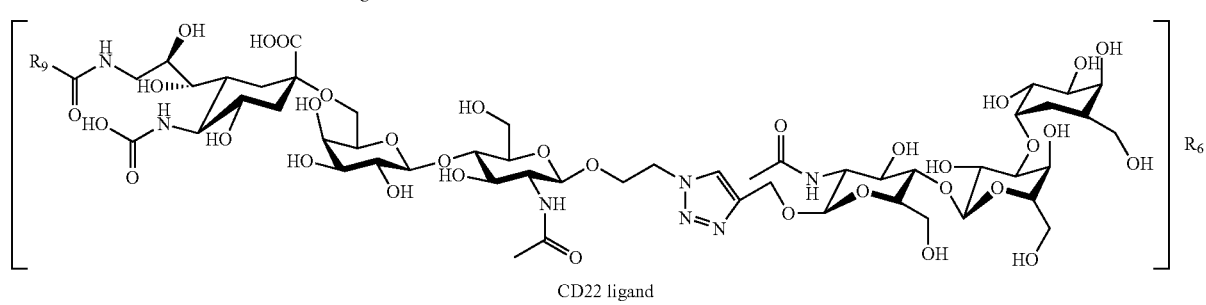
CD22 ligand
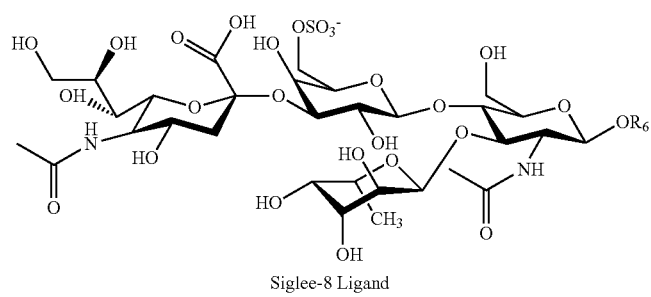
Siglec-8 Ligand
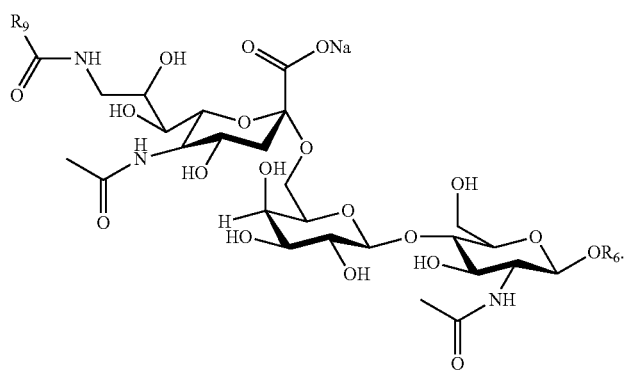
MAG Ligand R$_9$ substituents that work well for MAG ligands include the following:

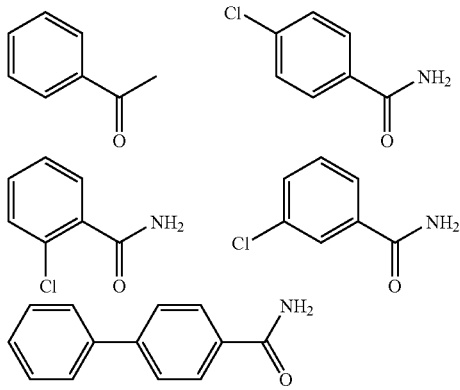

Siglecs

Sialic-acid binding Ig-like lectins (siglecs) are cell-surface receptors expressed by cells that are often involved in the immune system. At least eleven different Siglecs have been identified: sialoadhesion (Siglec-1), CD22 (Siglec-2), CD33 (Siglec-3), myelin-associated glycoprotein (MAG, Siglec-4), Siglec-4-b (Schwann cell myelin protein or SMP), Siglec-5 (OB-BP2), Siglec-6 (OB-BP1, CD33L), Siglec-7, Siglec-8, Siglec-9, Siglec-10 and Siglec-11. The structures of these Siglecs are closely related and are believed to have arisen by gene duplication. In the murine genome, eight Siglecs have been identified. Five of these mouse Siglecs are believed to be orthologs for sialoadhesion, CD22, CD33, MAG and Siglec-10 (mSiglec-G). The remaining three mouse Siglecs (Siglec-E, Siglec-F and Siglec-H) are related to CD33. The present invention contemplates ligands for each of these Siglecs.

Figure 13:
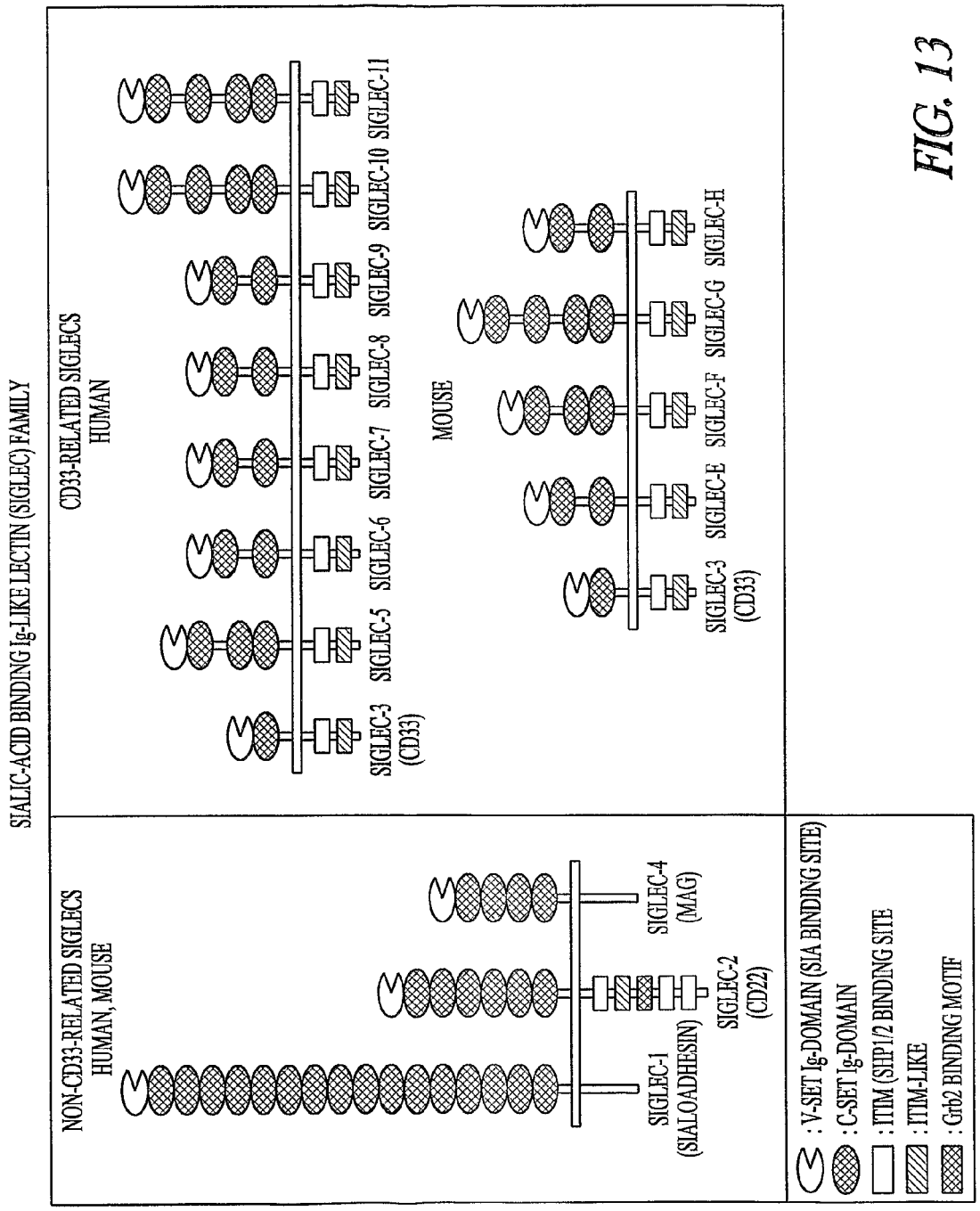
FIG. 13 illustrates Siglec structures, showing the sialic acid binding domain, the Ig domain(s), the immuno-receptor tyrosine-based inhibitory motif (ITIM) and the position of the Siglec in the cellular membrane.
Figure 14:
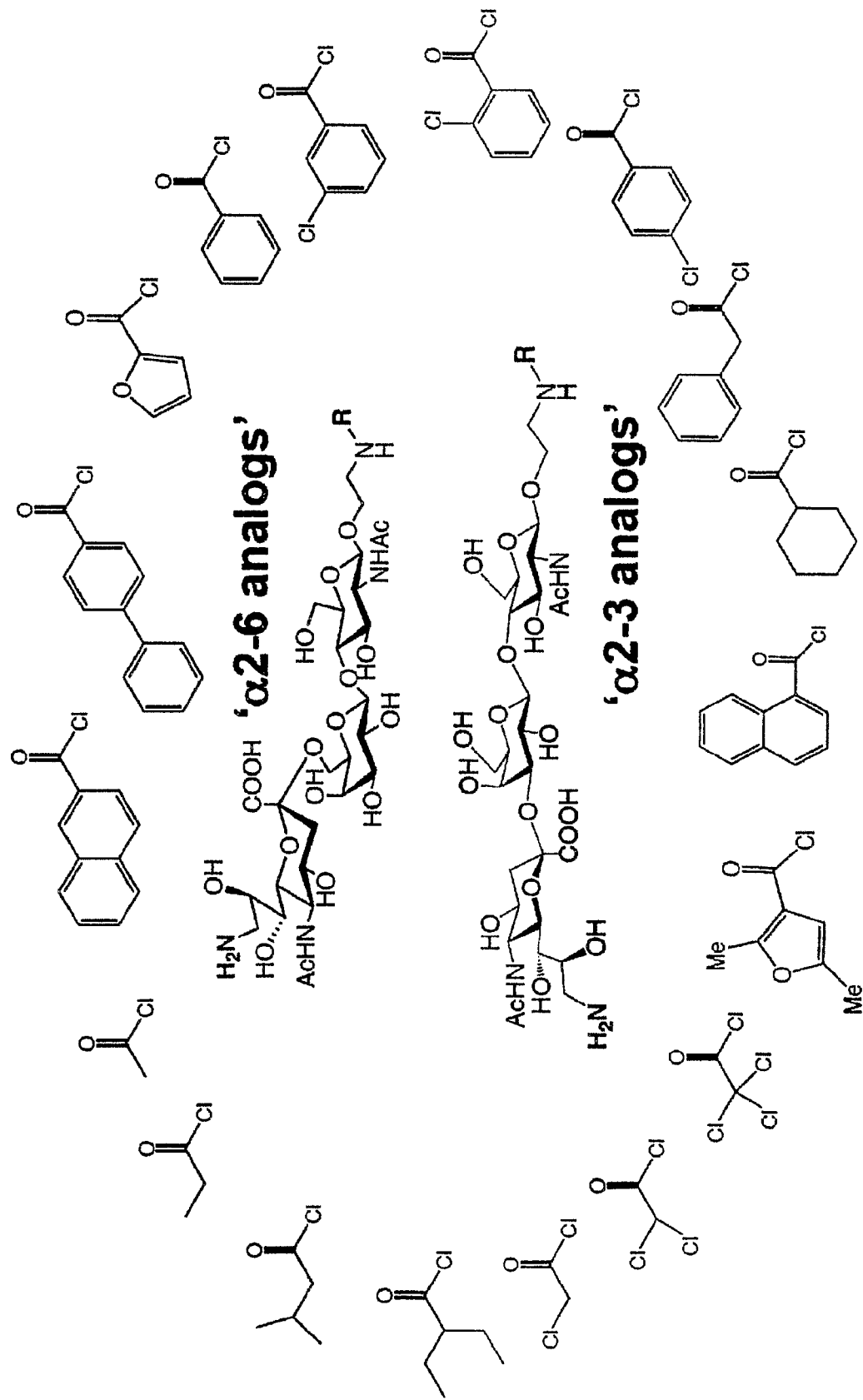
FIG. 14 provides examples of some $R_9$ and $R_5$ substituents that can be used in the Siglec ligands of the invention.

Siglecs consist of variable numbers of extracellular Ig domains with an N-terminal sugar-binding domain, a transmembrane domain, and a cytoplasmic domain containing two or more tyrosine-based motifs (see, FIG. 13; Crooker, Curr. Opin. Pharmacol. 5:431-37 (2005); Varki & Angata, Glycobiology 16: 1R-27R (2006)). Because some of the tyrosine-based motifs conform to immuno-receptor tyrosine-based inhibitory motifs (Vivier & Daeron, Immunol. Today 18: 286-91 (1997)), Siglecs are generally believed to play important roles as inhibitory receptors of cell signaling (Crocker, 2005; Varki and Angata, 2006).

In fact, it has been documented that CD22, the best-characterized Siglec of the immune system, functions as a negative regulator of B-cell receptor signaling. Nitschke et al., Curr. Biol. 7: 133-43 (1997); Nitschke & Tsubata, Trends Immunol. 25: 543-50 (2004); Sato et al., Semin. Immunol. 10 :287-97 (1998); Tedder et al., Adv. Immunol. 88 :1-50 (2005). Upon antigen binding to the B-cell receptor, the tyrosine residues in the immuno-receptor tyrosine-based inhibitory motifs (ITIMs) of CD22 are quickly phosphorylated and recruit protein tyrosine phosphatase SHP-1, which dephosphorylates the B-cell receptor and dampens the B cell response (Nitschke & Tsubata, 2004; Tedder et al., 2005). Thus, CD22 is important for setting the threshold of B-cell receptor signaling.

CD33 is a Siglec expressed by monocytic/myeloid lineage cells including most acute myeloid leukemias.

Mouse Siglec-F is a CD33-related Siglec, which is characteristically expressed on mouse eosinophils and which binds 6'-sulfo-sLe$^x$ (Neu5Ac$\alpha$2-3[6-SO$_4$]Gal$\beta$1-4[Fuc$\alpha$1-3]GlcNAc ) as a preferred glycan ligand.

Human Siglec-8 and mouse Siglec F are thought to be functionally equivalent paralogs. Like Siglec-F, Siglec-8 is expressed on human eosinophils and binds to 6'-sulfo-sLe$^x$ (Neu5Ac$\alpha$2-3[6-SO$_4$]Gal$\beta$1-4[Fuc$\alpha$1-3]GlcNAc) (Bouchner et al. J. Biol. Chem. 280: 4307-12 (2005); Floyd et al., J. Biol. Chem. 275: 861-66 (2000)). These siglecs are of particular interest in the context of allergic diseases because the infiltration, accumulation, and degranulation of eosinophils in the lung is a hallmark of active asthma. Siglec-8 ligation with antibodies triggers human eosinophil apoptosis. Thus, the invention contemplates Siglec-8 ligands that are covalently or non-covalently bound to therapeutic agents (e.g. antibodies) for the treatment of eosinophil-related diseases.

CD33-related siglecs including Siglec-5, CD33, and Siglec-H have been demonstrated to undergo endocytosis following antibody binding. Jones et al. Mol. Microbiol. 49: 1213-25 (2003); Walter et al. Blood 105: 1295-1302 (2005)). As shown herein, Siglec-F undergoes endocytosis, and can also mediates endocytosis of the synthetic sialoside probe and sialylated bacteria. In view of the endocytic properties of Siglecs, the Siglec ligands of the invention can be used to deliver agents to cells that express Siglecs.

Siglec proteins are thought to be involved in diverse biological processes such as hematopoiesis, neuronal development and immunity (Vinson, M. et al., 1996 supra). Studies also suggest that Siglec proteins mediate cell adhesion/cell signaling through recognition of sialyated cell surface glycans (Kelm, S. et al., 1996 Glycoconj. J. 13:913-926; Kelm, S. et al., 1998 Eur. J. Biochem. 255:663-672; Vinson, M. et al., 1996 J. Biol. Chem. 271:9267-9272).

Siglec proteins are typically expressed in diverse hematopoietic cell types, yet they all share a similar structure including a single N-terminal V-set domain (membrane-distal) followed by variable numbers of extracellular C2-set domains, a transmembrane domain, and a short cytoplasmic tail. Additionally, the terminal V-set domain has an unusual intrasheet disulfide bridge that is unique among members of the Ig superfamily (Williams, A. F. and Barclay, A. N. 1988 Annu. Rev. Immunol. 6:381-405; Williams, A. F., et al., 1989 Cold Spring Harbor Symp. Quant. Biol 54:637-647; Pedraza, L., et al., 1990 J. Cell. Biol. 111:2651-2661).

Use of truncating mutants (Nath, D., et al., J. Biol. Chem. 270:26184-26191), site-directed mutagenesis (Vinson, M., et al., 1996 J. Biol. Chem. 271:9267-9272; Van der Merwe, P. a., et al., 1996 J. Biol. Chem. 271:9273-9280), X-ray crystallography and NMR (discussed in: Crocker, P. R., et al., 1997 Glycoconjugate J. 14:601-609) have demonstrated that the GFCC'C" face of the N-terminal V-set domain of known Siglec proteins interact with sialic acid. Thus, the V-set domain mediates cell-to-cell adhesion by interacting with sialic acid. In particular, an arginine residue within the V-set domain is a key amino acid residue for binding to sialic acid (Vinson, M., et al., 1996 supra).

While the invention contemplates high affinity ligands for all Siglecs, in some embodiments, the ligands are directed against CD22 (Siglec-2). Amino acid sequences for CD22 are available. An example of an amino acid sequence for a human CD22 protein can be found in the National Center for Biotechnology Information (NCBI) database (http://www.ncbi.nlm.nih.gov/) at accession number NP 001762 (gi: 4502651), and is reproduced below (SEQ ID NO: 1).

```
  1 MHLLGPWLLL LVLEYLAFSD SSKWVFEHPE TLYAWEGACV

41 WIPCTYRALD GDLESFILFH NPEYNKNTSK FDGTRLYEST

81 KDGKVPSEQK RVQFLGDKNK NCTLSIHPVH LNDSGQLGLR

121 MESKTEKWME RIHLNVSERP FPPHIQLPPE IQESQEVTLT

161 CLLNFSCYGY PIQLQWLLEG VPMRQAAVTS TSLTIKSVFT

201 RSELKFSPQW SHHGKIVTCQ LQDADGKFLS NDTVQLNVKH

241 TPKLEIKVTP SDAIVREGDS VTMTCEVSSS NPEYTTVSWL

281 KDGTSLKKQN TFTLNLREVT KDQSGKYCCQ VSNDVGPGRS

321 EEVFLQVQYA PEPSTVQILH SPAVEGSQVE FLCMSLANPL

361 PTNYTWYHNG KEMQGRTEEK VHIPKILPWH AGTYSCVAEN

401 ILGTGQRGPG AELDVQYPPK KVTTVIQNPM PIREGDTVTL

441 SCNYNSSNPS VTRYEWKPHG AWEEPSLGVL KIQNVGWDNT

481 TIACARCNSW CSWASPVALN VQYAPRDVRV RKIKPLSEIH

521 SGNSVSLQCD FSSSHPKEVQ FFWEKNGRLL GKESQLNFDS

561 ISPEDAGSYS CWVNNSIGQT ASKAWTLEVL YAPRRLRVSM

601 SPGDQVMEGK SATLTCESDA NPPVSHYTWF DWNNQSLPHH

641 SQKLRLEPVK VQHSGAYWCQ GTNSVGKGRS PLSTLTVYYS

681 PETIGRRVAV GLGSCLAILI LAICGLKLQR RWKRTQSQQG

721 LQENSSGQSF FVRNKKVRRA PLSEGPHSLG CYNPMMEDGI

761 SYTTLRFPEM NIPRTGDAES SEMQRPPRTC DDTVTYSALH

801 KRQVGDYENV IPDFPEDEGI HYSELIQFGV GERPQAQENV

841 DYVILKH
```

Carriers

As used herein, a "carrier" is a polymer, antibody, antigen, protein, multi-subunit protein, protein complex, glycan or solid support to which a Siglec ligand can bind or is covalently attached. Carriers can be covalently attached to the Siglec ligand, or carriers can bind in a non-covalent manner to the Siglec ligand. In general, the carrier is used to display several copies of the Siglec ligand, thereby generating a "multivalent" carrier-Siglec ligand complex that optimally competes for binding sites on Siglec receptors, especially when the Siglec receptor is a cell-surface Siglec receptor. The cell-surface of many cells has many glycans, including glycans that bind to Siglec receptors present on the same cell surface. Hence, as shown herein, such an abundance of cell-surface bound ligands can prevent binding of cell-membrane-associated Siglec receptors to soluble ligands offered in trans, unless those trans ligands are multivalent ligands and the ligands exhibit avidity for the Siglec receptor. Therefore, one function for the carrier is to display multiple (e.g., 5 to 500) copies of the Siglec ligands of the invention.

Carriers can be associated or linked to Siglec ligands prior to their use in assays or in the compositions and methods of the invention. Alternatively, a Siglec ligand-carrier association can form during an assay, during a method of the invention, or after administration of a composition to a subject.

As described herein, several types of carriers have been used successfully including polymers (e.g., polyacrylamide (PAA)) and antibodies (e.g. anti-nitrophenyl IgM, and nitrophenyl-antibody complexes).

While a carrier can be an inert material or molecule without many (or even any) biological properties, it can also have significant biological activity. Thus, for example, when associated or bound with a Siglec ligand, an antibody may serve as a carrier because it can display several or many copies of the Siglec ligand. However, such an antibody carrier can also activate an immune response, including activating complement, opsonization of antibody-CD22 complex, antibody-dependent cell-mediated cytotoxicity of natural killer lymphocytes, and the like. Thus, when an antibody is used as a carrier, the antibody can lead to cell death of the Siglec-expressing cell to which ligand and antibody is attached. Therefore, an antibody carrier has biological properties that can advantageously be used in the therapeutic compositions and methods of the invention.

The antigen carriers and Y groups can also be biologically significant. As described herein Y is a covalent bond to Carrier, a linker that can be attached to Carrier or an antigen that can bind to an antibody Carrier. Thus, the Y group mediates or facilitates binding between the Siglec ligand and the carrier. However, the Y group can play a biologically significant role in the Siglec ligands of the invention because the Y group can be an antigen. Such antigens can be attached to the Siglec ligand and then attract an antibody carrier, which when bound either in vitro or in vivo, forms a Siglec ligand-antigen-antibody complex. This complex can bind to Siglec receptors on the surface of cells. For example, as shown herein, a CD22 Siglec ligand attached to a nitrophenyl (NP) antigen can be bound to anti-NP IgM antibodies. Surprisingly, these CD22 Siglec ligand-NP-IgM complexes bind to native B cells (see Examples). When exposed to serum that contains complement factors, the cell-bound CD22 Siglec ligand-NP-IgM complexes induce the complement cascade and the B cells are lysed (i.e., killed, see Examples).

Accordingly, the invention also provides methods of treating B cell-related diseases, including leukemias, lymphomas and the like, that involve administering the Siglec ligands of the invention to a mammal, where the Siglec ligands are attached to an antigen that can bind an antibody (e.g., an IgM antibody).

In another embodiment, one of skill in the art may attach an antigen to the Siglec ligands of the invention, where the antigen may induce an immune response and/or antibody production when administered to mammal. In some embodiments, a single small antigen is attached to the Siglec ligand. In other embodiments, two or more Siglec ligands may be attached to such an antigen. Alternatively, many Siglec ligands (e.g. 5-500) may be attached to the antigen.

As illustrated herein, a small antigen can be attached to a single Siglec ligand to generate a small Siglec ligand-Ag molecule. Thus, a CD22 ligand was linked to the small antigen nitrophenyl. When the small Siglec ligand-Ag molecule was mixed with a multivalent antibody (e.g. an IgM antibody) that can bind up to ten copies of the small antigen, this multivalent complex of CD22 ligands readily bound to native B cells that expressed CD22. Such binding to native B cells was made possible by the specificity and avidity of the CD22 ligand and by using multivalent display of these CD22 ligands on IgM antibody carriers. Moreover, when serum containing complement factors was incubated with the mixture of Siglec ligand-Ag plus IgM antibodies plus B cells, the IgM antibodies induced complement-based killing of the B cells.

Thus, the antigen can be a small molecule or a large molecule. Examples of antigens that can be used include small molecules, peptides, proteins, glycans, glycopeptides, glycoproteins and the like.

In some embodiments, the antigen is a glycan having the structure galα1-3gal, which is bacterial antigen not found in human tissues. However, essentially all mammals have been exposed bacteria and have developed immunity to the gal$\alpha$1-3gal antigen. Therefore, when the gal$\alpha$1-3gal antigen is linked to the Siglec ligands of the invention, and this Siglec ligand-gal$\alpha$1-3gal antigen is administered to a mammal, the Siglec ligand will bind to Siglec-expressing cells and the antigen will induce an immune response that can kill the Siglec-expression cells. Different populations of Siglec-expressing cells can thereby be targeted for destruction by the mammal's own immune system by selecting a Siglec ligand that is specific for a given cell type.

In another embodiment, the carrier can be a multi-subunit protein. A multi-subunit protein generally consists of several polypeptide chains. The separate polypeptide chains can have similar or different structures. One example of such a multi-subunit protein is serum amyloid protein.

In addition, the carrier can be a solid support. Examples of solid supports that can be used in the invention include beads, chips, microtiter plates, slides, chromatographic matrixes and the like. In some embodiments, the solid support is a magnetic bead.

Thus, the carriers used in the invention can be polymers, proteins (e.g., antigens or antibodies), protein complexes (e.g., antigen-antibody complexes), multi-subunit proteins (e.g., serum amyloid protein), glycans (e.g., galα1-3gal) or solid supports.

Methods of Treating Disease

According to the invention, the present ligands can be used to treat diseases relating to undesirable levels of Siglec expression or undesirable levels of cells that express Siglecs.

One method for treating such a disease in a mammal involves administering to the mammal a therapeutically effective amount of a Siglec ligand of the invention, where the Siglec ligand is linked or non-covalently joined to a therapeutic agent. The therapeutic agent can be directly linked to the Siglec ligand. Alternatively, the Siglec ligand can merely bind to a therapeutic agent in situ, or induce the formation of a therapeutic agent after administration to the mammal. For example, the Siglec ligand can be attached to an antigen that binds to an antibody (a therapeutic agent) or that induces an immune response after administration to the mammal (thereby forming therapeutic agents in situ).

In another embodiment, the therapeutic agent can be directly linked to a therapeutic agent. Alternatively, the therapeutic agent can be incorporated into a liposome, where the liposome is a carrier to which the Siglec ligand is attached.

Diseases that are associated with undesirable levels of Siglec expression or with undesirable levels of cells that express Siglecs include a variety of lymphomas, B cell lymphomas, leukemias, immunodeficiencies, B cell lymphoproliferative disorders, B cell neoplasms. Cancerous cells that express CD22, include the majority of non-Hodgkin's lymphoma, Bacute lymphocytic leukemia, acute lymphoblastic leukemia, and chronic lymphocytic leukemia. In some embodiments the disease is a B cell lymphoma.

B cell lymphomas include B cell leukemias, chronic lymphocytic leukemia and small lymphocytic lymphoma. B-cell leukemia is any of a group of diseases of the reticuloendothelial system that preferentially affect B-cells and involve uncontrolled proliferation of white blood cells (leukocytes). A B-cell lymphoma is any of a group of malignancies of lymphoid tissue (lymph nodes, spleen, and other organs) that preferentially affects B-cells. B-cell lymphomas and leukemias include, for example: B-cell lymphoblastic leukemia/lymphoma, B-cell chronic lymphocytic leukemia/small lymphocytic lymphoma, lymphoplasmacytic lymphoma, splenic marginal zone B-cell lymphoma, hairy cell leukemia, extra-nodal marginal zone B-cell lymphoma of the mucosa-associated lymphoid tissue (MALT) type, mantle cell lymphoma, follicular lymphoma, nodal marginal zone lymphoma with or without monocytoid B cells, diffuse large B-cell lymphoma, and Burkitt's lymphoma. B-cell lymphomas and 3-cell leukemias are associated with increased expression of cell-surface CD22.

Therapeutic agents contemplated by the invention include drugs, antigens, small molecules, antibodies, cytokines, interferons, anti-viral agents, anti-bacterial agents and anti-tumor or anti-cancer agents. In some embodiments, the therapeutic agent is an anti-tumor agent. An anti-tumor agent, anti-cancer agent, or antineoplastic is any drug that controls or kills neoplastic cells. An anti-tumor agent is used in chemotherapy as a component of an anti-tumor therapy to kill cancer cells. Anti-tumor agents and drugs used in anti-tumor therapy include, but are not limited to: Altretamine, Asparaginase, BCG, Bleomycin sulfate, Busulfan, Carboplatin, Carmustine, Chlorambucil, cis-platinum, cis-diammine-dichloroplatinum, 2-chlorodeoxyadenosine, Cyclophosphamide, cytosine arabinoside, Dacarbazine imidazole carboxamide, Dactinomycin, Daunorubicin, daunomycin, Dexamethasone, Doxorubicin, Etoposide, epipodophyllotoxin, Floxuridine, Fluorouracil, Fluoxymesterone, Flutamide, Fludarabine, Goserelin, Hydroxyurea, Idarubicin HCL, Ifosfamide, Isophosphamide, Interferon .alpha., Interferon .alpha.2.alpha., Interferonα2b, Interferonαn3, Irinotecan, Leucovorin calcium, Leuprolide, Levamisole, Lomustine, Megestrol, Melphalan, L-phenylalanine mustard, Melphalan hydrochloride, MESNA, Mechlorehamine, Methylprednisolone, Methotrexate, Amethopterin, Mitomycin, Mitomycin-C, Mitoxantrone, Mercaptopurine, Paclitaxel, Plicamycin, Mithramycin, Prednisone, Procarbazine, Streptozocin, Tamoxifen, 6-thioguanine, Thiotepa, triethylene thiophosphoramide, Vinblastine, Vincristine, and Vinorelbine tartrate.

In some embodiments, an antibody can serve as a therapeutic agent and a carrier. This is because the antibody can tag an antigen linked to a Siglec ligand (which may be bound to a Siglec-expressing cell) for recognition and processing by the immune system. Such processing by the immune system can lead to death of the Siglec-expressing cell.

Thus, an antigen can be directly attached to the Siglec ligand, and the antibody can be directly or indirectly attached to the Siglec ligands of the invention. For example, a small antigen can be covalently linked to a Siglec ligand. The Siglec ligand-Ag compound can be administered to a mammal to induce an immune response against the antigen. Alternatively, the Siglec ligand-Ag compound can be mixed with a selected antibody preparation to form a Siglec ligand-Ag-Ab complex. Upon administration to a mammal, the Siglec ligand-Ag compound (with or without pre-incubation with an antibody) can bind to a Siglec-expressing cell and an antibody that recognizes the antigen can induce the complement system to kill the cell.

The complement system is made up of about 25 proteins that work together to "complement" the action of antibodies in destroying cells (including bacterial cells and cells tagged by antigens). In particular, complement also helps to rid the body of antibody-coated antigens (antigen-antibody complexes). Complement proteins circulate in the blood in an inactive form. When the first protein in the complement series is activated—typically by antibody that has locked onto an antigen—it sets in motion a domino effect. Each component takes its turn in a precise chain of steps known as the complement cascade. The result is death (e.g. lysis) of cells bound by antigen-antibody complexes.

Thus, antigens and/or antibodies attached to Siglec ligands of the invention are powerful therapeutic tools for destroying selected Siglec-expressing cells.

Methods for Detecting or Monitoring Disease

According to the invention, the present ligands can be used to detect and/or monitor diseases that are related to undesirable levels of Siglec expression or undesirable levels of cells that express Siglecs. For example, B cells express CD22. Occasionally, proliferation of a particular B cell will continue unabated; such proliferation can result in a cancer referred to as "B cell lymphoma." Healthy persons have significantly lower levels of such B cells. Such elevated levels of B cells can be detected using the Siglec ligands of the invention.

Thus, one aspect of the invention is a method of detecting undesirable levels of cells that express Siglecs by contacting a test cell sample with a Siglec ligand of the invention and detecting whether the ligand binds to or is internalized within a significant number of cells in the test cell sample. Another aspect of the invention is a method of detecting undesirable levels of Siglec expression in a cell by contacting a test cell sample with a Siglec ligand of the invention and detecting whether significantly larger amounts of the ligand bind to or are internalized within the cell compared to a control cell. The control cell can be a cell known to express normal (desirable) levels of a Siglec.

Diseases that are associated with undesirable levels of Siglec expression or with undesirable levels of cells that express Siglecs include a variety of lymphomas, B cell lymphomas, leukemias, immunodeficiencies, B cell lymphoproliferative disorders, B cell neoplasms. Cancerous cells that express CD22, include the majority of non-Hodgkin's lymphoma, Bacute lymphocytic leukemia, acute lymphoblastic leukemia, and chronic lymphocytic leukemia. In some embodiments the disease is a B cell lymphoma.

B cell lymphomas include B cell leukemias, chronic lymphocytic leukemia and small lymphocytic lymphoma. B-cell leukemia is any of a group of diseases of the reticuloendothelial system that preferentially affect B-cells and involve uncontrolled proliferation of white blood cells (leukocytes). A B-cell lymphoma is any of a group of malignancies of lymphoid tissue (lymph nodes, spleen, and other organs) that preferentially affects B-cells. B-cell lymphomas and leukemias include, for example: B-cell lymphoblastic leukemia/lymphoma, B-cell chronic lymphocytic leukemia/small lymphocytic lymphoma, lymphoplasmacytic lymphoma, splenic marginal zone B-cell lymphoma, hairy cell leukemia, extranodal marginal zone B-cell lymphoma of the mucosa-associated lymphoid tissue (MALT) type, mantle cell lymphoma, follicular lymphoma, nodal marginal zone lymphoma with or without monocytoid B cells, diffuse large B-cell lymphoma, and Burkitt's lymphoma. B-cell lymphomas and 3-cell leukemias are associated with increased expression of cell-surface CD22.

The patient may or may not have such a disease. In this case, the methods of the invention are used to diagnose or detect whether the patient has disease or has a propensity for developing disease. Alternatively, the methods of the invention can be used with patients that are known to have disease. In this case, the prognosis of the breast cancer can be monitored.

Detecting a disease therefore refers to quantitatively or qualitatively determining the presence of a Siglec. For example, detecting a B-cell leukemia or B-cell lymphoma includes quantitatively or qualitatively determining the presence of CD22 on or within a cell in a test sample. Monitoring a B-cell lymphoma or B-cell leukemia includes detecting a B-cell lymphoma or B-cell leukemia, or detecting the progression or regression of a B-cell lymphoma or B-cell leukemia. Diagnosing or diagnosis of a B-cell lymphoma or B-cell leukemia includes both detecting a B-cell lymphoma or B-cell leukemia and identifying a B-cell lymphoma or B-cell leukemia, for example identifying a B-cell leukemia as hairy cell leukemia or chronic lymphocytic leukemia.

Clinical progression of a disease or disorder can also be monitored. Clinical progression of a disease or disorder refers to a general worsening of the disease or disorder, or an increase in the likelihood of developing the disease or disorder. For example, clinical progression of a B-cell leukemia or B-cell lymphoma includes an increase in tumor burden or tumor load, the number of cancer cells, the size of a tumor, or the amount of cancer in a body. In some examples, clinical progression of a B-cell leukemia or B-cell lymphoma includes an increase in a level of cells that express CD22 relative to the level found in a subject who does not have a known B-cell leukemia or lymphoma, or relative to a level of CD22-expressing cells in a population of subjects who do not have a known B-cell leukemia or lymphoma, or relative to the level of CD22-expressing cells in a sample taken at an earlier time. Clinical regression of a disease or disorder refers to a general improvement in the disease or disorder, or to a decrease in the likelihood of developing the disease or disorder. For example, clinical regression of a B-cell leukemia or B-cell lymphoma includes a decrease in tumor burden or tumor load, the number of cancer cells, the size of a tumor, or the amount of cancer in a body. In some examples, clinical regression of a B-cell leukemia or B-cell lymphoma includes a decrease in the levels of cells that express CD22 relative to the level of cells that express CD22 in a sample taken from the subject at an earlier time.

In some embodiments, the ligands of the invention are labeled to facilitate detection of the ligand and any cells or Siglecs bound to the ligand. A label is any molecule or composition that is detectable by, for instance, spectroscopic, photochemical, biochemical, immunochemical, electrical, optical, or chemical means. Examples of labels that can be attached to or used with the ligands of the invention include radioactive isotopes, enzyme substrates, co-factors, ligands, chemiluminescent or fluorescent agents, haptens, enzymes, colloidal gold particles, colored latex particles, and epitope tags. Many of these labels have been disclosed previously and are known to those of ordinary skill (see, for instance, U.S. Pat. Nos. 4,275,149; 4,313,734; 4,373,932; and 4,954,452).

A test sample is obtained from a patient for detecting a disease. The test sample obtained from the patient can be any tissue, pathology or bodily fluid sample. For example, the test sample can be a blood sample, a serum sample, a plasma sample, a urine sample, a breast milk sample, an ascites fluid sample or a tissue sample. In many embodiments, the sample is a blood sample.

Dosages, Formulations and Routes of Administration

The compositions of the invention are administered so as to ameliorate one or more symptoms of disease. In some embodiments, the compositions of the invention are administered so as to achieve a reduction in at least one symptom associated with cancer. The compounds of the invention are particularly amenable to formulation into pharmaceutical compositions because they are composed of glycans that have substantially no toxicity. Moreover, compared to many biological molecules, the glycans of the invention are relatively small and stable. Hence, the present Siglec ligands are readily formulated into highly effective, stable and substantially non-toxic compositions.

To achieve the desired effect(s), the therapeutic agent linked to a Siglec ligand or the combination of therapeutic agents directly or indirectly linked to or associated with Siglec ligands, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, what types of therapeutic agents and Siglec ligands are administered, the route of administration, the progression or lack of progression of the disease (e.g. cancer), the weight, the physical condition, the health, the age of the patient, whether prevention or treatment is to be achieved, and if the ligand is chemically modified. Such factors can be readily determined by the clinician employing animal models or other test systems that are available in the art.

Siglec ligands directly or indirectly linked to therapeutic agents may administered in a single dose, in multiple doses, in a continuous or intermittent manner, depending, for example, upon the recipient's physiological condition, whether the purpose of the administration is therapeutic or prophylactic, and other factors known to skilled practitioners. The administration of these ligand-bound therapeutic agents may be essentially continuous over a pre-selected period of time or may be in a series of spaced doses. Both local and systemic administration is contemplated.

To prepare the composition, the ligand-associated therapeutic agents or combinations thereof are synthesized or otherwise obtained, and purified as necessary or desired. These ligand-associated therapeutic agents can then be lyophilized or stabilized, their concentrations can be adjusted to an appropriate amount, and these ligand-associated therapeutic agents can optionally be combined with other agents.

In general, dosage forms of the invention comprise an amount of at least one of the agents of the invention effective to treat or prevent the clinical symptoms of a disease (e.g. a cancer such as a lymphoma or leukemia). Any statistically significant attenuation of one or more symptoms of cancer is considered to be a treatment of cancer. The absolute weight of a given ligand-associated therapeutic agent or combination thereof that is included in a unit dose can vary widely. For example, about 0.01 to about 2 g, or about 0.1 to about 500 mg, of at least one Siglec ligand-associated therapeutic agent can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of a therapeutic agent linked to a Siglec ligand can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the therapeutic agents of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid solutions, solid matrices, semi-solid pharmaceutical carriers, finely divided solid pharmaceutical carriers or combinations thereof, and then, if necessary, introducing or shaping the product into the desired delivery system.

When the therapeutic agents of the invention are prepared for oral administration, they are generally combined with a pharmaceutically acceptable carrier, diluent or excipient to form a pharmaceutical formulation, or unit dosage form. For oral administration, the therapeutic agents may be present as a powder, a granular formulation, a solution, a suspension, an emulsion or in a natural or synthetic polymer or resin for ingestion of the active ingredients from a chewing gum. The therapeutic agents may also be presented as a bolus, electuary or paste. Orally administered therapeutic agents of the invention can also be formulated for sustained release. For example, the therapeutic agents can be coated, micro-encapsulated, or otherwise placed within a sustained delivery device. The total active ingredients in such formulations comprise from 0.1 to 99.9% by weight of the formulation.

By "pharmaceutically acceptable" it is meant a pharmaceutical carrier, diluent, excipient, and/or salt that is compatible with the other ingredients of the formulation, and not deleterious to the recipient thereof. Note that the carriers associated with the Siglec ligands of the invention are distinct from the "pharmaceutically acceptable carrier" or a "pharmaceutical carrier" described in this section. Thus, a "pharmaceutically acceptable carrier" or a "pharmaceutical carrier" is a non-active ingredient that is not deleterious to the recipient thereof and that can solubilize or disperse the active ingredients to facilitate formulation of a convenient dosage form.

Pharmaceutical formulations containing the therapeutic agents of the invention can be prepared by procedures known in the art using well-known and readily available ingredients. For example, the therapeutic agent can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive pharmaceutical carriers such as kaolin and bentonite can be added. Lubricants such as talc, calcium and magnesium stearate, and solid polyethylene glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the therapeutic agents of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more of the therapeutic agents of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention can also take the form of an aqueous or anhydrous solution or dispersion, or alternatively the form of an emulsion or suspension or salve.

Thus, the therapeutic agents may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active agents and other ingredients may form suspensions, solutions, or emulsions in oily or aqueous vehicles, and may contain formulatory agents such as suspending, stabilizing and/or dispersing agents. Alternatively, the therapeutic agents and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more aqueous or organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

One of skill in the art may also add antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, the therapeutic agents are well suited to formulation as sustained release dosage forms and the like. The formulations can be so constituted that they release the active agent, for example, in a particular part of the vascular system or respiratory tract, possibly over a period of time. Coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic agents of the invention can be delivered via patches or bandages for dermal administration. Alternatively, the therapeutic agents can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. No. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid pharmaceutical carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the pharmaceutical carriers and/or diluents that are useful in the pharmaceutical formulations of the present invention include water and physiologically acceptable buffered saline solutions such as phosphate buffered saline solutions pH 7.0-8.0.

The active ingredients of the invention can also be administered to the respiratory tract. Thus, the present invention also provides aerosol pharmaceutical formulations and dosage forms for use in the methods of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984).

Therapeutic agents of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the therapeutic agents of the present invention specific for the indication or disease to be treated. Dry aerosol in the form of finely divided solid therapeutic agent that are not dissolved or suspended in a liquid are also useful in the practice of the present invention. Therapeutic agents of the present invention may be formulated as dusting powders and comprise finely divided particles having an average particle size of between about 1 and 5 μm, alternatively between 2 and 3 μm. Finely divided particles may be prepared by pulverization and screen filtration using techniques well known in the art. The particles may be administered by inhaling a predetermined quantity of the finely divided material, which can be in the form of a powder.

It will be appreciated that the unit content of active ingredient or ingredients contained in an individual aerosol dose of each dosage form need not in itself constitute an effective amount for treating the particular immune response, cancer or other disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, anti-cancer agents and the like, whether for the conditions described or some other condition.

Kits

The present invention further pertains to a packaged pharmaceutical composition such as a kit or other container for detecting, controlling, preventing or treating a disease. The kits of the invention can be designed for detecting, controlling, preventing or treating diseases such as those described herein (e.g., a lymphoma or leukemia).

In one embodiment, the kit or container holds a Siglec ligand for detecting disease and instructions for using the Siglec ligand for detecting the disease. The ligand can be attached to label or to a solid support.

In another embodiment, the kit or container holds a Siglec ligand for isolating cells that express a Siglec and instructions for using the Siglec ligand for isolating the cells. The ligand can be attached to bead or to a solid support.

In another embodiment, the kit or container holds a therapeutically effective amount of a pharmaceutical composition for treating, preventing or controlling a disease and instructions for using the pharmaceutical composition for control of the disease. The pharmaceutical composition includes at least one Siglec ligand of the present invention, in a therapeutically effective amount such that the disease is controlled, prevented or treated, wherein the Siglec ligand is attached to a therapeutic agent. The ligand-therapeutic agent can be provided in liquid form, powder form or other form permitting ready administration to a patient.

The kits of the invention can also comprise containers with tools useful for administering the compositions of the invention. Such tools include syringes, swabs, catheters, antiseptic solutions and the like.

The following examples are for illustration of certain aspects of the invention and is not intended to be limiting thereof.

EXAMPLE 1

Experimental Procedures

This Example describes some of the materials and methods used to analyze some of the aspects of the invention.

Antibodies and cell and mouse lines. CD22 null mice in C57B1/6 background were generated as described in Nitschke et al. Curr. Biol. 7: 133-43 (1997). Mice were maintained under pathogen free conditions at The Scripps Research Institute breeding facility and were used in accordance to the guidelines of the Institutional Animal Care Committee at the National Institutes of Health. BJAB, Daudi and RAJI cells were maintained in RPMI with 5% FCS or in RPMI supplemented with Neutradoma SP (Gibco), and 10 mM HEPES pH 7.0 for sera free conditions. Primary murine splenocytes were obtained from euthanized mice and then ground between two frosted glass slides and passed over a cotton plugged Pasteur to obtain single cell suspensions. Red blood cells were lysed by incubation in 0.15 M $NH_4Cl$, 10 mM $KHCO_3$, 0.1 mM EDTA, pH 7.2 for 5 min followed by washing with HBSS supplemented with 5 mg/ml BSA. Cells were kept on ice at all times. Primary human peripheral B cells were obtained from the Normal Blood Donor Service at The Scripps Research Institute. The blood was collected into tubes containing EDTA and then leukocytes were isolated by Lymphoprep. Following washing of the leukocytes, B cells were isolated using magnetic bead negative selection of non B cells (Miltiny Biotech). Antibodies used were from Pharmingen unless otherwise noted, anti-B220 (clone RA3-6B2), anti-CD22 (Pharmingen clone Cy34.1, and Southern Biotech, Birmingham, Ala., clone 2D6).

General procedure for 9-azido-9-deoxy-sialyloligosaccharide preparation. The appropriate mannose derivative (6AzManAc or 6AzManGc, 1 eq.), sodium pyruvate (3 eq.) and CTP (1.2 eq.) was dissolved in Tris-HCl (100 mM, 40 mL/mmol CTP), pH 9.5 containing $MgCl_2$ (20 mM) and pH adjusted to 8.6 with NaOH (1M). Neu5Ac-aldolase (NaI-311 (Toyobo), 400 U/mmol Mannose derivative) and *N. meningitidis* ST3Gal-CMPNeu5Ac synthetase fusion protein (20 U/mmol CTP) was added and the reaction was kept at 37° C. The pH was constantly monitored and adjusted with 1 M NaOH to pH 8.3-9.0 as needed. After 14 hrs the reaction was terminated by passing the mixture through a Prep/Scale-TFF Cartridge cellulose membrane filter MWCO 10K Da (Millipore, Bedford, Mass.). To the filtrate, oligosaccharide acceptor LacNAcβMCP (0.5 eq.), $MnCl_2$ (20 mM), alkaline phosphatase (500 U/mmol) and sialyltransferase (1 U/mmol acceptor) were added and the pH was adjusted to 7.0 with HCl (IM). After 14 hrs the product was purified by repeated size exclusion chromatography (Sephadex G15, 2.5×160 cm, equilibrated in 5% n-BuOH) and compounds were isolated in yields typically of about 0.2-0.3 g (75-85%) with a purity > 90% as analyzed by silica gel thin layer chromatography (eluent: ethylacetate:methanol:acetic acid:water; 6:3:3:2 (by volume)) and NMR (Blixt et al. J. Biol. Chem. 278: 31007-19 (2003)).

General Procedure for BPC-acylation. Each of the sialoside derivatives 9-Azido-9-deoxy-N-acetyl neuraminic acid and 9-Azido-9-deoxy-N-acetyl neurmaminic acid α2,6 galactose β1-4 N-acetylglucosamine (1 eq., 25-50 μmol) were dissolved in methanol-water (9:1 by volume, 1-2 mL) and hydrogenolysed over Pd/C (10%, 20-30 mg) in a hydrogen atmosphere at room temperature. Insoluble catalyst was removed by centrifugation and diisopropylethylamine (4 eq.) and N-biphenyl-4-carbonyl chloride (2 eqv.) was added to the supernatant. When the reaction showed complete reduction to amine (analyzed by silica gel thin layer chromatography, eluent: ethylacetate:methanol:acetic acid:water; 10:3:3:2, by volume), the mixture was concentrated, reconstituted in water and applied to a silica reversed phase SepPak-C18 column (10 g size) pre-equilibrated in water. The compounds were eluted with a 50 mL gradient of methanol:water (0-80%) and appropriate fractions containing the product were pooled, concentrated and further purified by gel filtration chromatography (Sephadex G15, 1×70 cm, equilibrated in 5%-n-BuOH). Fractions containing the BPC-derivative were pooled and lyophilized to generate a white fluffy solid (65-75%).

The above biphenyl-saccharides as well as NeuAcα2-6Gal β1-4 N-acetylglucosamine and NeuGcα2,6Gal β1-4 N-acetylglucsoamine were conjugated to low high molecular weight PAA as described in Shilova et al. (Glycoconj. J. 43-51 (2005)).

General Procedure for BPA-acylation: Each of the sialoside derivatives 9-Azido-9-deoxy-N-acetyl neuraminic acid and 9-Azido-9-deoxy-N-glycolyl neurmaminic acid α2,6 galactose β1-4 N-acetylglucosamine (1 eq., 25-50 μmol) were dissolved in methanol-water (9:1 by volume, 1-2 mL) and hydrogenolysed over Pd/C (10%, 20-30 mg) in a hydrogen atmosphere at room temperature. Insoluble catalyst was removed by centrifugation and to the supernatant a pre-mixture of diisopripylcarbodiimide (1.2 eq.) and N-biphenyl-4-acetic acid (1.2 eq.) in methanol was added. After 30 minutes at room temperature, the reaction was diluted with 10 volumes of water and applied onto a silica reversed phase SepPak-C18 column (10 g size) pre-equilibrated in water. The compounds were eluted with a gradient of methanol:water (0-80%) over 50 mL and appropriate fractions containing the product were pooled, concentrated further purified by gel filtration chromatography (Sephadex G15, 1×70 cm, equilibrated in 5%-n-BuOH). Fractions containing the BPC-derivative were pooled and lyophilized to generate a white fluffy solid (65-75%).

ELISA inhibition assays: For inhibition assays, high binding 96 well microtiter plates (Corning Costar) were coated with neutravidin by incubation with 50 ul of 1 mg/ml Neutravidin (Pierce Biotechnology) in 50 mM Na bicarbonate pH 9.5 overnight at 4° C. The wells were then washed with PBS and blocked with PBS containing 5 mg/ml BSA for 1 hr at 37° C. Fifty microliters of a selected biotinylated sialoside (0.33 uM) was added to each well, and allowed to bind for 1 hr at room temperature. The sialoside was then allowed to bind for 1 hr at 37° C. and the wells were washed.

The CD22-Fc chimera employed was produced as described in Blixt et al. (J. Biol. Chem. 278: 31007-19 (2003)) and diluted to 0.1 mg/ml into HBSS (with 5 mg/ml BSA and 1 mM EDTA). An F(ab')2 Fragment Goat anti-Human IgG (Jackson Immunoresearch) (0.066 mg/ml) was mixed and allowed to complex with Peroxidase conjugated $F(AB')_2$ Fragment Rabbit anti Goat F(ab')2 specific (0.010 mg/ml) for 15 min. CD22-Fc (1.5 ml) was added to 1 ml of the pre-complexed solution and allowed to further associate with complexes in that solution for 15 min. The inhibitor of interest was diluted into HBSS. Twenty-five microliters of the inhibitor and 25 ul of the CD22Fc complex were added to each well and the plates were incubated for 30 min at 37° C. The plates were then washed 4 times with 200 ul of HBSS. Wells were developed with 50 ul of 1 mg/ml OPD (Sigma), 0.03% $H_2O_2$ in 50 mM phosphate/citrate, pH 5.0. The reaction was stopped with 50 ul of 2.5 M $H_2SO_4$ and the optical density at 450 nm ($OD_{450}$) was measured.

For polyacrylamide (PAA) ELISA-type assays cells were coated with 1 ug Protein A diluted in 50 mM Na bicarbonate pH 9.0 overnight at 4° C., washed and blocked with HBSS/B for 1 hr at 37° C. CD22-Fc diluted into HBSS/B (50 ul) was added to each well at selected concentrations and allowed to adhere for 1 hr at 37° C. before washing twice with 200 ul HBSS/B. Selected amounts of the PAA probe were diluted to HBSS/BSA and 50 ul aliquots of these dilutions were added to each well. Binding was allowed to proceed for 2 hr at 37° C. Wells were then washed three times with 200 ul HBSS/B. Fifty microliters of Alkaline phosphatase conjugated-streptavidin (Sigma) was added to each well, the plates were incubated for 1 hr at 37° C. and washed three times with 200 ul HBSS/B. Wells were developed with pNPP developing solution (Sigma) and read at $OD_{405}$.

PAA probe binding to cells. B cells or splenocytes were resuspended in HBSS supplemented with 5 mg/ml BSA (HBSS/B) at a cell density of $2 \times 10^6$ cells/ml and kept on ice at all times. Cells were first unmasked by treatment with *A. ureafaciens* sialidase (200 mU/ml) for 30 min at 37° C. and then washed 3×1 ml to remove any remaining sialidase. The cells (100 ul) were then incubated with the PAA probe (1 ug) and a selected sialoside inhibitor for 1.5 h on ice. Cells were then washed with 1 ml of HBSS/B. Bound probe was detected by reaction with streptavidin-CyChrome or streptavidin-PE (Pharmingen 1 ul/tube) for 45 min on ice, washing and observation with a Facscalibur flow cytometer. In some cases, 0.2 ul of anti-B220 was added to the cells during the streptavidin labeling to detect B cells.

Cell binding to immobilized PAA probes. High binding 96 well microtiter plates (Corning Costar) were coated with neutravidin by incubation with 50 ul of 1 mg/ml Neutravidin (Pierce Biotechnology) in 50 mM Na bicarbonate pH 9.5 overnight at 4° C. The wells were blocked with HBSS/B for 1 hr at 37° C. and selected amounts of PAA probe (diluted into HBSS/B) was added to each well. The plates were incubated for 1 hr at 37° C. Wells were then washed three times. Meanwhile, cells were labeled with CMFDA by incubating at $1 \times 10^6$ cells in media supplemented with 1 uM CMFDA. Following washing, $1 \times 10^6$ labeled cells were added to the probe coated wells and allowed to adhere for 30 min at 37° C. For detachment, plates were carefully submerged in a vat of PBS and then inverted, cells were allowed to detach for 20 min before righting the plate and removing the PBS. Cell adhesion was then quantified by fluorescence (excitation 488 nm, emission 530 nm).

Cell Adhesion to PAA probes and Magnetic Beads. Murine splenocytes were isolated as described above and resuspended at a cell density of $2 \times 10^7$ cells/ml in HBSS/B. The PAA probe (20 ug) was added to 1 ml of the cell suspension. The plate was incubated for 2 hr on ice. Cells were then washed with 1 ml HBSS/B and resuspended in 90 ul of HBSS/B solution. Ten microliters of streptavidin-coated beads (Miltinyi Biotech) were then added to the cell suspension. After incubation at 4° C. for 30 min, the cells were washed with 1 ml of HBSS/B, resuspended in 500 ul of HBSS/B and applied to a pre-washed MS magnetic column (Miltinyi Biotech). The column was washed three times with 500 ul HBSS/B, then removed from the magnet and the bound cells were eluted with 1 ml of HBSS/B. Cells were then stained with anti-B220 as above and analyzed by flow cytometry. Dynal microbeads were washed with HBSS/BSA and then coated with polyacrylamide (PAA) probe of interest using 6 ug probe and 5 ul of magnetic beads in 500 ul of HBSS/B. After 1 hr incubation at room temperature the beads were washed twice to remove any unbound probe, and were added to the cells to form a 10:1 beads:cell suspension. The beads were allowed to bind to the cells for 1 hr at 4° C. with end-over-end rotation and then were washed two times before fixation onto a glass slide and visualization by microscopy.

Measurement of probe internalization. BJAB cells ($2 \times 10^6$ cell/ml) were labeled with the PAA probe and streptavidin as above. Following staining, aliquots of 100 ul of the cell suspension were placed on ice or at 37° C. for selected periods of time. After incubation, the cells were washed with 400 ul of RPMI pH 2.0 to remove surface-bound streptavidin, and then washed twice with 1 ml of HBSS/B. For potassium depletion, cells were first washed with DMEM:water (1:1), then incubated with potassium-depleted media at 37° C. for 1 h. After cooling, the probe was added and incubated as above but with either HBSS/BSA or in potassium-depleted media supplemented with BSA for 1.5 h. Cells were then washed and stained with streptavidin as above.

Probe mediated cell killing, Cells were labeled with the PAA probe as above and then further incubated with 3 ug/ml of streptavidin-ZAP saporin conjugate (Advanced Targeting Systems, San Diego, Calif.). After labeling with the streptavidin-ZAP the cells were washed and plated at a density of $0.2 \times 10^6$ cells/well in a total volume of 200 ul of RPM/100% FCS/penicillinstreptomycin, and cultured for 48 h. Cells were then harvested and viable cells quantified by propidium iodide staining and flow cytometry.

EXAMPLE 2

Figure 2A:
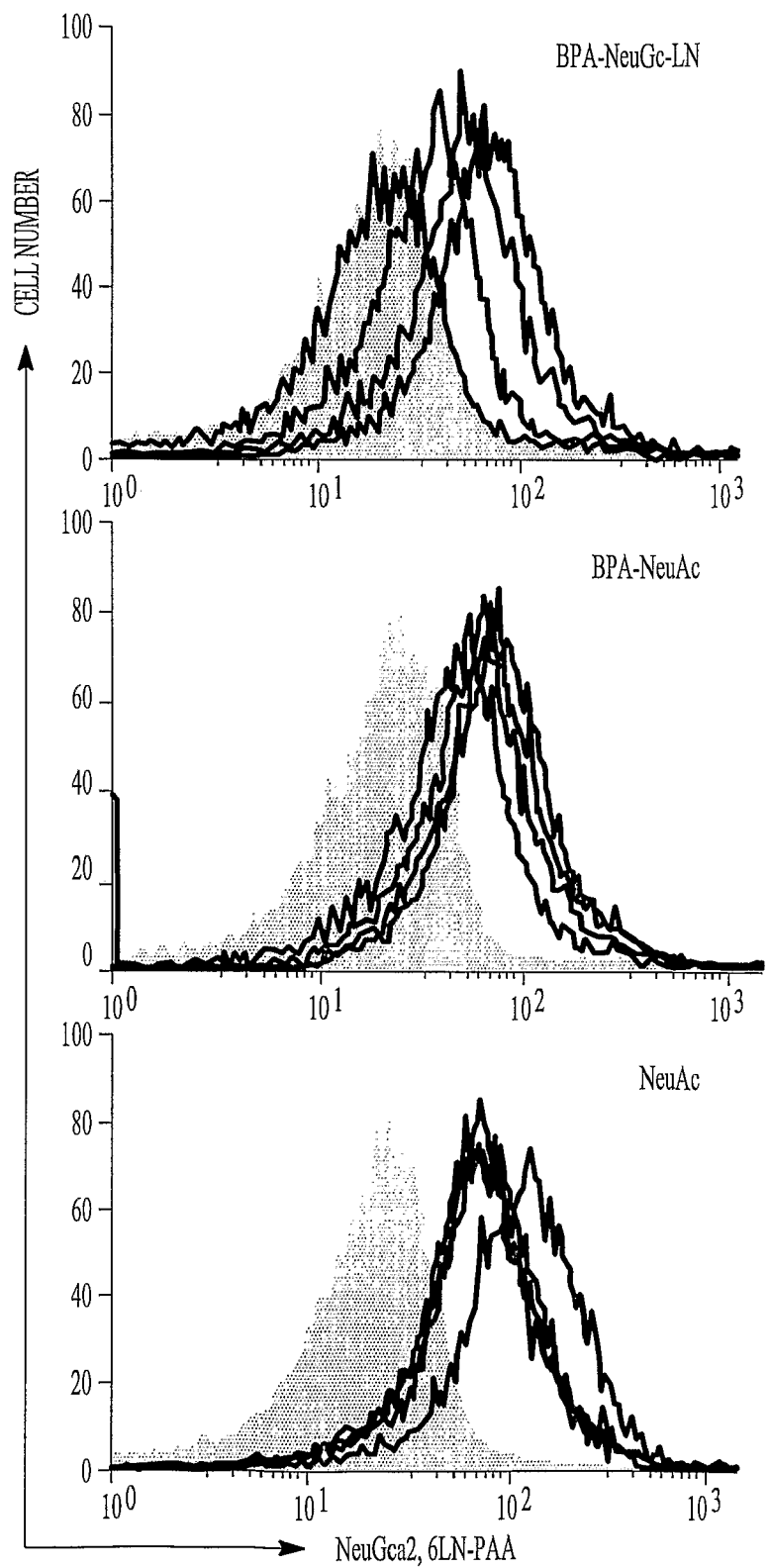
FIG. 2A-B illustrate inhibition of multivalent sialoside probe binding to cell surface CD22 by potent biphenyl (BP) derivatives.
Figure 2B:
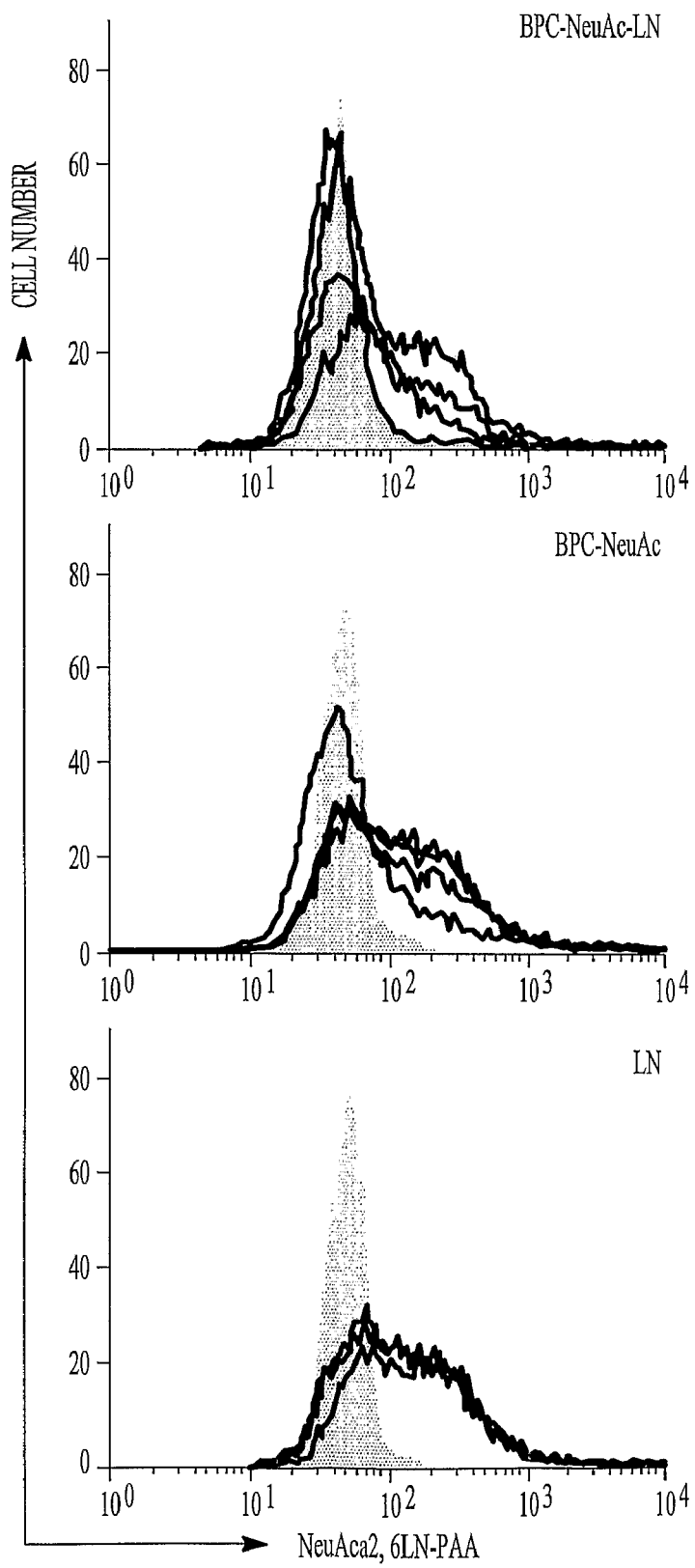

Siaα2,6Gal Glycans Derivatized at Position 9 with a Large Hydrophobic Group and Having a Neutral Sugar Bind to CD22 with Improved Affinity This Example demonstrates that sialosides with biphenyl groups linked in the to position 9 of the sialic acid have improved affinity for binding to CD22, especially when sialic acid is linked to a neutral saccharide such as N-acetyllactosamine in an α2,6 configuration.

Modeling studies of CD22 indicated a hydrophobic pocket in its binding site next to the 9-position carbon on the sialic acid (Zaccai et al. Structure (Camb) 11: 557-67 (2003). Accordingly, sialic acids with bulky biphenyl groups at that position were observed to be inhibitors of CD22 (Kelm et al. J. Exp. Med. 195: 1207-13 (2002)). To increase the affinity, sialosides were synthesized containing biphenyl groups at the 9 position of a sialic acid conjugated α2,6 to N-acetyllactosamine (FIG. 1A). The relative inhibitory potency (rIP) of these inhibitors was determined by measuring the inhibition of human or murine Siglec binding to immobilized NeuAcα2,6LacNAc (NeuAc-LN, because NeuAc is found in humans) or NeuGcα2,6LacNAc (NeuGc-LN, because NeuGc is found in mice)(Table 1).

TABLE 1

Inhibitory potency of Sialosides

| | IC 50 value in μM | | rIP | |
|---|---|---|---|---|
| | hCd22 | mCd22 | hCd22 | mCd22 |
| NeuAc | >2000 | >2000 | <0.1 | <0.1 |
| NeuAc-LN | 220 | >2000 | 1 | <0.1 |
| NeuGc-LN | 260 | 221 | 0.85 | 1 |
| BPA-NeuAc | 50 | 220 | 4.4 | 1 |
| BPC-NeuAc | 35 | 1500 | 6.3 | 0.15 |
| BPC-NeuAcLN | 2.2 | 242 | 100 | 0.91 |
| BPA-NeuGc-LN | 2.1 | 0.8 | 100 | 276 |

As shown in Table 1, while no inhibition was observed with the NeuAc alone, attachment of N-acetyllactosamine to NeuAc (NeuAc-LN) generated an inhibitor that inhibited human Siglec binding to immobilized NeuAcα2,6LacNAc at concentrations of 200 μM, which is similar to reports suggesting that the assay IC50 values are close to Ki values (Blixt et al., J. Biol. Chem. 278: 31007-19 (2003)). Use of the biphenyl group with NeuAc, to generate BPA-NeuAc and BPC-NeuAc, increased the inhibitory potency to 50 μM and 35 μM, respectively, when human CD22 was used. When mouse CD22 was used, BPA-NeuAc and BPC-NeuAc exhibited an inhibitory potency of 220 μM and 1500 μM, respectively.

The effects of using biphenyl and a LacNAc neutral core were additive as sialosides containing both of these groups at 9 position exhibited improved IC50 values of 2 μM for BPC-NeuAcLN with human CD22 (hCD22), or 1 μM for BPA-NeuGc-LN with mouse CD22 (mCD22). Thus, BPC-NeuAcLN and BPA-NeuGc-LN appear to compete for and bind with good affinity to CD22 (Siglec).

EXAMPLE 3

Multivalent BPC-NeuAc-LN and BPA-NeuGc-LN Bind to and Internalize within CD22-Expressing B Cells This Example demonstrates that multivalent sialosides, each with a large hydrophobic group at position 9 of a sialic acid that is linked to a neutral sugar, not only bound to native B cells but also were internalized within those B cells.

Inhibition of Probe-Binding to B cells by Sialic Acid Inhibitors. In initial studies, B cells were pretreated with sialidase to remove sialic acids and therefore unmask CD22. This was done because while B cells express CD22, they also have a high density of sialic acid-containing glycans associated with their cell surfaces. These "cis" glycan ligands can mask binding of sialic acid ligands provided in "trans." After treatment with sialidase, inhibition of B cell binding by monovalent BPC-NeuAc-LN and BPA-NeuGc-LN was detected for multivalent polyacrylamide (PAA) sialoside probes derivatized with NeuAc-LN (hCD22) or NeuGc-LN (mCD22) (FIG. 2). In particular, FIG. 2 shows that when the LN neutral core and the biphenyl group were present at position 9, an additive effect was observed, allowing for complete inhibition of the probe binding (FIG. 2). In contrast, no inhibition was observed at concentrations of up to 2 mM with the other sialic acid derivatives.

Because of the high Kd values, stable binding of carbohydrate interactions is highly dependent upon the valency of the sialoside-lectin interaction. Although multivalency can be achieved through the use of a variety of different carriers, the well-established polyacrylamide (PAA) backbone was used for initial studies. In this system sialosides were pendently attached along with biotin or fluorescent groups to allow for easy detection of the probes.

Figure 3A:
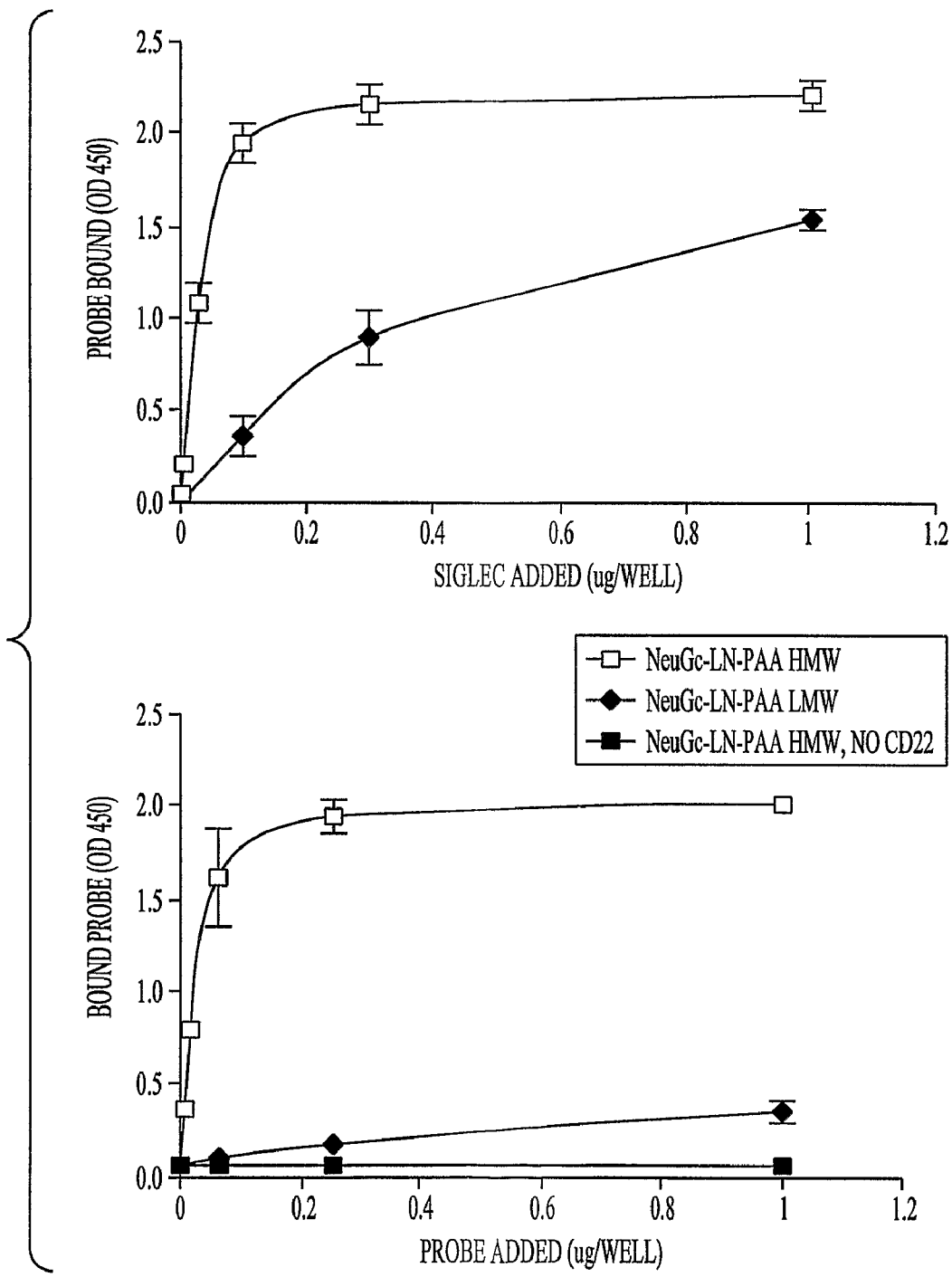
FIG. 3A-E graphically illustrate that high-valency polyacrylamide (PAA) probes have increased avidity and sensitivity for mouse and human CD22.
Figure 3B:
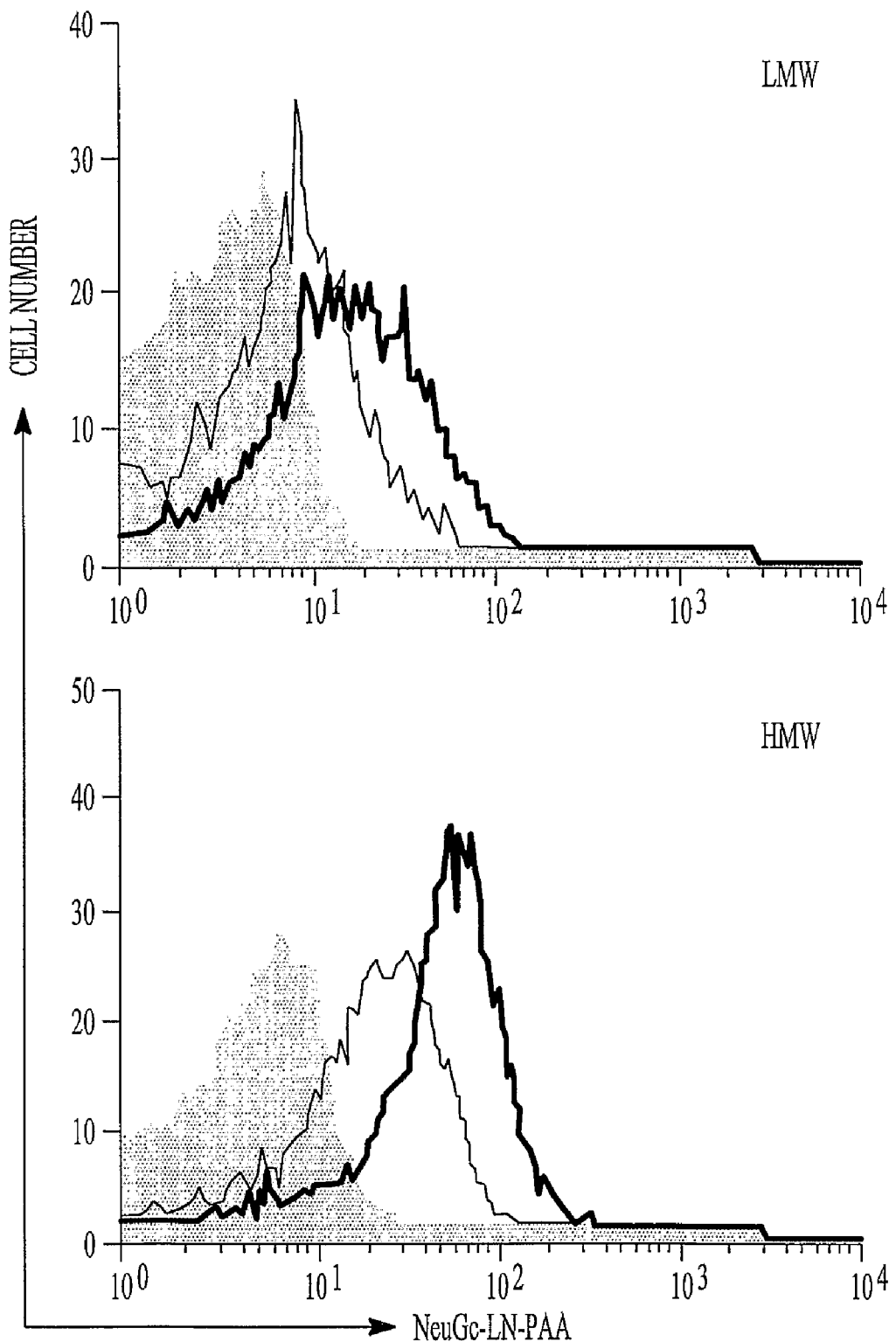

As shown in FIG. 3A, comparison of two PAA probes with different molecular weights (HMW≧1000 kDa and LMW≈30 kDa), each carrying the NeuGc-LN ligand, resulted in significantly higher binding of the high molecular weight (about 1500 kDa) construct as compared with the low molecular weight (about 30 kDa) construct. Maximal binding was observed at greater than 10-fold lower concentrations of the high molecular weight form. Although increased nonspecific binding of high molecular weight PAA derivatives to plastic has been observed previously, the binding reported here was specific to CD22 because no increase in nonspecific background (e.g. no nonspecifically immobilized Siglec) was observed. In addition, the higher molecular weight probe had increased sensitivity to CD22 expressed on cell surfaces. When murine splenic B cells were treated with increasing amounts of A. ureafaciens sialidase to unmask increasing amounts of cell-surface CD22, both probes gave detectable levels of binding following unmasking of CD22, but the high molecular weight probe was consistently more sensitive and exhibited a greater signal over background (FIG. 3B).

Figure 3C:
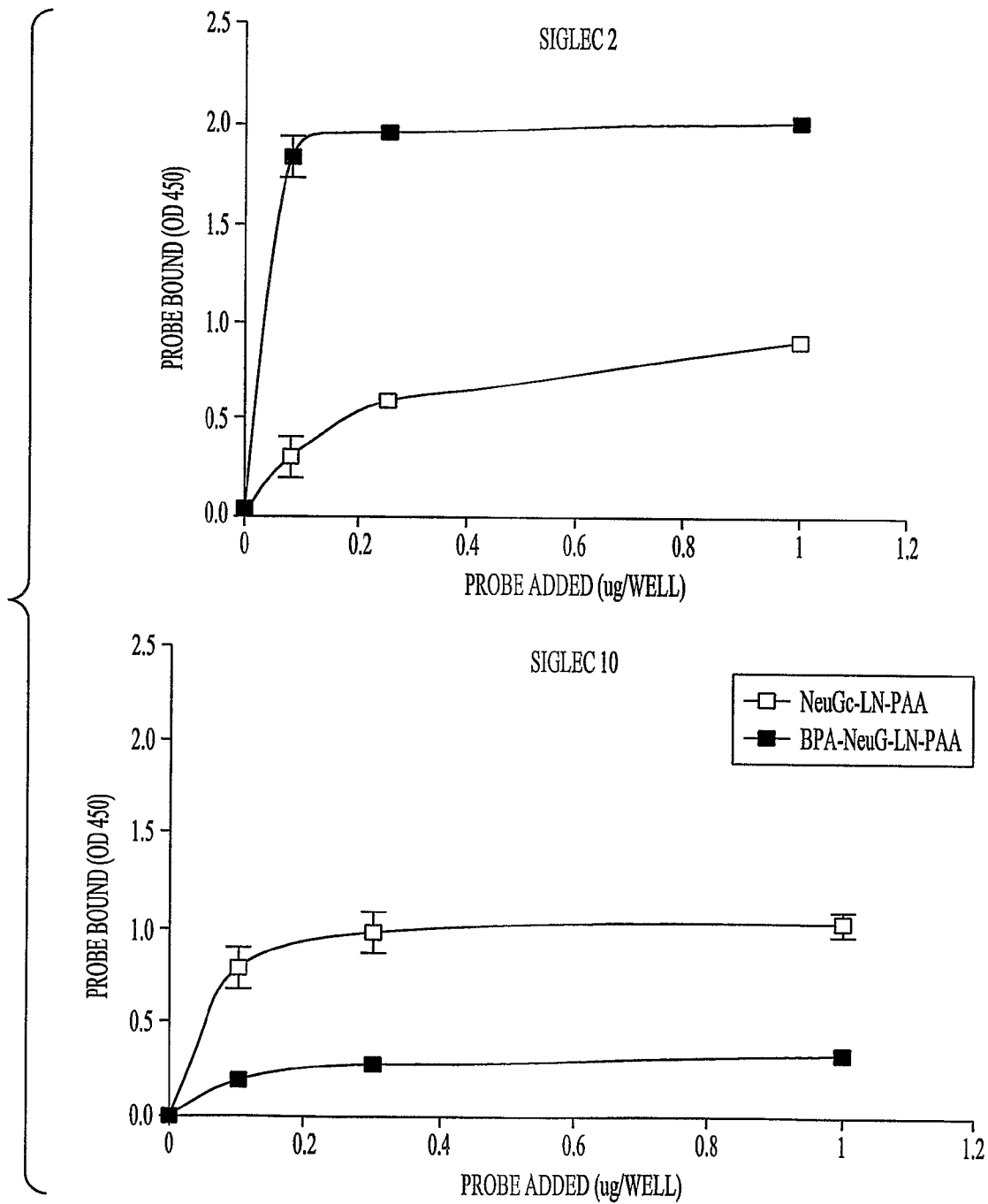

High-Valency Probes Exhibit Improved Affinity for CD22. Building on the binding studies described above, polyacrylamide (PAA) probes containing the BPA-NeuGc-LN or BPC-NeuAc-LN sialosides were synthesized and tested for binding to CD22. FIG. 3C shows that the high molecular weight BPA-NeuGc-LN-PAA probe achieved maximum binding to immobilized mCD22 at 10-fold lower concentrations compared to the same molecular weight NeuGc derivative. Siglec 10 another B cell lectin, however, binds well to the NeuGc-LN glycan, but in contrast to CD22, only weakly to the high molecular weight BPA derivative.

Figure 3D:
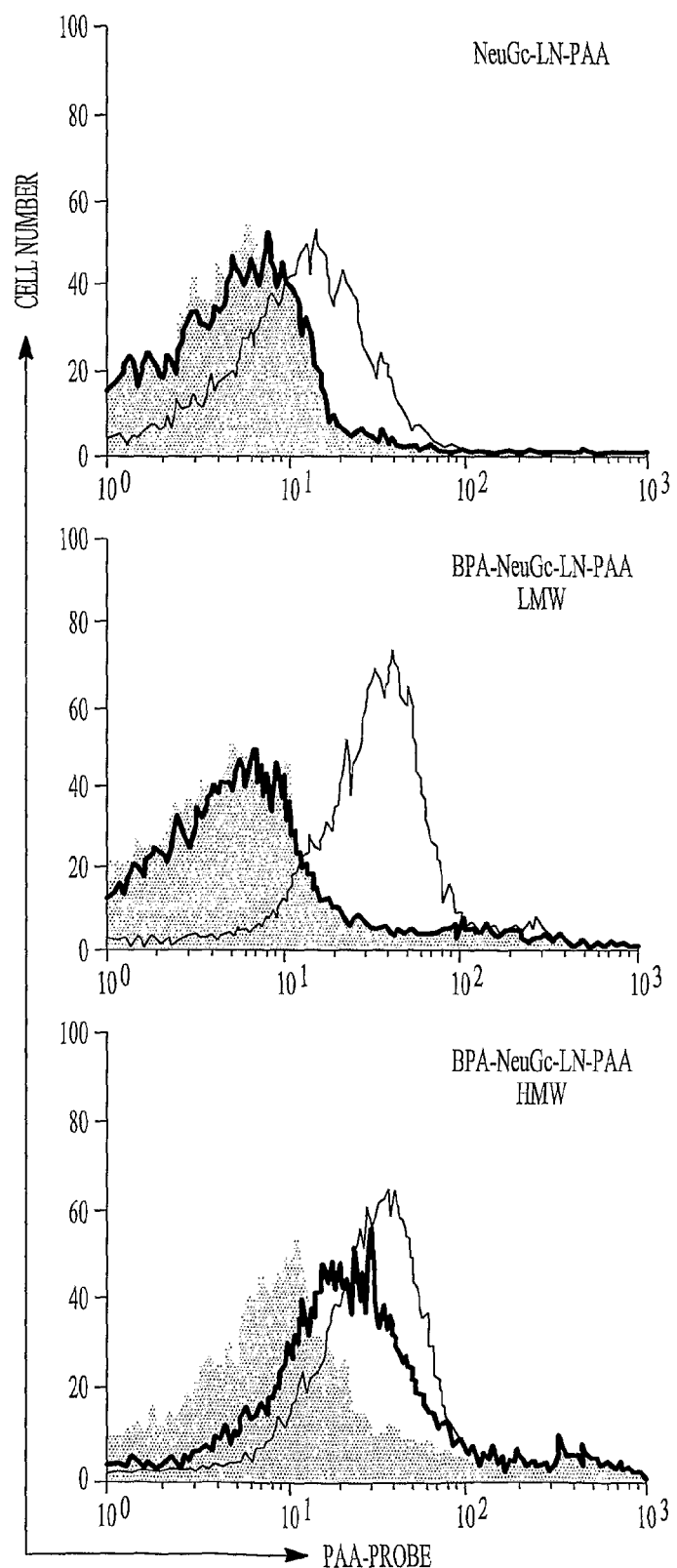

BP derivatives compete with cis ligands on B cells to bind to 'masked' CD22. The BPA-NeuGc-LN-PAA probes were assayed for their ability to bind to CD22 expressed on cells as compared to PAA probes without the biphenyl (BPA) group, (NeuGc-LN-PAA). Primary murine B cells were harvested from wild type and mice with a CD22 null mutation. An aliquot of these B cells were treated with A. ureafaciens sialidase to unmask CD22. A control aliquot of these B cells were untreated with A. ureafaciens sialidase. Binding by NeuGc-LN-PAA, BPA-NeuGc-LN-PAA, or the high molecular weight BPA-NeuGc-LN-PAA was measured. While all probes bound to the wild-type sialidase-treated B cells, the BPA derivatives, significantly more of both the 30 kDa and the high molecular weight PAA probes bound than did the NeuGc control (FIG. 3D). None of the probes bound to CD22 negative cells.

Figure 3E:
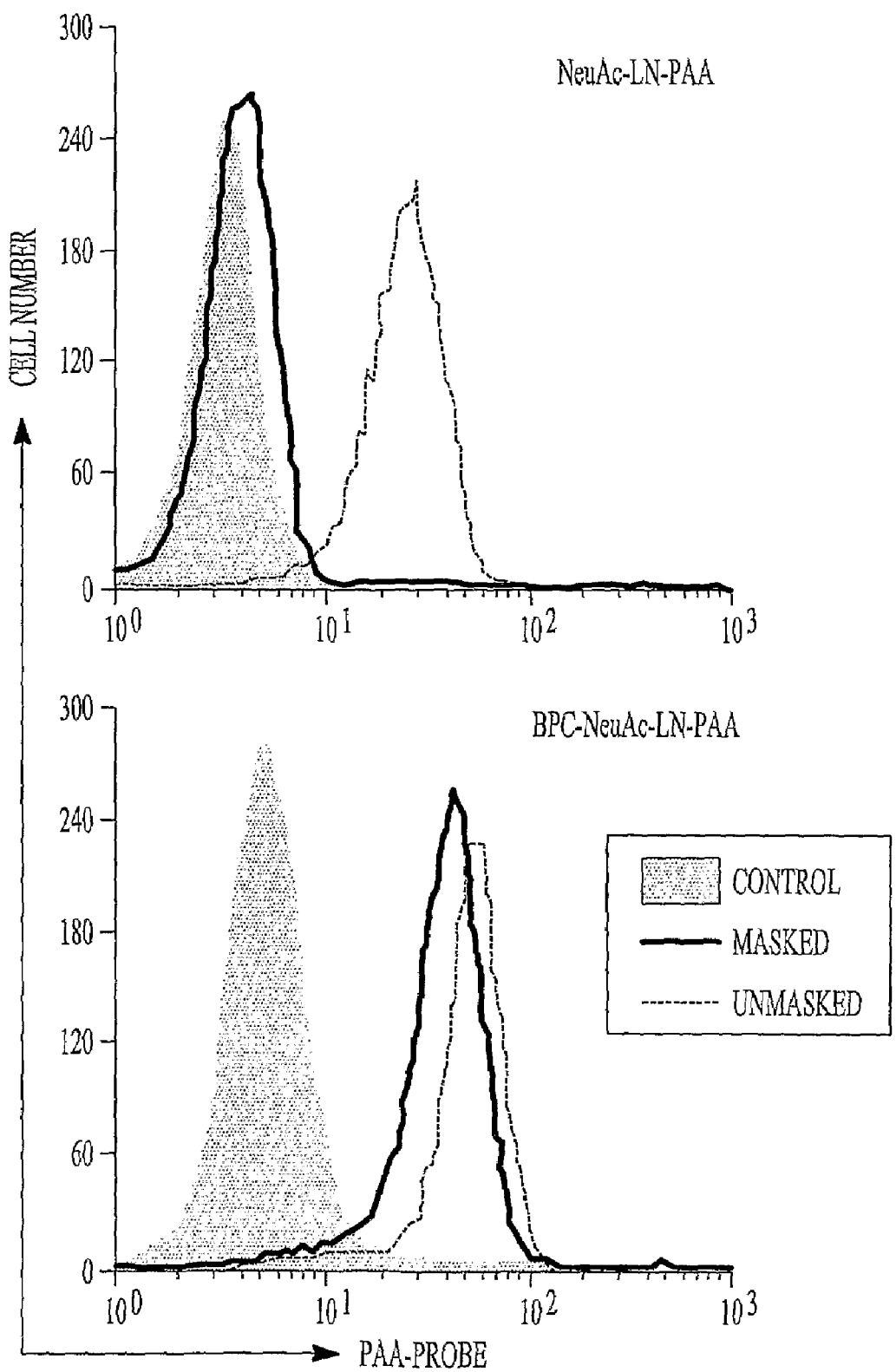

Significantly, however, while the NeuGc-LN and the 30 kDa BPA-NeuGc-LN-PAA probes only bound to the 'unmasked' CD22, the high molecular weight BPA-NeuGc-LN-PAA probe bound to non-treated or 'masked' CD22 (FIG. 3D). The probe binding to 'masked' CD22 was not reflective of a particular subpopulation of cells with low levels of cis ligands because the entire cell population shifted. Moreover, staining with the lectin SNA was similar to that of cells that did not support NeuGc-LN-PAA probe binding (data not shown). Similarly, human B cell lines also supported binding of the high molecular weight BPC-NeuGc-PAA with 'masked' native CD22 (FIG. 3E). These data indicate that the combination of a high-valency probe that includes a sialoside derivatized with a hydrophobic moiety generates a CD22 ligand with high enough avidity to compete with the cis ligands that normally mask CD22.

High Molecular Weight BP-Sialosides are Specific for B cells. To further ascertain the strength and specificity of the BPA/(C)-PAA derivatives, the ability to support cell adhesion was evaluated. The human BJAB cell line was pretreated with or without sialidase to unmask CD22 and cells were added to wells that had been pre-coated with neutravidin and either BPC-NeuAc-LN-PAA or NeuAc-LN-PAA. After allowing unbound cells to detach by inversion in a vat of PBS, the bound cells were detected using fluorescence. No cells bound to microtiter plates in the absence of the probes, and only unmasked B cells bound to NeuAc-LN-PAA coated wells. BPC-NeuAc-LN-PAA derivatives, however, were able to support binding to both unmasked and masked B cells (data not shown).

Figure 4A:
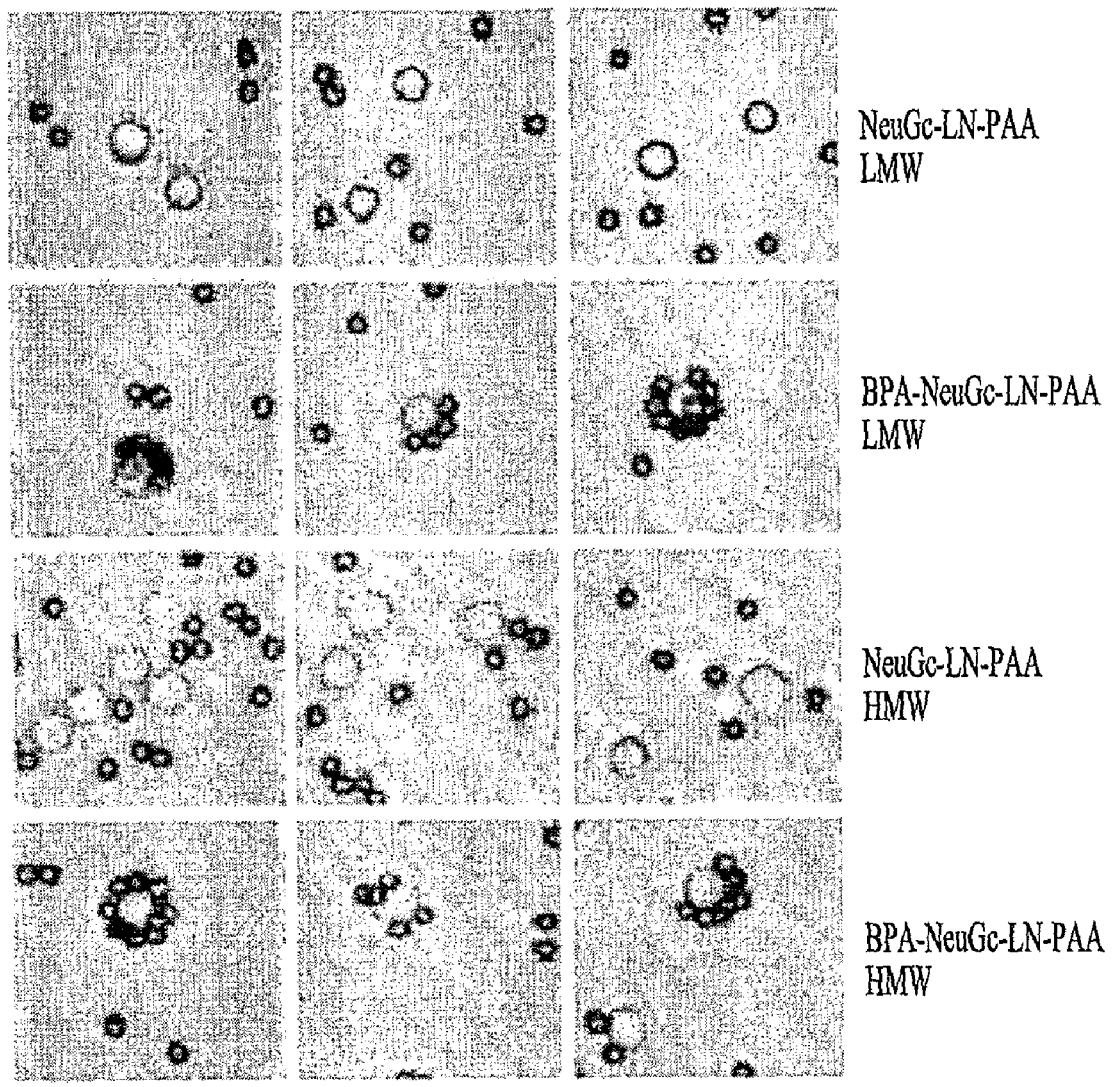
FIG. 4A-C illustrates that high-molecular weight (HMW), biphenyl-derivatized sialic acid glycans bind to native B cells and can be used to purify those B cells. For FIG. 4A, the indicated PAA probe was immobilized onto streptavidin coated magnetic beads, washed, and then added to purified murine B cells. The beads were allowed to bind to the cells for 30 min then exposed to magnet and fixed onto a glass microscope slide. For FIG. 4B-C, murine splenocytes from wild type and CD22 null mice were incubated with BPA-NeuGc-LN for 1.5 h, washed, and then incubated with biotinylated magnetic beads. The cells and beads were applied to a magnetic column and then washed and eluted. Eluents were counted and stained with anti-B220 and anti-CD22 to determine B cell populations. Data are representative of two distinct experiments.

Similarly, magnetic beads coated with the BPA probes were able to bind to B cells. Streptavidin coated magnetic beads were first coated with one of the NeuGc-LN-PAA, BPA-NeuGc-LN-PAA, High Molecular Weight NeuGc-LN-PAA, or the High molecular weight BPA-NeuGc-LN-PAA compounds. The coated beads were then incubated with cells. Cells not bound to the beads were removed by exposing the solution to a magnet and then washing the magnetized area. Irrespective of the degree of valency the NeuGc-LN-PAA coated beads were unable to bind to the magnetic beads. In contrast, the high molecular weight BPA-NeuGc-LN-PAA derivatives bound to cells (FIG. 4A). Significantly, the 30 kDa BPA-NeuGc-LN-PAA when immobilized onto beads was also able to support magnetic bead binding, but only if BPA-NeuGc-LN-PAA was first coated onto the beads. If, however, the cells were first incubated with the probes and then incubated with the streptavidin-coated magnetic beads, only the high molecular weight BPA-NeuGc-LN-PAA was able to support bead binding to the non-treated or 'masked' B cells (data not shown).

Figure 4B:
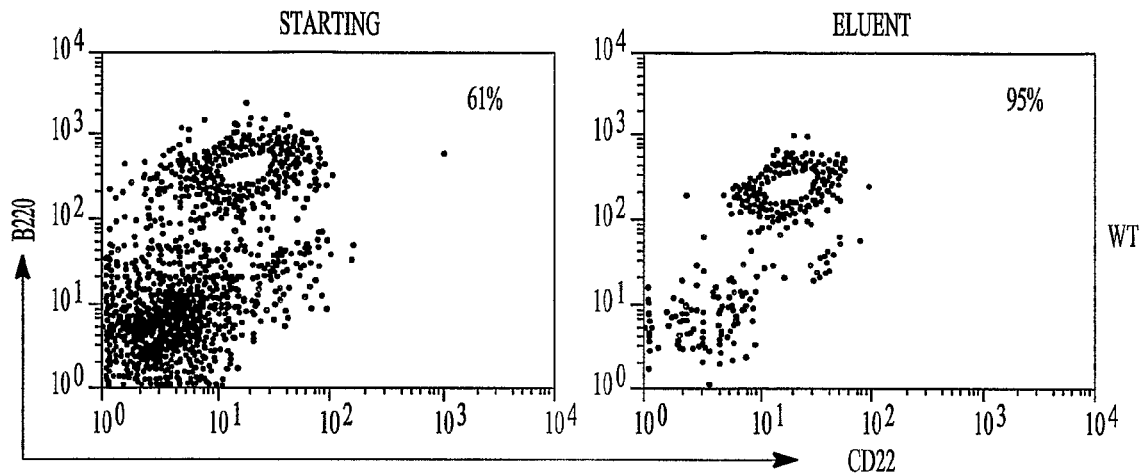
Figure 4C:
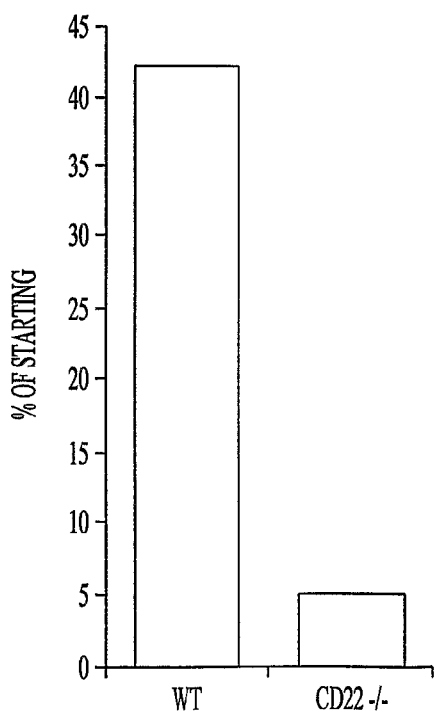

Biotinylated antibody coated cells can be purified using magnetic beads and a magnetized column. Therefore, tests were performed to ascertain if primary splenocytes from wild type and CD22-null mice would bind to the high molecular weight BPA-NeuGc-LN-PAA probe when streptavidin-coated micromagnetic beads were added. After incubating the cells with high molecular weight BPA-NeuGc-LN-PAA, streptavidin-coated magnetic beads were added and the mixture was incubated. This mixture was then placed in front of a magnet, washed, and then eluted. Elution from beads mixed with wild type cells resulted in greater than 90% enrichment for B220+B cells compared with 60% of the starting splenocyte population, and 40% recovery of the starting B cell populations (FIGS. 4B and 4C). In contrast, few CD22-null cells stuck to the column and those that did resulted from nonspecific binding because the eluted population was similar to the starting population.

Figure 5A:
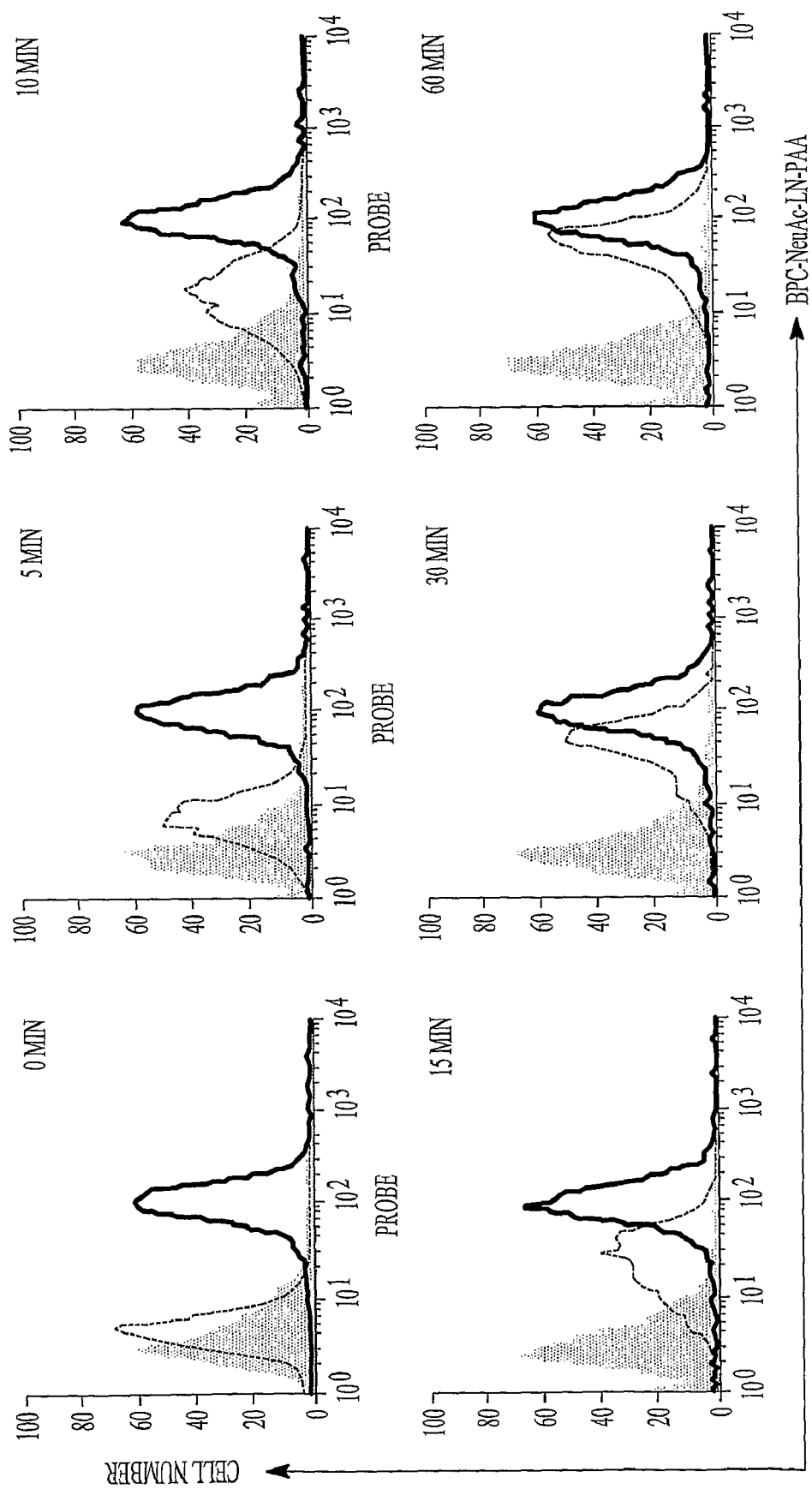
FIG. 5A-B illustrates clathrin-mediated uptake of high molecular weight biphenyl-Sialic acid derivatives. To generate the data shown in FIG. 5A, BJAB cells grown in the presence of sera and supplemented with NeuAc were incubated with the high molecular weight BPC-NeuAc-LN-PAA (light and heavy lines) or LN-PAA (Shaded) probes for 1.5 h on ice, followed by CyChrome labeled streptavidin for 45 min on ice. After washing, the cells were then incubated at 37° C. for the indicated period of time. Following this incubation, cells were washed with HBSS/BSA (shaded peak and heavy line) or RPMI pH 2.5 (light line). Bound or internalized probe was detected by flow cytometry. To generate the data shown in FIG. 5B, cells were washed with RPMI:Water (1/1) and then incubated for 1 hr in media with or without potassium. After pre-chilling on ice, cells were incubated in the corresponding media with the BPC-NeuAc-LN-PAA probe and then internalization was measured as above. Data are the average of two independent experiments.

Endocytosis of PAA probes. Antibody-mediated crosslinking of CD22 results in its endocytosis (Leonard et al. Clin. Cancer Res. 10: 5327-34 (2004); Leonard et al. J. Clin. Oncol. 23: 5044-51 (2005); and Coleman et al. Clin. Cancer Res. 9: 3991S-3994S (2003)). Similarly, the ability for B cells to endocytose the PAA probes was determined. Cells were incubated with the fluorescent probe and allowed to internalize for selected time periods at 37° C. The remaining cell surface PAA was then removed by a brief low pH wash (RPMI, pH 2.5). The remaining fluorescence as measured by flow cytometry as a measure of the amount of internalized probe. Significant internalization of the high molecular weight BPC-NeuAc-LN-PAA probe occurred within the first 10 min of incubation (FIG. 5A). Internalization of the high molecular weight BPC-NeuAc-LN-PAA probe reached a maximum at 30 min (FIG. 5A). In contrast, no internalization of the LN-PAA probe was observed (data not shown).

Figure 5B:
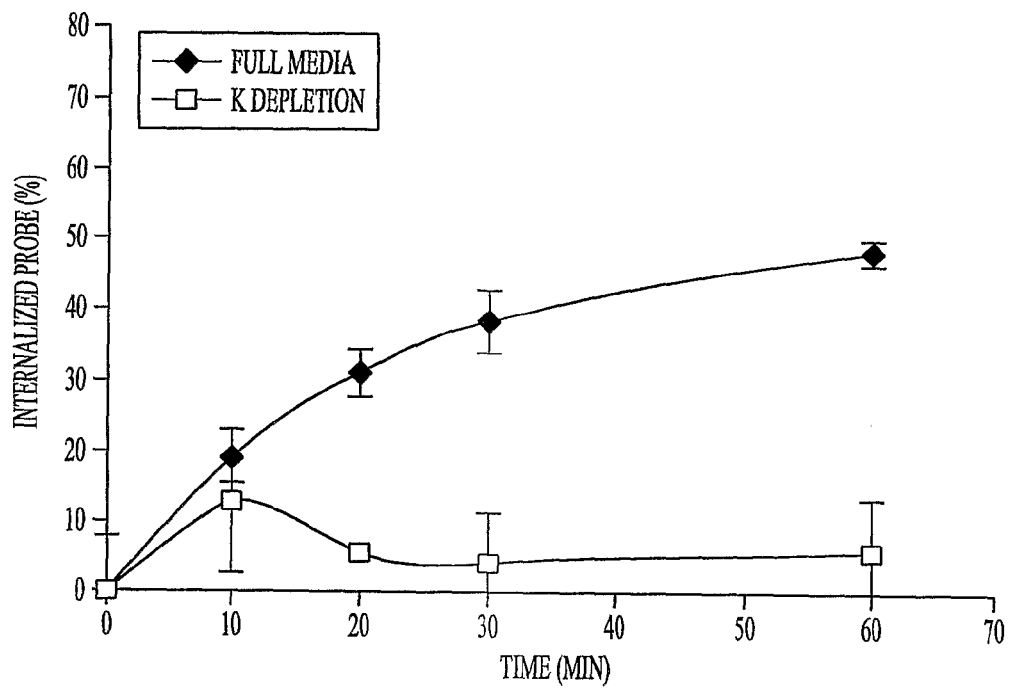

CD22 associates with the AP-50 adaptor molecule, which is part of the clathrin complex. Accordingly, probe endocytosis may be clathrin mediated because potassium depletion, which blocks clathrin formation, abolished internalization (FIG. 5B). However, nystatin, which inhibits caveolin, did not inhibit and may actually have increased probe internalization. Caveolin is a small molecular weight protein shown to be associated with the caveolar plasma membranes.

Targeting and killing of R cells with sialoside probes. Antibody-mediated targeting has, in some instances, provided a useful approach to target chemotherapeutic agents to leukemias and lymphomas that may otherwise be resistant to chemotherapy. Conjugation of these antibodies with toxins or radioisotopes allow for the targeting of the agent in a cell type specific manner.

To test whether the present sialosides could provide a similar utility, the high molecular weight BPC-NeuAc-LN-PAA probe was conjugated to saporin toxin, a potent inhibitor of protein synthesis. The lymphoma cell line BJAB was used as a model cell for leukemia and lymphoma cells.

Figure 6A:
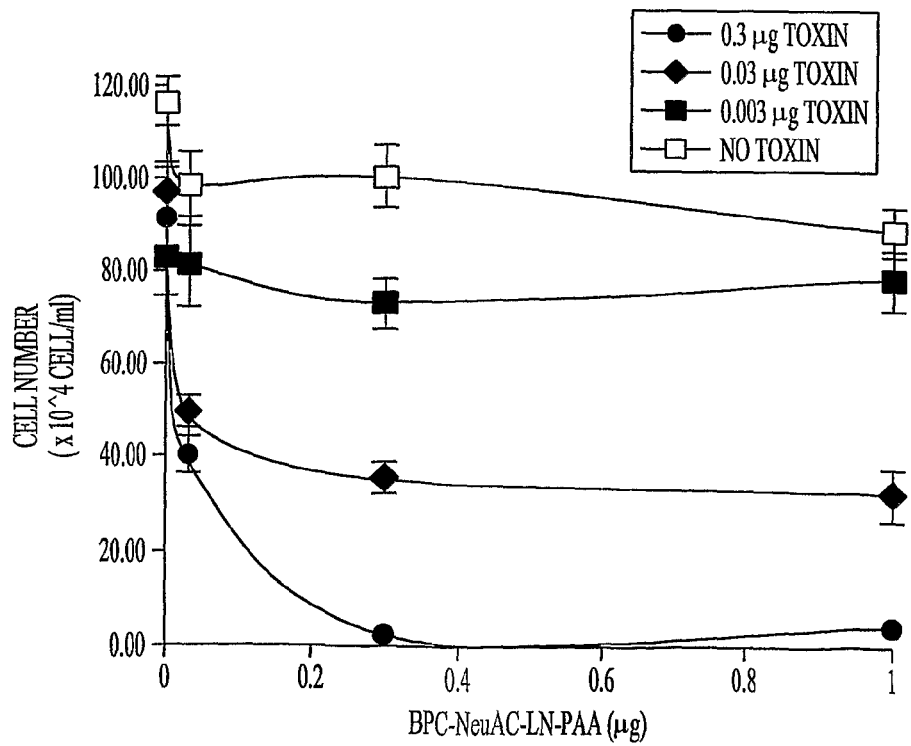
FIG. 6A-C shows that BPC-NeuAc-LN-PAA-toxin conjugates can target and kill lymphoma cells. To generate the data shown in FIG. 6A-B, streptavidin-conjugated saporin was pre-complexed with the high molecular weight BPC-NeuAc-LN-PAA probe for 15 min and then mixed with BJAB, Daudi or RAJI lymphoma cells. After 48 h in culture, the cells were harvested and viable cells were quantified. Data shown are the average ±S.D. of quadruple determinations and are representative of two to three independent experiments. To generate the data shown in FIG. 6C, primary human peripheral blood B cells were premixed at equal numbers with the lymphoma cells before adding pre-complexed saporin-BPC-NeuAc-LN-PAA as above. After 48 h viable cells were quantified. Data shown are the average ±S.D. of quadruple determinations and are representative of two independent experiments.
Figure 6B:
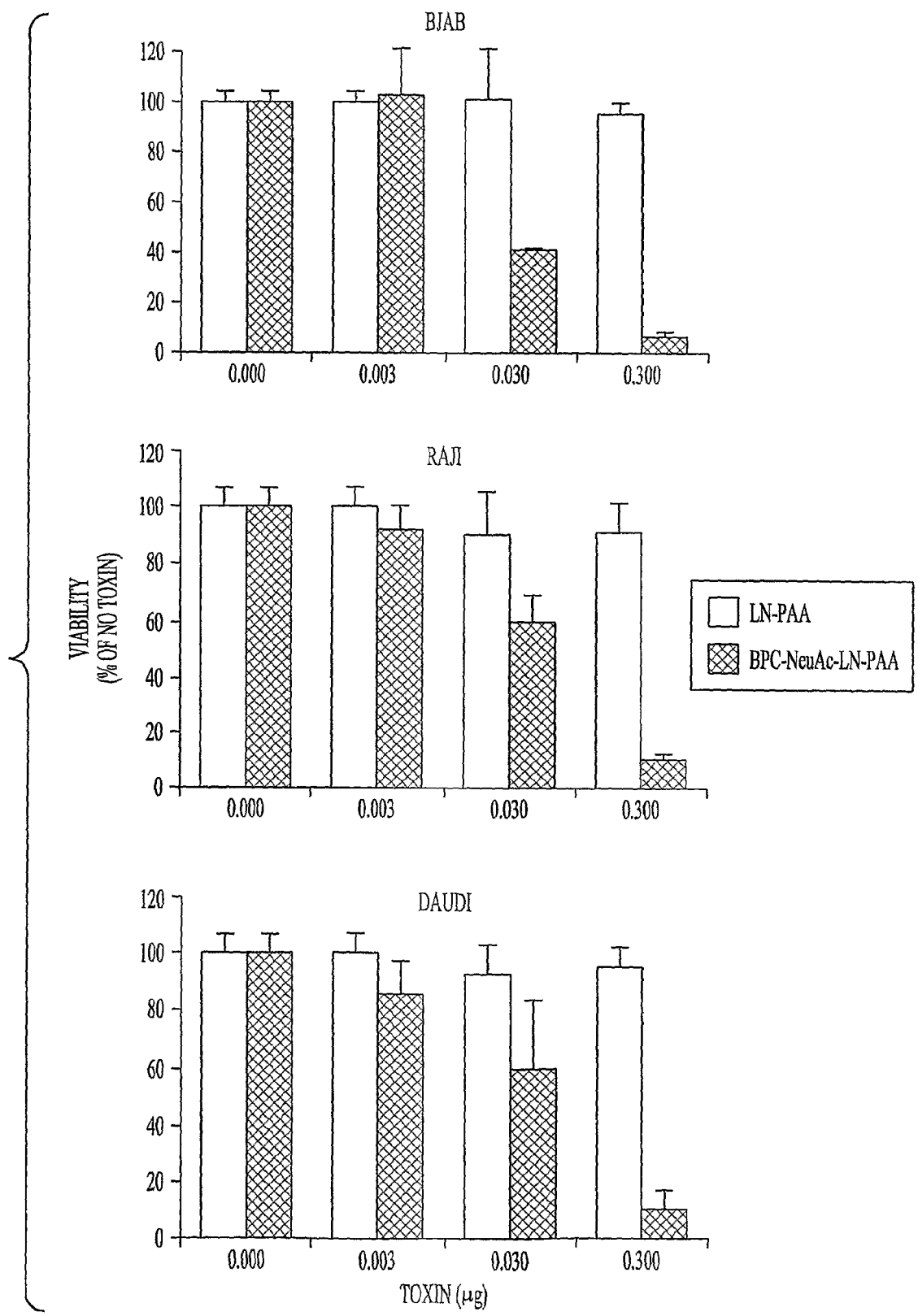
Figure 6C:
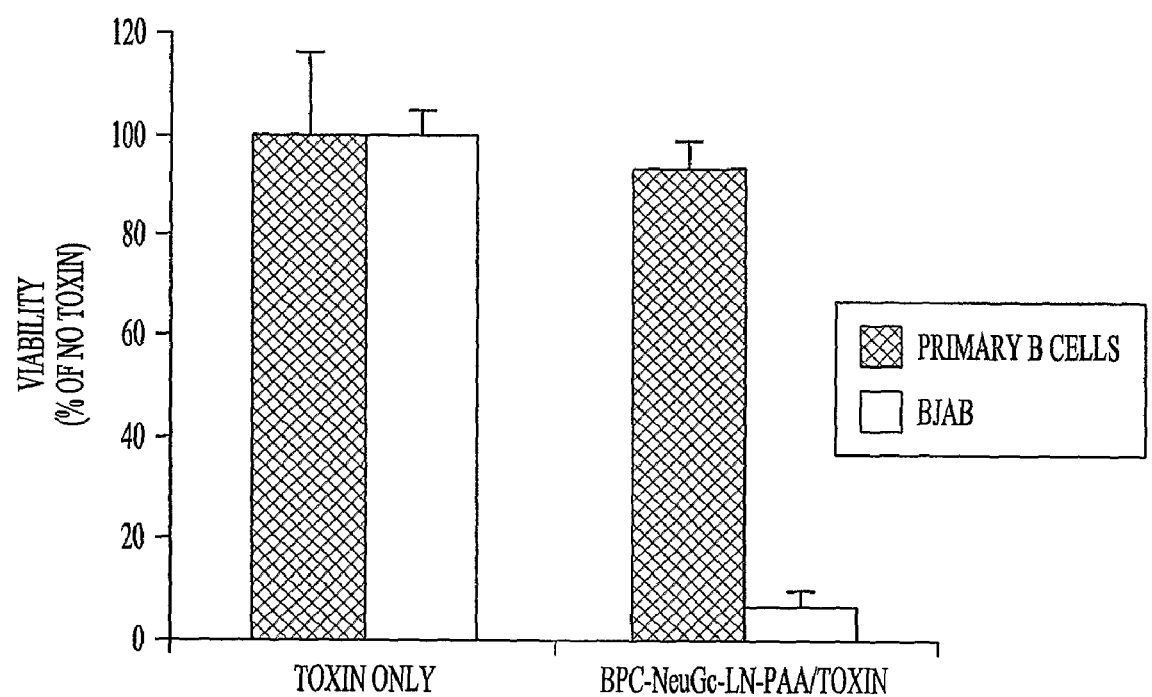

As shown in FIG. 6A, high levels of B cell killing were observed within 48 h of exposure to the saporin-sialoside probe. Killing required both the targeting sialoside and the toxin because no killing was observed in the absence of either the probe or the toxin. Similar killing was observed with other lymphoma cell lines including Daudi and RAJI (FIG. 6B). Surprisingly, when the BJAB cell line was co-cultured with primary human B cells, very few of the primary cells were killed (FIG. 6C). These data indicate that the toxin-sialoside construct may preferentially target transformed cells. These data may provide the first evidence that a carbohydrate-based probe can specifically target, bind and kill transformed B cells.

As shown above, potent sialoside ligands for CD22 have been developed that can compete with cis ligands, resulting in stable binding to native B cells. Such sialoside ligands are useful for purifying B cells and, when conjugated to selected therapeutic agents or toxins, can be used to deliver those agents or toxins to B cells, including cancerous B cells.

EXAMPLE 4

Hetero-Bifunctional CD22 Ligands Drive IgM Binding and Complement Killing of CD22-Expressing Cells This Example demonstrates that when IgM antibodies are linked to the Siglec ligands of the invention, the Siglec ligand not only bound to native B cells but also induced complement and killed the B cells to which the ligands were bound.

Materials and Methods:

Cells and Abs. Cells expressing IgM antibodies reactive with nitrophenyl (NP) groups were obtained from the ATCC and maintained in RPMI with 5% low IgG sera. The following antibodies were obtained as follows: Anti-CD19 (BD pharmingen); FITC labeled anti-IgM (Jackson Immunoresearch); and HRP-labeled anti-Ig (Jackson Immunoresearch). COS cells maintained in DMEM were transfected with plasmid encoding for hCD22Fc (E. C. Brinkman-Van der Linden et al., *J Biol Chem* 275, 8633 (Mar. 24, 2000)) by lipofectamine (Invitrogen) and then cultured for 3 additional days in OptiMEM. CD22Fc was purified as described previously by O. Blixt, B. E. Collins, I. M. van den Nieuwenhof, P. R. Crocker, J. C. Paulson, *J Biol Chem* 278, 31007 (Aug. 15, 2003).

ELISA-Type Assay. High Binding microtiter plates were coated with neutravidin (1 ug/50 ul/well in Na Bicarbonate pH 9.5) overnight at 4° C., then washed with 200 ul of HBSS/BSA. Culture supernatants containing hCD22Fc chimera were incubated in the wells for 2 h at room temperature. Wells were then washed and a mixture of IgM antibodies that recognize nitrophenyl groups (anti-NP antibodies) and 50 ul of varying concentrations of the BPC-Siaα2-6LN heterobifunctional ligand were added. The plates were allowed to bind for 30 min. Wells were then washed 2×200 ul of HBSS/BSA and then incubated with a 1:3000 dilution of the HRP conjugated anti IgM for 30 min at room temperature. Wells were washed 3×200 μl and then developed with OPD.

Figure 7A:
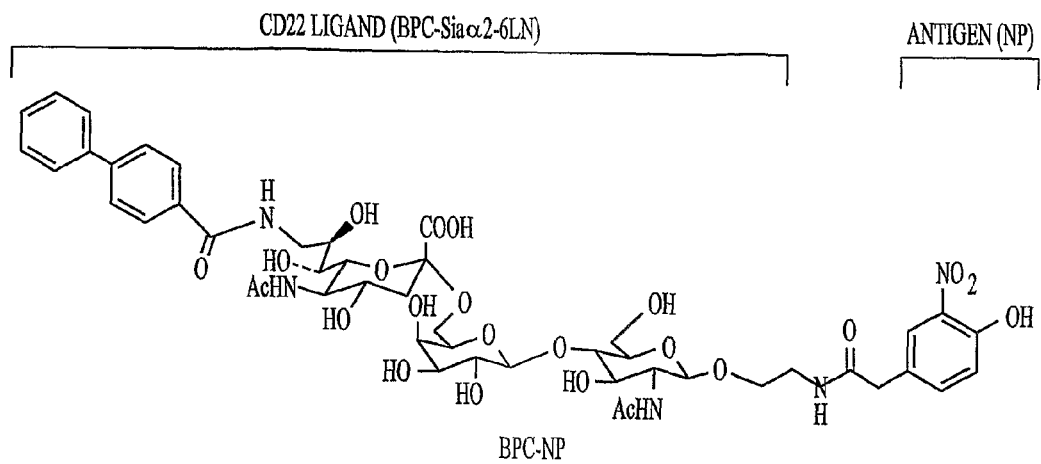
FIG. 7A-7C illustrate a self-assembling B cell targeting complex as one aspect of the invention.

Cell Binding. BJAB cells, incubated with or without exogenous sialic acid (4 mM) for 2 days, were resuspended in HBSS/BSA at a density of 1×10$^6$ cells/ml and the varying amounts of IgM and the BPC-NP construct shown in FIG. 7 were added to the cells and allowed to bind for 1 hr on ice. Cells were then washed with 1 ml of HBSS/BSA and then incubated with FITC-labeled anti-IgM for 30 min on ice. After washing again, the cells were read by flow cytometry. Primary human peripheral blood lymphocytes were isolated by diluting human blood 1:1 into 0.9% NaCl and then overlaid on lymphoprep (Invitrogen).

Antibody labeling. The IgM antibodies were purified by dialysis of media against water overnight with two changes of water. IgM antibodies were pelleted by centrifuging at 13000 rpm for 1 h at 4° C. The pellets were resuspended in PBS. Prior to labeling, the IgM antibodies were dialyzed into Na Bicarbonate, pH 8.0 buffer overnight at 4° C. The IgM antibodies were then labeled according to manufacturers instructions. Briefly, the IgM antibodies (1 mg) in 1 ml of buffer were reacted with 10 μg of Alexa Flour labeling reagent. After allowing the labeling to proceed for 1 h, labeled IgM antibodies were purified by gel filtration.

Internalization and cell killing assays. Cells were reacted as indicated above with the directly labeled IgM antibodies mixed with the BPC-NP construct. After washing, the cells were then incubated for varying periods of time at 37° C. and then washed with HBSS or RPMI pH 2 to remove any surface antibody. The cells were then washed 2×1 ml with HBSS/BSA to restore pH and read on the flow cytometer. Sera were isolated from normal human donors by allowing the blood to clot, then removing the clot and centrifuging the sera samples to clarify them. The sera was removed and immediately frozen in a dry ice ethanol bath until use. Cells were reacted with the IgM/BCP-NP construct as above and then incubated with 15% normal human sera for 2 h. Unlabeled cells and cells that were reacted with NP (not BPC-NP) served as controls. The viable cells in each reaction were quantified.

Synthesis of Heterobifunctional Reagent:

General Methods: 4-Hydroxy-3-nitrophenylacetic acid and N-hydroxysuccinimide ester were purchased from Biosearch Technologies. 5-Acetamido-9-amino-3,5,9-trideoxy-D-glycero-D-galacto-2-nonulo-pyranosyl-onate (9-amino-NeuAc) was synthesized according to a procedure published by S. Han, B. E. Collins, P. Bengtson, J. C. Paulson, *Nat Chem Biol* 1(2): 93-97 (July 2005). 2'-Aminoethyl-β-D-2-acetamido-2-deoxy-glucopyranoside was synthesized as described by K. Eklind, R. Gustafsson, A. K. Tiden, T. Norberg, P. M. Aberg, J *Carbohydr Chem* 15, 1161 (1996). All other reagents and solvents were purchased from Aldrich Chemicals and used without further purification. Solvent concentration was performed under reduced pressure at <40° C. bath temperature. All $^1$H and $^{13}$C NMR spectra were recorded at 30° C. using a Varian Unity Inova 400 Spectrometer. Chemical shifts are reported in parts per million from high to low field and referenced to the solvents. Standard abbreviations indicating multiplicity were used as follows: s=singlet, d=doublet, t=triplet, q=quadruplet, and m=multiplet. MALDI-FTMS spectrometry was recorded with an Ionspec Ultima FTMS (Ionspec Corp., Irvine, Calif.,) using dihydroxybenzoic acid as the matrix, and carried out by services at The Scripps Research Institute. Thin layer chromatography was performed on Silica Gel 60F from Fisher. After development with appropriate eluents, spots were visualized by dipping in 5% sulfuric acid in ethanol, followed by charring. Flash chromatography was performed on 230-400 mesh silica gel under positive air pressure. Enzymes, hST6GalI, beta-1,4-Galactosyltransferase-/UDP-4'-Gal Epimerase Fusion Protein, and others, were prepared using available procedures.

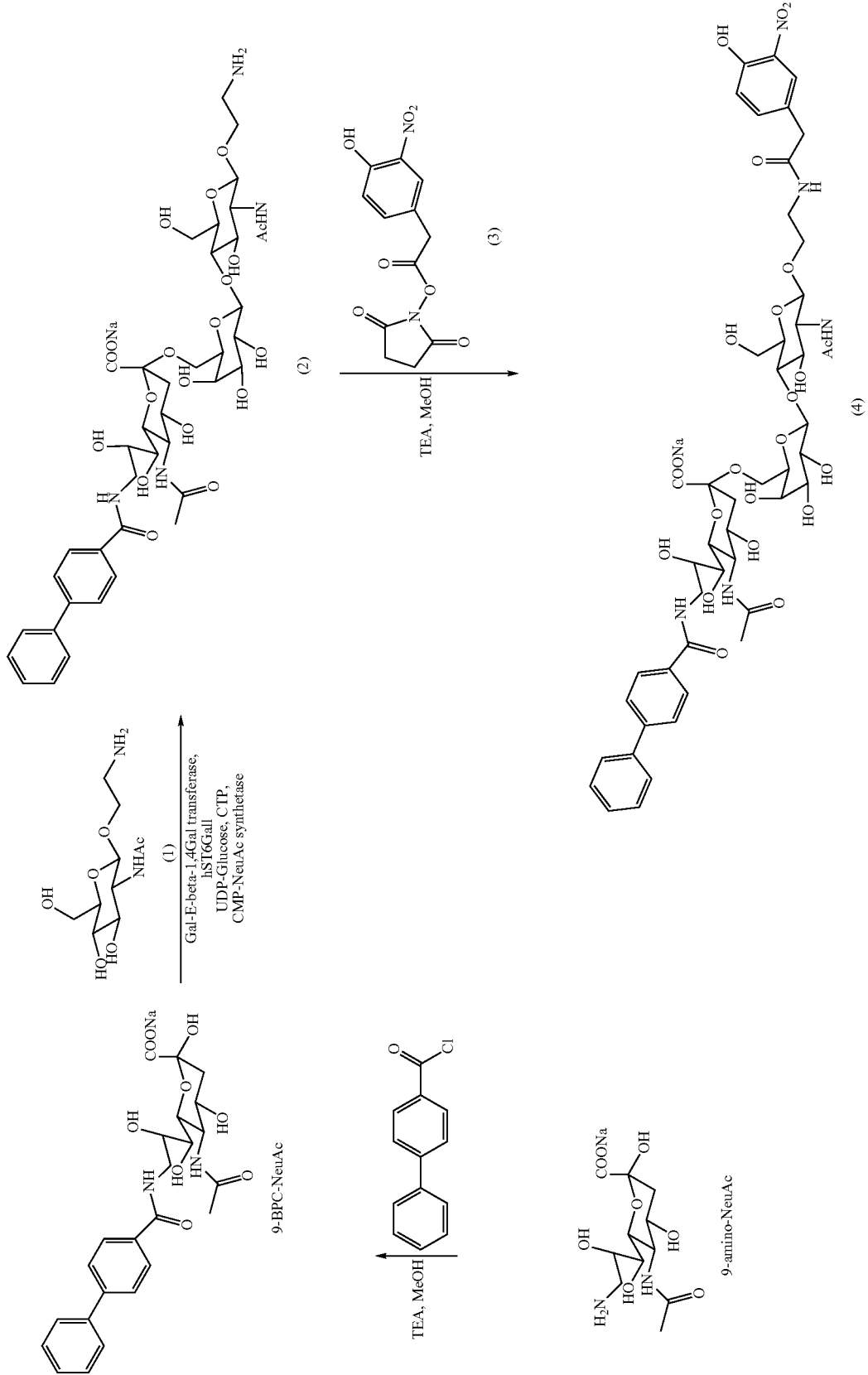

Synthesis of 5-Acetamido-9-[(1,1'-biphenyl)-4-carboxamido]-3,5,9-trideoxy-D-glycero-D-galacto-2-nonulo-pyranosyl-onate (9-BPC-NeuAc)

A solution of 9-amino-NeuAc (200 mg) in methanol was kept basic with triethylamine. To this solution was added biphenylacetyl chloride dissolved in methylene chloride (2M) dropwise until the reaction was complete as monitored by TLC. The solvents were evaporated and the residue was purified by flash chromatography on silica gel eluted with methylene chloride/methanol (10:1 to 1:2) to afford BPC-NeuAc (180 mg) in 75% yield. $R_f$: 0.5 (4:3:2 i-PrOH:MeCN:MeOH). $^1$H NMR (CD$_3$OD) δ 7.92 (d, 2H, J=8.4 Hz), 7.71 (d, 2H, J=8.4 Hz), 7.64 (d, 2H, J=7.2 Hz), 7.45 (t, 2H, J=7.5 Hz), 7.37 (m, 1H), 4.05 (m, 2H), 3.91 (m, 2H), 3.55 (t, 1H, J=6.3 Hz), 3.52 (m, 2H), 2.60 (m, 1H), 2.36 (t, J=6.9 Hz), 2.16 (dd, 1H, J=9.0, 4.2 Hz), 1.95 (s, 3H), 1.87 (t, 1H, J=12.0 Hz); MS: (C24H28N2O9): calculated (MH+): 489.1867, found: 489.1876.

Synthesis of [2-aminoethyl-β-]-[[5-Acetamido-9-[(1,1'-biphenyl)-4-carboxamido]-3,5,9-trideoxy-D-glycero-D-galacto-2-nonulo-pyranosyl-onate-α2-6-O-D-galactopyranosyl-β-1-4]]-D-2-acetamido-2-deoxy-glucopyranoside To the sodium cacodylate buffer (50 ml, 100 mM, pH 8.0) containing MgCl$_2$ (20 mM), MnCl$_2$ (20 mM), CTP (150 mg), 9-BPC-NeuAc (50 mg), UDP-Glucose (150 mg), and 2'-aminoethyl-β-D-2-acetamido-2-deoxy-glucopyranoside (40 mg) was added beta-1,4-Galactosyltransferase-/UDP-4'-Gal Epimerase Fusion Protein (20 U), CMP-NeuAc synthetase (10 U) and human ST6Gall sialyltransferase (2 U). The reaction mixture was slowly stirred at room temperature for 3 days. Enzymes were removed by passing the reaction mixture through a Centricon filter (MWCO 10,000 Dalton). The filtrate was lyophilized and the residue was dissolved in minimum amount of water, loaded to a P-2 gel chromatography column and eluted with water. Appropriate fractions were pooled and lyophilized to afford the desired product (2, 55 mg) in 70% yield. $^1$H MHR (CD$_3$OD) δ 7.82 (d, 2H, J=8.4 Hz), 7.61 (d, 2H, J=8.4 Hz), 7.55 (d, 2H, J=7.2 Hz), 7.36 (t, 2H, J=7.8 Hz), 7.27 (m, 1H), 4.46 (d, 1H, J=8.4 Hz), 4.23 (d, 1H, J=7.2 Hz), 3.56-4.1 (m, 10H), 3.30 (d, 1H, J=7.8 Hz), 3.20 (m, 4H), 3.01 (m, 1H), 2.64 (dd, 1H), 1.91 (s, 3H), 1.88 (s, 3H), 1.57 (t, 1H, J=12 Hz); $^{13}$C NMR (CD$_3$OD) δ: 174.87, 174.63, 169.83, 145.41, 141.18, 134.42, 130.07, 129.11, 129.04, 128.11, 128.02, 105.04, 102.36, 101.54, 81.80, 76.47, 75.67, 74.66, 74.07, 73.42, 72.57, 72.33, 71.65, 70.32, 69.77, 66.51, 64.91, 62.01, 59.60, 52.28, 56.73, 53.93, 52.80, 51.23, 44.64, 42.35, 40.98, 23.49, 22.88, 17.66, 15.89; MS(C40H56N4O19) Calculated (MNA+) 919.3436, found 919.3473

Synthesis of [(4'-hydroxyl-3'-nitrophenylacetamido)-ethyl-β-]-[[5-Acetamido-9-[(1,1'-biphenyl)-4-carboxamido]-3, 5,9,trideoxy-D-glycero-D-galacto-2-nonulo-pyranosyl-onate-α2-6-O-D-galactopyranosyl-β1-4]]-D-2-acetamido-2-deoxy-glucopyranoside To a flask with methanol (5 mL) was added 4-hydroxy-3-nitrophenylacetic acid, N-hydroxysuccinimide ester (50 mg) and 2'-aminoethyl-β-]-[[5-Acetamido-9-[(1,1'-biphenyl)-4-carboxamido]-3,5,9-trideoxy-D-glycero-D-galacto-2-nonulopyranosyl-onate-α2-6-0-D-galactopyranosyl-β1-4]]-D-2-acetamido-2-deoxy-glucopyranoside (20 mg). The solution kept basic with addition of triethylamine and stirred at room temperature for two days. The solvent was evaporated and the residue was purified by flash chromatography on silica gel to afford the desired product (18 mg) in 75% yield. $^1$H MHR (CD$_3$OD) δ 7.85 (d, 1H, J=2.4 Hz), 7.86 (d, 2H, J=8.4 HZ), 7.60 (d, 2H, J=8.4 Hz), 7.54 (d, 2H, J=7.2 Hz), 7.35 (dd, 1H, J=6.3, 1.8 Hz), 7.32 (t, 2H, J=7.2 Hz), 7.25 (m, AH), 6.93 (d, 1H, J=8.7 Hz), 4.40 (d, AH, J=8.1 HZ), 4.20 (d, IH, J=6.9 Hz), 3.95 (m, 2H), 3.34 (s, 2H), 3.80-3.40 (m, 8H), 3.15-3.3 (m, 4H), 2.64 (dd, IH, J=4.5, 12.0 Hz), 1.87 (s, 3H), 1.86 (s, 3H), 1.60 (t, 1H, J=12.0 Hz), $^{13}$C NMR (CD$_3$OD) δ: 174.83, 174.50, 173.51, 170.03, 145.52, 141.26, 138.71, 134.38, 130.10, 130.01, 129.98, 129.05, 129.00, 128.10, 128.03, 126.47, 105.18, 102.49, 101.54, 76.42, 73.98, 72.42, 69.10, 64.89, 62.13, 42.09, 40.90, 26.11, 23.44, 9.51; MS (C48H61N5O23) Calculated (MNA+) 1098.3649, found 1098.3649.

Results:

CD22 recognizes and binds with high affinity sialosides having biphenyl derivatives at the 9-position of sialic acid. A backbone structure was sought that could present this sialoside with sufficiently high valence to compete with cis carbohydrate ligands and bind to CD22 on the cell surface. In addition, the backbone would optimally have a defined valency. The IgM antibody structure is perfectly suited for such a purpose, because all fingers can bind to the same face. However, rather than directly coupling of a CD22 ligand to the IgM backbone the inherent ligand binding abilities of the IgM molecule was used.

Therefore, a heterobifunctional sialoside was synthesized by conjugation of a nitrophenyl moiety to the reducing termini of the BPC-NeuAcα2,6IacNAc sialoside through reductive amination. The two functional domains were attached directly to generate a "BPC-NP" ligand and the structure of this ligand was determined by MS and NMR.

Figure 7B:
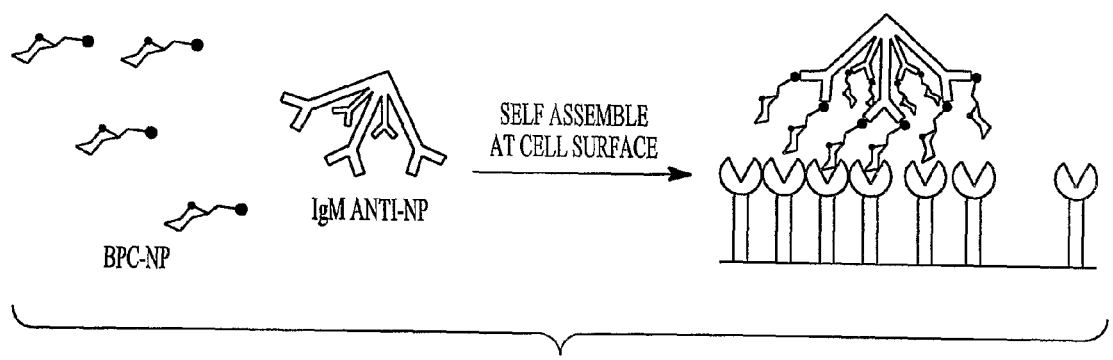

Mixtures of this heterobifunctional BPC-NP reagent with IgM antibodies directed against the NP structure along with CD22-expressing cells spontaneously forms a decavalent complex with the CD22 ligand analog molecules at the surface of CD22-expressig cells (see FIG. 7B).

Figure 7C:
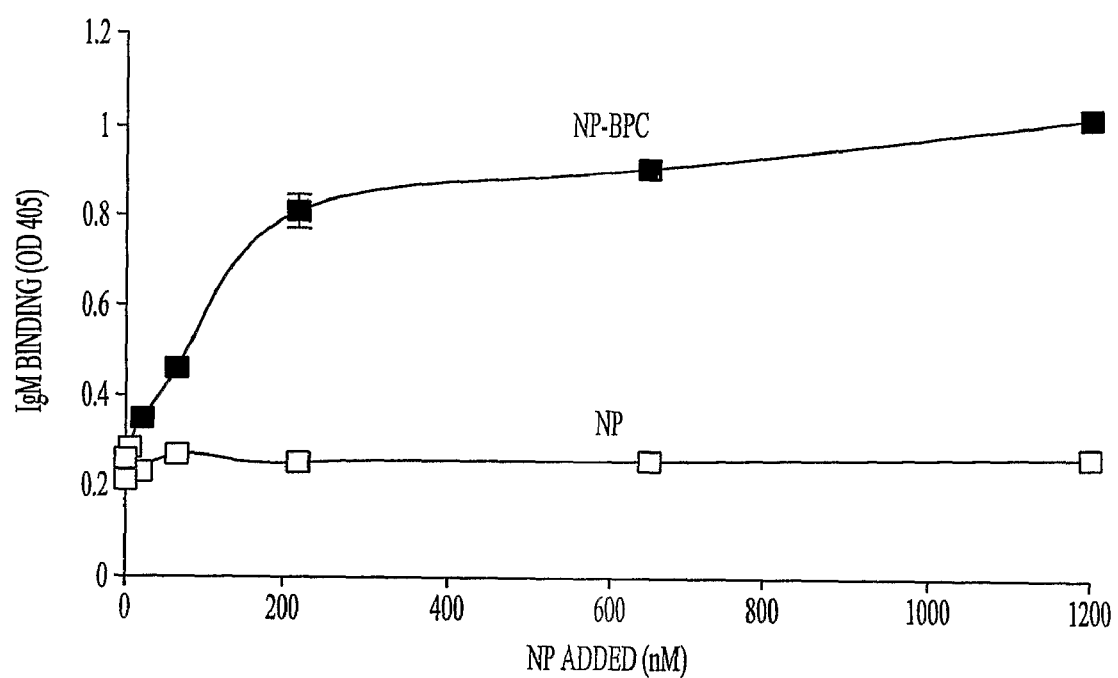

An ELISA-type assay was used to demonstrate that the self-assembled complex results in stable binding to CD22 (FIG. 7C). CD22Fc chimeras were immobilized onto microtiter plates and overlaid with mixtures of IgM anti-NP and NP or NP-BPC. Following washing, bound IgM complex was detected with HRP-conjugated anti-Ig antibodies. CD22-dependent binding of the complex was detected, with maximal IgM complex binding achieved when using less than 200 nM NP-BPC. Significantly, no IgM binding to CD22 was observed with NP alone, or in the absence of CD22 (FIG. 7C, some data not shown).

As shown in previous Examples, when presented with high valency (>500) on a polyacrylamide based structure, the BPC-sialic acid analog could compete effectively with the high density of sialic acid ligands present on the surface of cells. Thus, when a carrier (e.g. polyacrylamide) was used to display many BPC-sialic acid ligands, this complex could bind to CD22 on native B cell surfaces. However, the same sugar and backbone at a lower valency (15 sugars) could not bind.

Figure 8A:
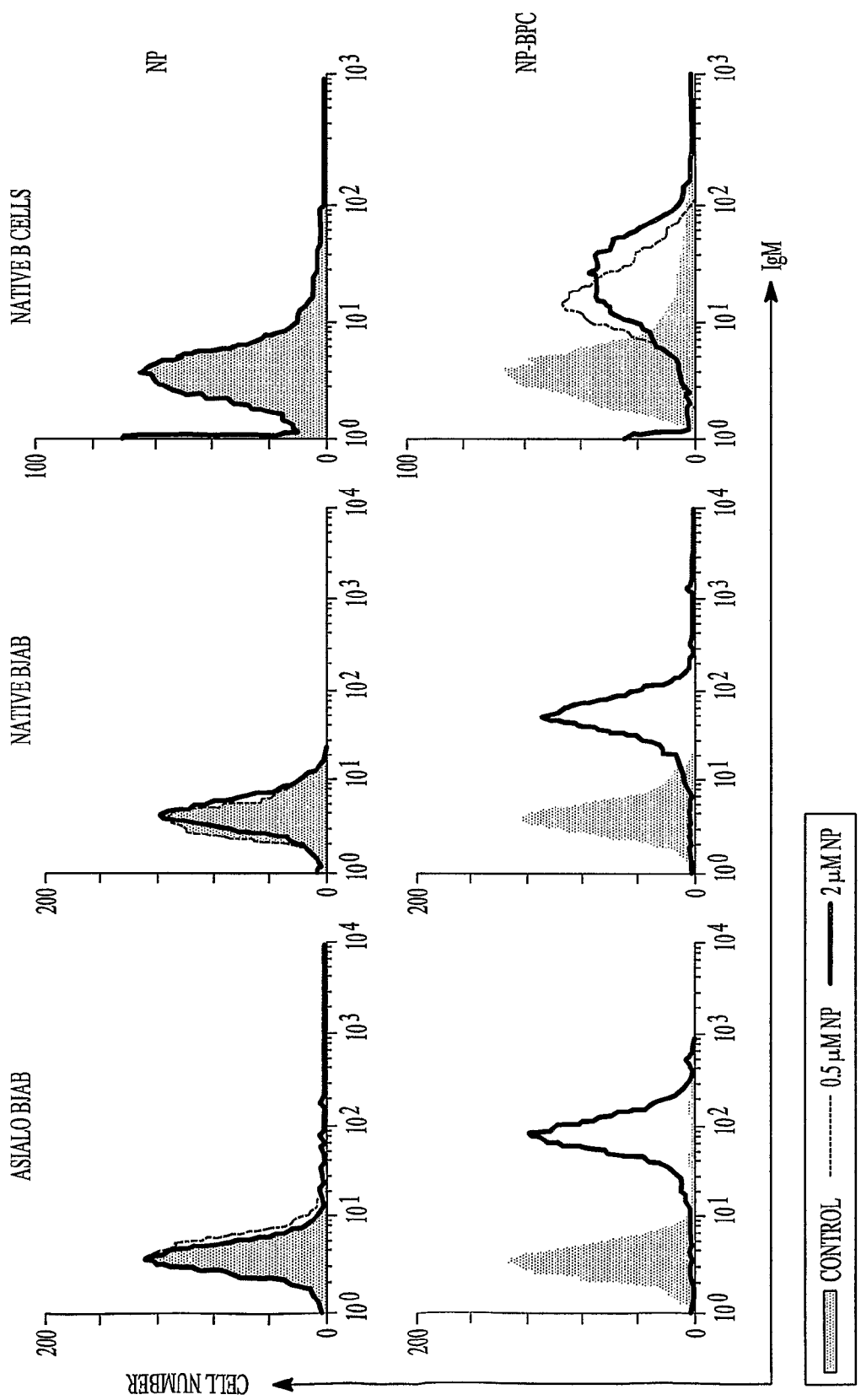
FIG. 8A-8C show that the self-assembled IgM-NP-BPC complex binds CD22. To generate the results shown in FIG. 8A, native or sialic acid-deficient (asialo) human lymphoma BJAB cells or native human peripheral B cells were incubated with NP or NP-BPC at the indicated concentration and with the IgM anti-NP antibodies (40 μg/ml) on ice. Following washing, bound IgM was detected with FITC-labeled anti-Ig and read by flow cytometry.

To further evaluate the ability for the IgM complex to bind to CD22 on B cells, cells deficient in cell-surface sialic acid were used. In particular, the K20 subclone of the BJAB human B cell lymphoma cell line was used because these K20 cells are deficient in the epimerase/kinase step of sialic acid biosynthesis and do not express sialic acid on their cell surface unless first cultured in the presence of sialic acid, or the precursor N-acetyl mannosamine. Exposing asialo K20 cells to the BPC heterobifunctional sialoside and the anti-NP IgM antibodies resulted in binding of the self assembled complex to CD22 expressed on the B cell surface (FIG. 8A). The results observed were similar to what had been observed with the 15 or 500 valent polyacrylamide structures. Maximal binding of the complex was observed at 0.16 µM BPC-NP, while no binding was observed if only NP and the IgM anti-NP were present. This binding appeared stable because no detectable loss was observed over a 1 h period of time (data not shown).

Figure 8B:
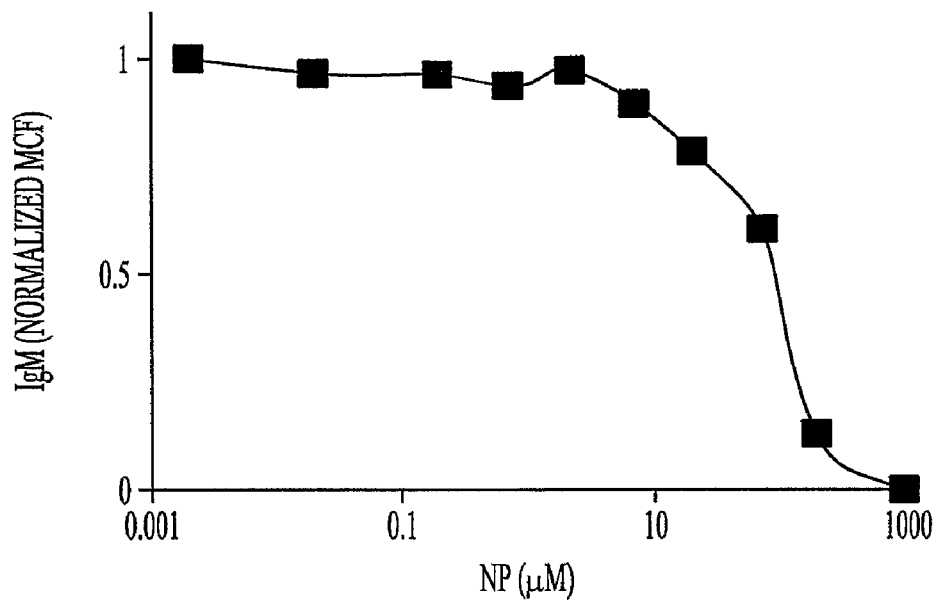

Moreover, despite a high concentration of cis ligands on the sialylated BJAB cells, the heterobifunctional BPC-NP construct bound efficiently to CD22 (FIG. 8A), though binding to sialylated BJAB cells required slightly higher concentrations of the BPC-NP ligand. In contrast, essentially no binding was observed with the 15 valent polyacrylamide construct. Most importantly, the IgM-NP-BPC complex bound to CD22 expressed on native B cells from peripheral blood (FIG. 8A). Binding appeared specific for B cells as no binding was observed to other leukocytes. Significantly, formation of the complex on B cells was blocked by increasing the amounts of free NP (FIG. 8B, $IC_{50}$ approximately 200 µM).

Figure 8C:
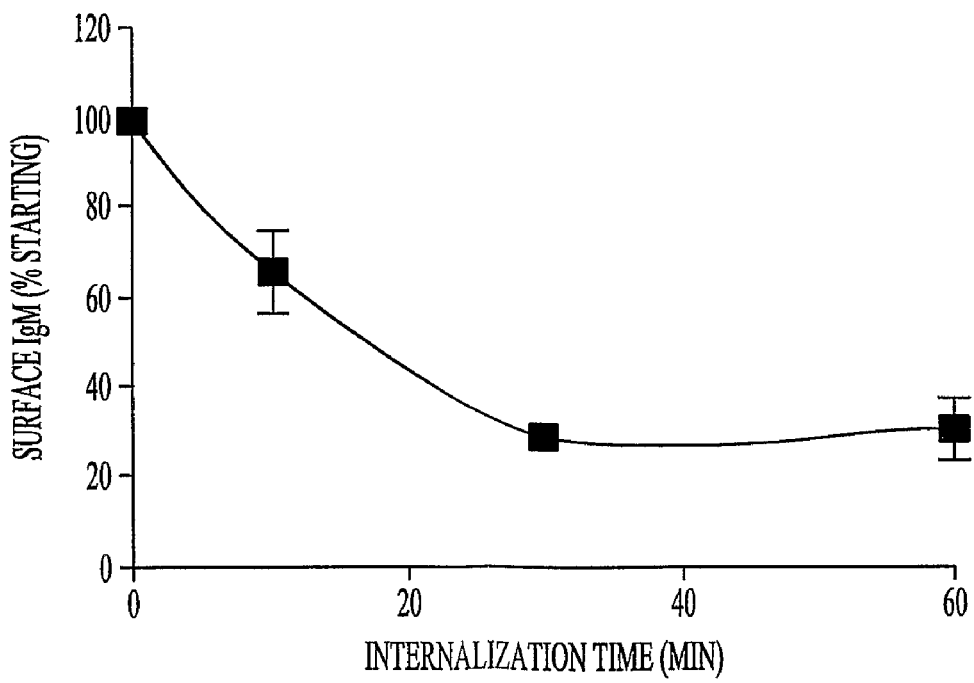

The ability of the complex to form specifically on CD22 expressing B cells makes it an attractive potential therapeutic. Moreover, the IgM-NP-BPC complex is endocytosed following binding, such that conjugation of a toxin to the IgM would result in efficient killing (FIG. 8C). Therefore, the specificity of binding to B cells and its endocytosis into B cells after binding, demonstrates that the IgM-NP-BPC complex can be used for delivery of therapeutic agents to B cells.

However, IgM antibodies can innately activate complement, which leads to cellular lysis. Therefore, tests were performed to ascertain whether the IgM-NP-BPC complex could lead to complement-mediated lysis of B cells, when the complex was bound to B cells and exposed to normal human serum, which contains the complement factors necessary for complement-mediated cellular lysis. Thus, sialylated BJAB cells were incubated with the NP-BPC and IgM anti-NP in the presence or absence of 16% human sera. After 4 h at 37° C., to allow for lysis to occur, cell viability was determined. As a control, an anti-CD45 antibody known to bind complement and reactive with B cells was used to assess whether complement can kill cells in this assay and what percentage of cells may be killed.

Figure 9:
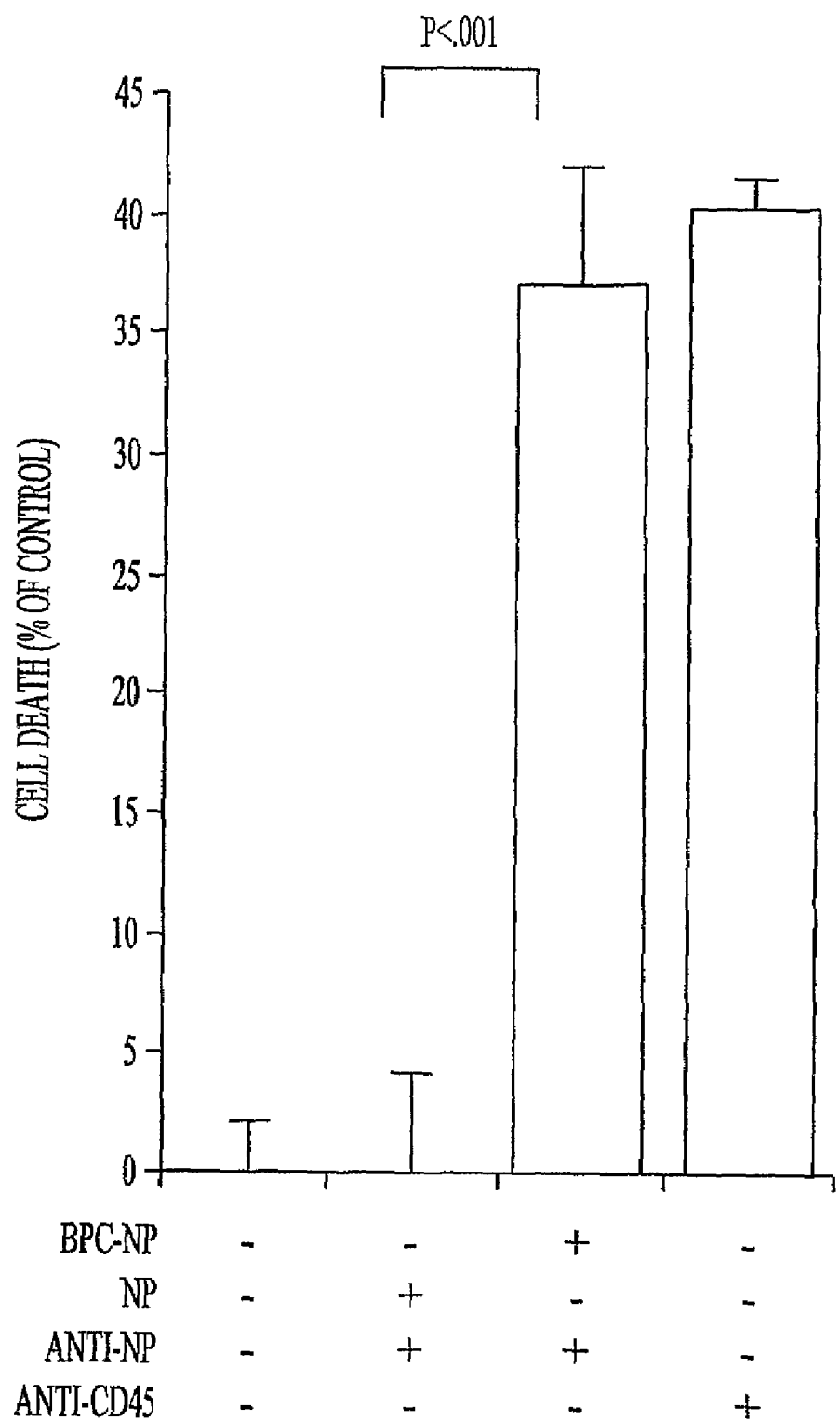
FIG. 9 shows that the IgM-NP-BPC complex binds B cells and activates complement for B cell killing. BJAB cells were incubated with 2 µM NP-BPC and anti-NP IgM antibodies (40 µg/ml) then plated in media containing 16% human sera, and incubated at 37° C. for 4 h. Cells were harvested and viable cells quantified. As a control cells were incubated with anti-CD45 antibody. Data are the average +/−S.D and are representative of two experiments.

While essentially no cell killing was observed when no NP-BPC and no IgM anti-NP were used, use of the IgM-NP-BPC complex resulted approximately 33% B cell death (FIG. 9). The control (anti-CD45 antibodies) resulted in similar levels of cell killin (about 40% cell lysis, FIG. 9). Killing was specific to the CD22 heterobifunctional ligand, because no lysis was observed when this ligand was replaced with NP (FIG. 9).

EXAMPLE 5

Siglec-8-related Siglecs Bind and Internalize Multivalent 6'-sulfo-sLe$^X$ (Neu5Acα2-3 [6-SO$_4$]Galβ1-4 [Fucα1-3]GlcNAc) Ligands This Example illustrates that Siglec ligands for other Siglecs are readily bound to the cell surface of Siglec-expressing cells and are internalized. Hence, according to the invention, such Siglec ligands are useful transport/delivery agents for delivering therapeutic agents to Siglec-expressing cells.

Materials and Methods

Antibodies and reagents. Purified rat anti-Siglec-F (clone E50-2440), PE-anti-Siglec-F (PE-anti-SigF, clone E50-2440), FITC-anti-human CD22 (HIB22), PE-Cy5-streptavidin, anti-Syntaxin-8 (clone 48), anti-EEA1 (clone 14), and rabbit anti-caveolin pAb were purchased from BD Biosciences Pharmingen (San Diego, Calif.). Anti-hamster LAMP2 (clone UH3) was purchased from Developmental studies hybridoma bank. Anti-clathrin heavy chain (clone ×22) was purchased from Abcam. Affinity-purified sheep anti-Siglec-F IgG was prepared as described (Zhang et al. Eur. J. Immunol. 34:1175-84 (2004). Alexafluor (AF) 488- and AF555-goat anti-mouse IgG, AF555-anti-mouse IgG$_1$, and AF555-anti-mouse IgG$_{2a}$, AF555-conjugated goat anti-rat IgG, AF555-goat anti-rabbit IgG, quantumdot (Qdot)655-streptavidin and AF488-streptavidine were purchased from Invitrogen. FITC-donkey anti-sheep IgG and FITC-donkey anti-rabbit IgG were purchased from Jackson Immunoresearch (West grove, PA). Anti-CD45 and anti-CD90 antibody conjugated magnetic beads were purchased from Miltenyi Biotech (Auburn, Calif.).

Synthesis of high molecular weight sialoside-PAA probe. Low molecular weight (30 kDa) and high molecular weight (1000 kDa) sialoside-polyacrylamide conjugates bearing Neu5Acα2-3 [6-SO$_4$]Galβ1-4[Fucα1-3]GlcNAc (6'-sulfo-sLe$^X$) or 9-biphenylcarbonyl (BPC)-Neu5Acα2-6Galβ1-4GlcNAc were synthesized by coupling spacer-linked oligosaccharides to poly(N-oxisuccinimidyl acrylate) (PAA) as described by Gambaryan et al. (Antiviral Res. 68:116-23 (2005)) and Mochalova et al. (Virology 313: 473-80 (2003). 1000 kDa LacNAc-PAA was obtained from The Consortium for Functional Glycomics. All sialoside-PAA probes were biotinylated to allow detection with streptavidin.

Mice. The IL-5 transgenic mouse, line NJ.1638, is described in Lee et al. J. Immunol. 158: 1332-44 (1997). C57B1/6 mice were obtained from the Scripps Research Institute. Protocols were conducted in accordance with the National Institutes of Health and the Scripps Research Institute.

Cell preparation. Single cell suspensions from spleen, lymph nodes, and bone marrow were obtained from 8-12 week old mice. Red blood cells were lysed by exposure to Ammonium Chloride lysis solution for 5 min (0.15 M ammonium chloride buffer pH 7.2 containing 10 mM potassium carbonate and 0.1 mM EDTA).

Plasmids. The full-length cDNA fragment of Siglec-F (AF293371) was amplified by PCR, cloned into pcDNA5/FRT/V5-His vector (Invitrogen) (Tateno et al., Glycobiology 15: 1125-35 (2005)). The full-length cDNA fragment of human CD22 was subcloned into pcDNA5/FRT/V5-His vector (Invitrogen) (Han et al., Nat. Chem. Biol. 1: 93-97 (2005). Site-directed mutagenesis was performed using a Genetailor site-directed mutagenesis system (Invitrogen) and a full-length Siglec-F cDNA cloned into pcDNA5/FRT/V5-His vector as template following the manufacturer's protocol. Dynamin-1 cDNA constructs (WT and K44A) were obtained from Dr. Sandra L. Schmid (The Scripps Research Institute, CA). N-terminally (dominant-negative) and C-terminally (wild-type) EGFP tagged Caveolin-1 cDNA constructs are described in Pelkmans et al., Nat. Cell. Biol. 3: 473-83 (2001). ARF6-EGFP cDNA constructs (WT, T27N, and Q67L) were obtained from Dr. Julie G. Donaldson (National Institute of Health, MD). Cells were grown to 70-80% confluency on coverslips and transiently transfected with plasmid using Lipofectamine 2000 (Invitrogen).

Drug treatments. Cells were preincubated for 30 min at 37° C. in Ham's F12/10% FCS medium containing 10 mM methyl-β-cyclodextrin (Sigma-Aldrich), 5 µM latrunculin A (Sigma-Aldrich), 1 µM jasplakinolide (EMD biosciences, CA), 100 µM genistein (Sigma-Aldrich), 100 µM PP2 (EMD biosciences), 100 µM sodium pervanadate, 1 µM nocodazol (Sigma-Aldrich), 10 µM amiloride (Sigma-Aldrich), 50 µM nystatin (Sigma-Aldrich), or 10 µM brefeldin A (Sigma-Aldrich). Cells were incubated with PE-anti-Siglec-F in the continued presence of the drugs at 37° C. for 1 hr. Drug treatment did not affect cell viability.

Cell culture. CHO cells were cultured in Ham's F12 medium, respectively, supplemented with 10% fetal calf serum (FCS), penicillin (100 U/ml), and streptomycin (100 ug/ml). Stable clones of CHO cells expressing Siglec-F, Siglec-F mutants, and human CD22 were generated by lipofectamine 2000 (Invitrogen) and selection in 0.5 mg/ml hyglomycin B (Roche Molecular Biochemicals).

Flow cytometry. Cells ($5 \times 10^5$) suspended in PBS/BSA (10 mM phosphate-buffered saline pH 7.0 containing 10 mg/ml BSA) were incubated with 110 µg/ml of primary antibody or sialoside-PAA probe for 30 min on ice. After washing with PBS/BSA, cells were incubated with 10 µg/ml of FITC-conjugated secondary antibody or streptavidin-Cy5-PE for 30 min on ice. For sialidase pretreatment, cells in PBS/BSA were incubated with 25 mU of *A. ureafaciens* sialidase (Roche Molecular Biochemicals) for 30 min at 37° C. Flow cytometry data were acquired on a FACS Calibur flow cytometer (BD Biosciences, San Jose, Calif.) and analyzed using the CellQuest software.

Immunofluorescence microscopy. For an internalization assay, CHO cells cultured on coverslips for 2 days were labeled with fluorescence-conjugated antibody (10 ug/ml) in PBS/BSA for 30 min on ice. Cells were then incubated at 37° C. for varying times, and internalization was stopped by transferring the cells to ice. After washing, cells were fixed with 4% paraformaldehyde (PFA, Electron Microscopy Services) for 15 min at room temperature. For colocalization experiments, cells were further permeabilized with 0.1% saponin in PBS for 20 min at room temperature and then incubated with the desired antibody for 1 hr at room temperature or 4° C. overnight. For eosinophil staining, eosinophils from IL5-Tg mice at $10^7$/ml in PBS/BSA were fixed with 2% PFA for 10 min at 4° C. before staining with the desired antibodies for 30 min at 4° C. After cell-surface staining, cells were then cytospun onto glass slides and fixed with 4% PFA for 20 min at room temperature. Cells were further permeabilized with 0.1% saponin in PBS for 20 min at room temperature and then incubated with anti-clathrin antibody (clone ×22). Cells were mounted with Prolong gold antifade reagent (Invitrogen) and examined using a Zeiss Axiovert S100TV microscope equipped with a Bio-Rad MRC 1024 confocal laser scanner. Images were collected with Bio-Rad LaserSharp 2000 software and analyzed with Image J (v. 1.33), Zeiss LSM image, and Adobe Photoshop.

Results

Figure 10A:
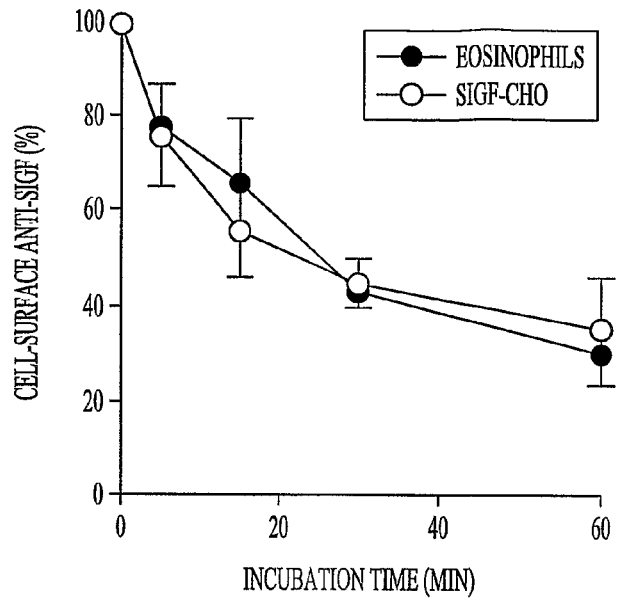
FIG. 10A-10C show that Siglec-F mediates endocytosis following ligation to an antibody. For FIG. 10A, SigF-CHO cells and mouse eosinophils were incubated with sheep anti-Siglec-F pAb on ice for 30 min and allowed to internalize by incubation at 37° C. for the indicated time. Cell-surface anti-Siglec-F pAb was detected by FITC-anti-sheep IgG. Anti-Siglec-F was internalized in mouse eosinophils and SigF-CHO cells (2%/min). Data are the average ±SD of three independent experiments. For FIG. 10B, SigF-CHO cells and mouse eosinophils were incubated with PE-anti-Siglec-F (dotted line, solid line) or isotype control (shaded) for 30 min on ice. After washing, the cells were allowed to internalize at 37° C. for the indicated period of time. Following the incubation, cells were washed with 0.2 M glycine buffer pH 2.0 (solid =intracellular) to remove surface bound antibody or PBS/BSA (shaded, dotted total probe) as a control. Bound or internalized antibody was measured by flow cytometry. Representative results are shown.

Endocytosis of Siglec-F following ligation by antibody. Endocytosis of Siglec-F was first investigated by detecting the decrease of anti-Siglec-F from cell surface using flow cytometry. Cell-surface Siglec-F was labeled with sheep anti-Siglec-F polyclonal antibody on ice for 30 min. The temperature was then raised to 37° C. and, at various times, cells were transferred to 4° C. Cell-surface anti-Siglec-F was detected by incubation with FITC-anti-sheep IgG at 4° C. for 30 min. The level of cell-surface anti-Siglec-F at 0 min was taken as 100%. Compared to the level at 0 min, the level of cell-surface antibody on mouse eosinophils was reduced after incubation at 37° C. (FIG. 10A). Approx. 60% of cell-surface anti-Siglec-F was internalized within 30 min at 37° C. (2%/min). To investigate the mechanisms responsible for this internalization in more detail, CHO cells were used that stably expressed Siglec-F (SigF-CHO) and CHO cells that stably expressed CD22 (CD22-CHO) were used for comparison. CHO cells have often been used to study receptor endocytosis.

As shown in FIG. 10, SigF-CHO cells internalized antibody at a similar rate to that seen in eosinophils. Anti-CD22 mAb was also internalized from the cell surface of CD22-CHO cells, with 50% internalization within 30 min (data not shown).

Figure 10B:
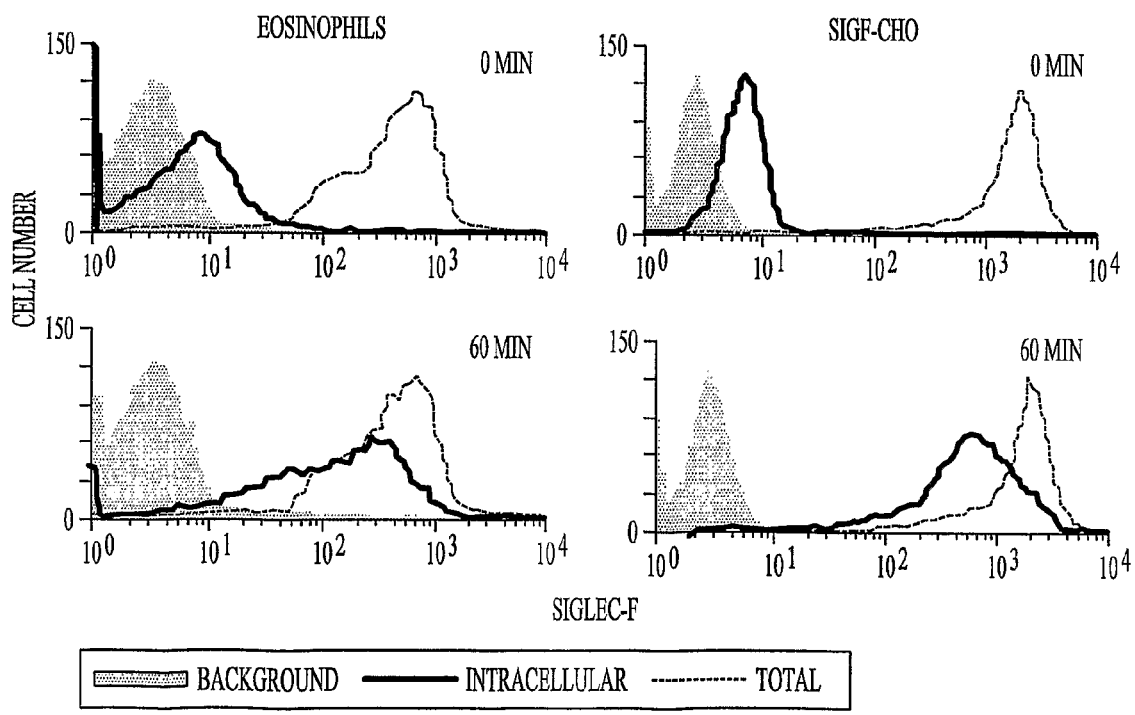
Figure 10C:
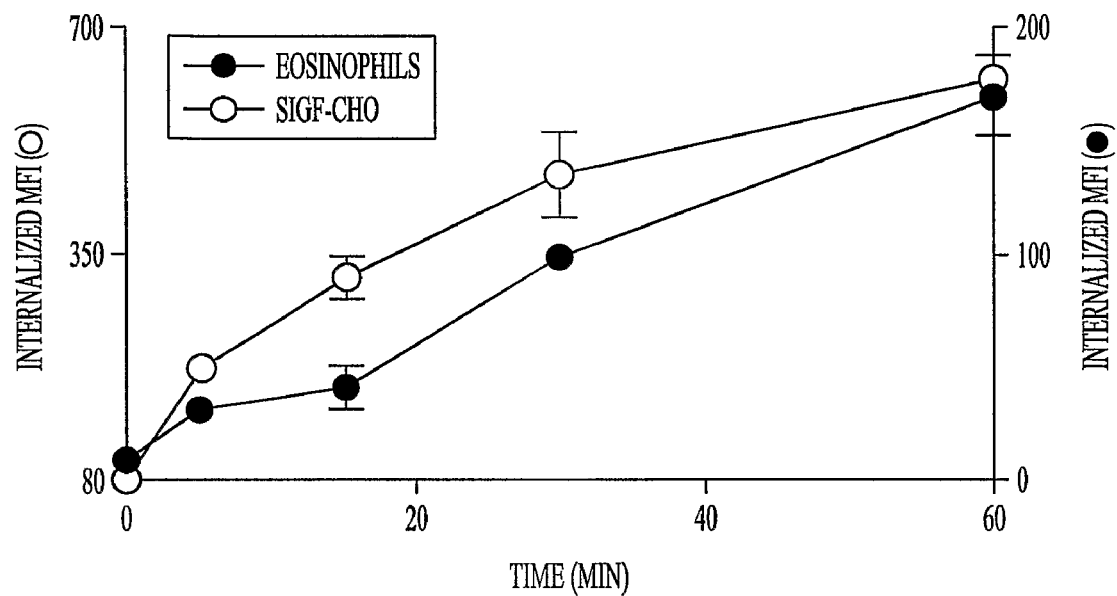

Endocytosis of Siglec-F was also investigated by directly detecting the internalized fluorescently-labeled monoclonal antibody by flow cytometry. Eosinophils or SigF-CHO cells were stained with PE-anti-Siglec-F mAb at 4° C., and allowed to internalize the labeled antibodies at 37° C. for up to 60 minutes. Residual cell surface antibody was removed by a brief low pH wash (0.2 M glycine buffer, pH 2.0). After incubation at 37° C. for 60 min, the level of intracellular PE-anti-Siglec-F monoclonal antibody detected was larger that observed at 0 min in both eosinophils and SigF-CHO cells (FIGS. 10B and 10C). These results indicate that Siglec-F is internalized following ligation by antibody on both mouse eosinophils and SigF-CHO cells.

Figure 11A:
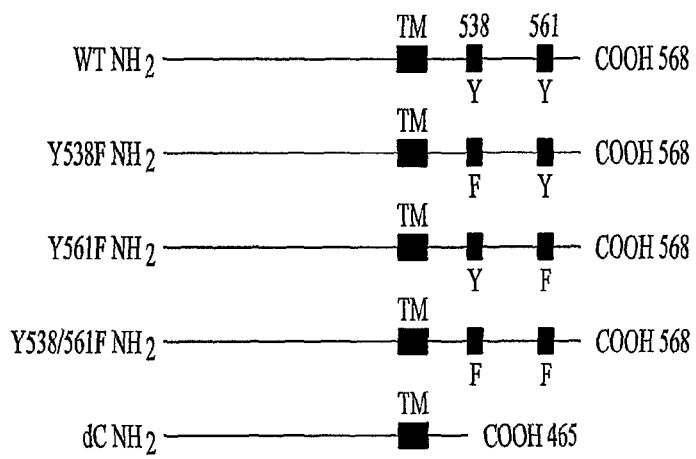
FIG. 11A-11C show that tyrosine-based motifs are required for endocytosis of Siglec-F.
Figure 11B:
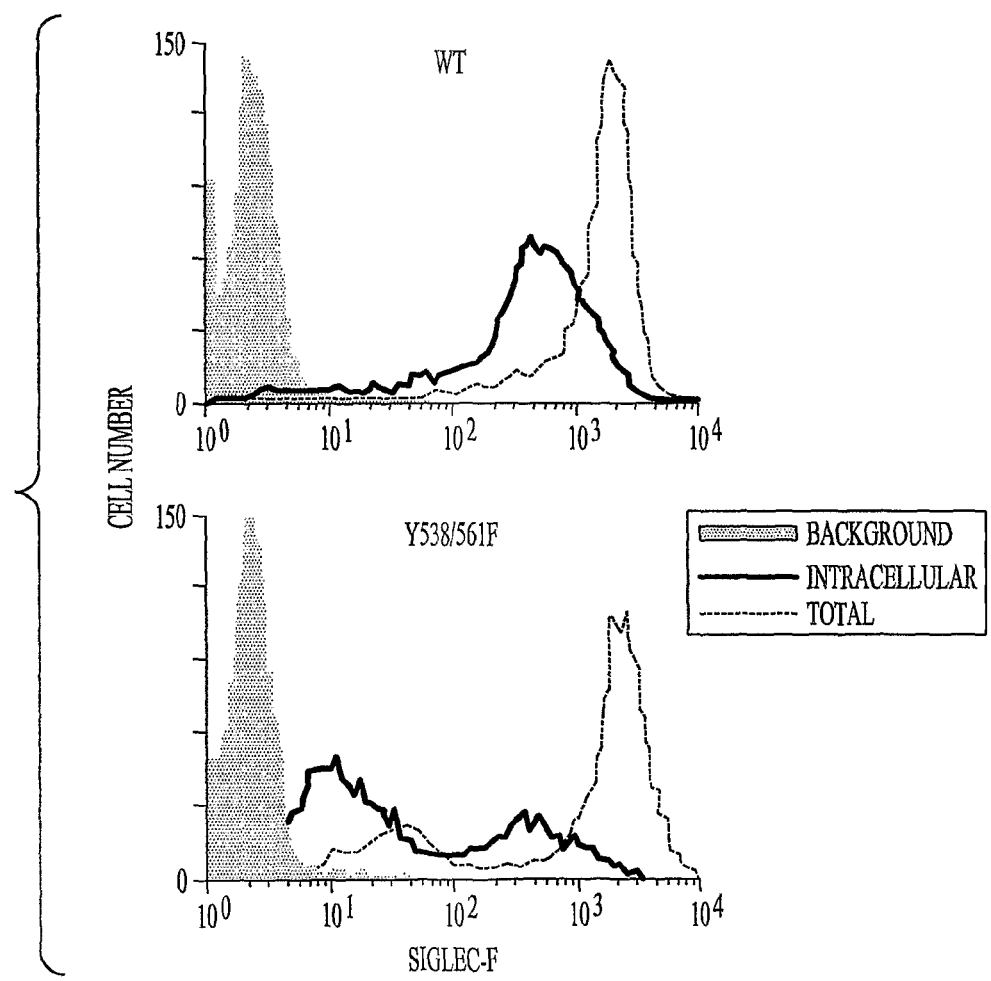
Figure 11C:
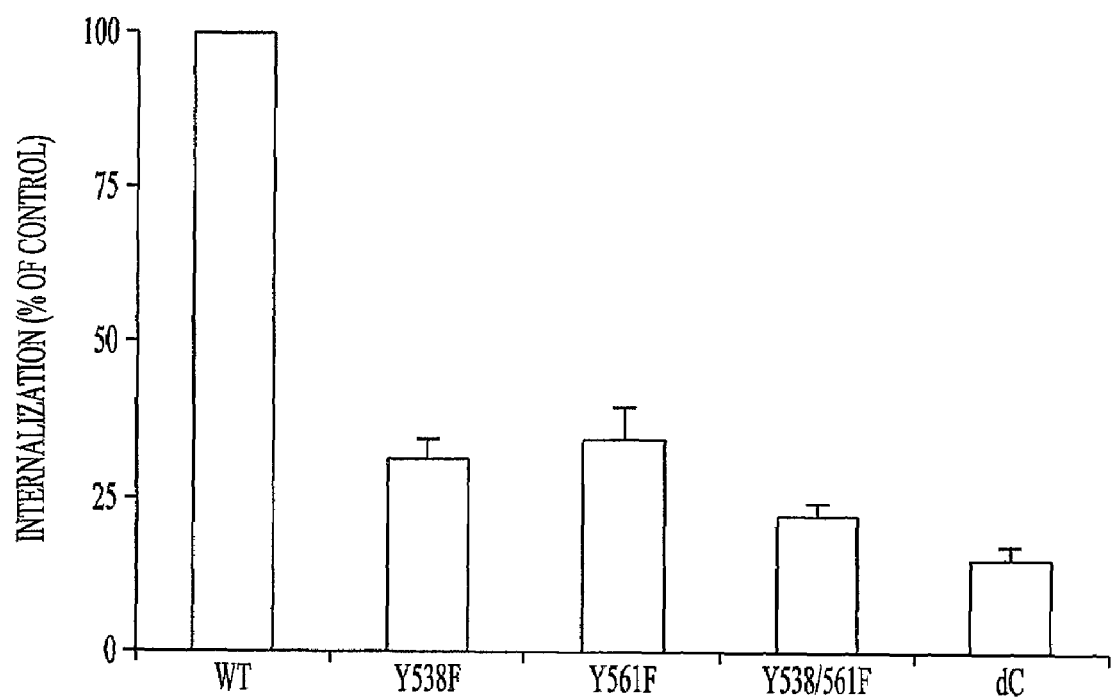

Tyrosine-based motifs are required for endocytosis of Siglec-F. Siglec-F carries two potential cytoplasmic tyrosine-based sorting motifs (YxxL/I) at amino acids 538 and 561. To determine whether the motifs are required for internalization, tyrosine to phenylalanine mutants at 538 and 561, either individually or in combination, and a cytoplasmic deletion mutant, were designed (FIG. 11A). The internalization of mutants was compared to that of wild-type Siglec-F by flow cytometry. Although PE-anti-Siglec-F mAb was efficiently internalized in CHO cells expressing wild-type Siglec-F, the level of internalized antibody was significantly decreased in CHO cells expressing the double tyrosine mutant Y538F and Y561F (FIG. 11B). Mutation of both tyrosine residues to phenylalanine inhibited approx. 80% of internalization (FIG. 11C). The inhibitory effect of the cytoplasmic deletion mutant was similar to that of the double tyrosine mutant Y538F+Y561F (85% inhibition), indicating that the tyrosine-based motifs are the dominant sorting signals. Since single mutation of either Tyr538 or Tyr561 also inhibited endocytosis of Siglec-F (66~69% inhibition), both tyrosine-based motifs are required for endocytosis of Siglec-F.

The residual 15-30% internalization observed when using the cytoplasmic deletion mutant might be due to bulk internalization of plasma membrane. A point mutation which changes a specific arginine residue required for sialoside binding to an inactive alanine (Angata et al., J. Biol. Chem. 276: 45128-36 (2001)) showed no effect on internalization of Siglec-F, suggesting that ligand-binding activity is not directly involved in the endocytosis of Siglec-F, consistent with what has been reported for endocytosis of CD22 (data not shown; see also, Zhang & Varki, Glycobiology 14: 939-49 (2004)).

Development of a high-affinity sialoside probe, which mimics the natural trans-ligand of Siglec-F. The data above show endocytosis of Siglec-F following ligation with antibodies. Similar results were observed for CD22. However, the natural trans-ligands of siglecs are not antibodies, but sialylated glycans. To study endocytosis of a glycan ligand, synthetic multivalent ligands were developed that mimic sialylated antigens. The preferred glycan ligand for Siglec-F is 6'-sulfo-sLe$^x$ (Neu5Acα2-3 [6-SO$_4$]Galβ1-4[Fucα1-3]GlcNAc) (Tateno et al., Glycobiology 15: 1125-35 (2005)). However, Siglec-F may be masked and unable to bind synthetic sialoside probes by cis glycan ligands on the cell surface. To facilitate development of a synthetic glycan ligand and permit assessment of ligand binding, cells can be treated with sialidase to remove cis sialic acid glycans.

Figure 12:
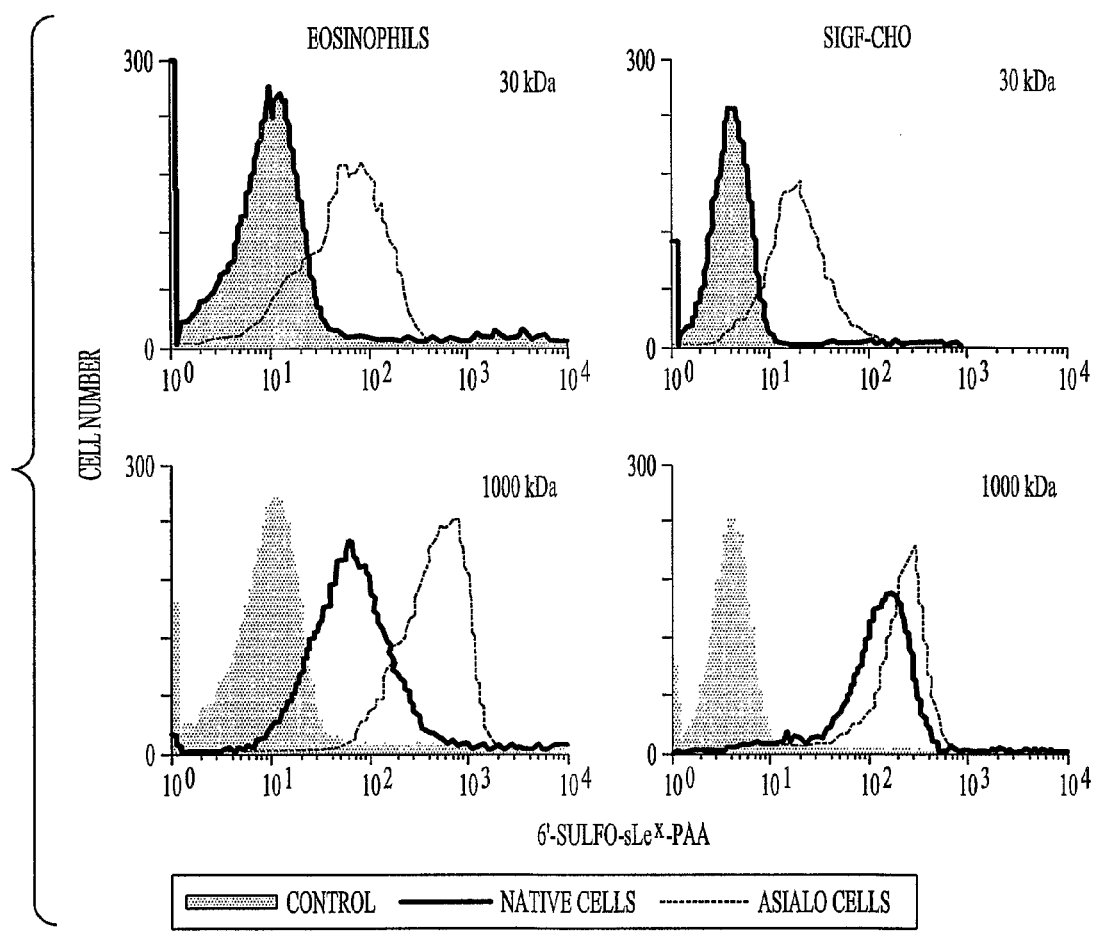
FIG. 12 shows that a high-molecular weight sialoside-probe 6'-sulfo-sLe$^X$-PAA binds to Siglec-F on native cells. Siglec-F binds to glycan ligands having the structure 6'-sulfo-sLe$^X$ but high amounts of natural Siglec-F ligands that are naturally present on cell surfaces (i.e. cis ligands) can mask or prevent binding between cell membrane bound Siglec-F and soluble 6'-sulfo-sLe$^x$ provided in trans. Thus, a carrier (polyacrylamide, PAA) was attached to many 6'-sulfo-sLe$^x$ ligands to generate a multivalent Siglec-F ligand (6'-sulfo-sLe$^X$-PAA). Mouse eosinophils, prepared from IL5-Tg mice or SigF-CHO cells and pretreated with or without *Arthrobacter ureafaciens* sialidase, were incubated with biotinylated 1000 kDa LN-PAA (negative control) or 1000 kDa 6'-sulfo-sLe$^x$-PAA on ice for 60 min. After washing, bound probe was detected with PE-Cy5-streptavidin and analyzed by flow cytometry. As illustrated in the lower right panel, the multivalent 6'-sulfo-sLe$^X$-PAA ligand bound to cells even when cis ligands were not removed with sialidase.

A 6'-sulfo-sLe$^x$ high-affinity glycan ligand was created by attachment of the 6'-sulfo-sLe$^x$ glycan to a high molecular weight polyacrylamide (PAA) backbone to provide a highly multivalent construct. Biotin (5%) was also attached to the PAA to allow detection of PAA-biotin with streptavidin. A standard ELISA assay using immobilized Siglec-F-Fc chimera showed that the resulting 1000 kDa 6'-sulfo-sLe$^x$-PAA-biotin probe bound with much higher binding avidity than did the standard 30 kDa 6'-sulfo-sLe$^x$-PAA-biotin probe (data not shown), indicating that ligand multivalency is critical for the binding avidity of Siglec-F. The 1000 kDa 6'-sulfo-sLe$^x$-PAA-biotin probe was then assessed for its ability to compete with cis ligands by comparing binding to eosinophils and SigF-CHO cells treated with (asialo cells) or without (native cells) sialidase (FIG. 12). Although the 30 kDa probe bound only to the asialo cells, the 1000 kDa probe bound to native cells as well, demonstrating that the 1000 kDa 6'-sulfo-sLe$^x$-PAA-biotin probe can effectively compete with cis ligands on both mouse eosinophils and SigF-CHO cells. Blocking with anti-Siglec-F mAb inhibited binding of the sialoside probe to the cells, indicating that the binding is not due to a nonspecific interaction (Tateno et al., Glycobiology 15: 1125-35 (2005)). No binding of a control 1000 kDa LacNAc (LN)-PAA-biotin probe was observed.

Siglec-F and CD22 mediate endocytosis of glycan ligands. Having developed a high-affinity sialoside probe for Siglec-F that can bind to native cells, the ability of Siglec-F and CD22 to internalize their glycan ligands to intracellular compartments was investigated. The high-affinity 1000 kDa biotinylated 9-biphenylcarbonyl-NeuAcα2-6LN-PAA-biotin (BPC-NeuAc-LN-PAA-biotin) probe was used to study endocytosis of CD22. Cells were incubated with the sialoside-PAA-biotin probe on ice for 60 min followed by incubation with PE-Cy5-streptavidin on ice for 30 min. The cells were then shifted to 37° C. and internalized probe was detected by flow cytometry. Compared to the level at 0 min, the level of internalized 1000 kDa BPC-NeuAc LN-PAA-biotin probe in CD22-CHO cells gradually increased with incubation time at 37° C. Similarly, the 1000 kDa 6'-sulfo-sLe$^x$-PAA-biotin probe was internalized by Siglec-F on SigF-CHO cells. No binding or internalization was observed with the control 1000 kDa LN-PAA-biotin (data not shown). No binding or internalization was observed with either of the following negative controls: the 1000 kDa BPC-NeuAc̄ LN-PAA-biotin or 6'-sulfo-sLe$^x$-PAA-biotin for untransfected CHO cells (data not shown).

EXAMPLE 6

Bi-Functional CD22-α-Gal Ligands

This Example illustrates the synthesis of a hetero-bifunctional CD22-α-Gal ligand that will allow self-assembly between CD22 and anti-Gal IgM antibodies endogenously found in all humans (Tinquely et al., Xenotransplantation 9: 252 (2002)). The structure of the CD22-α-Gal ligand is shown below.

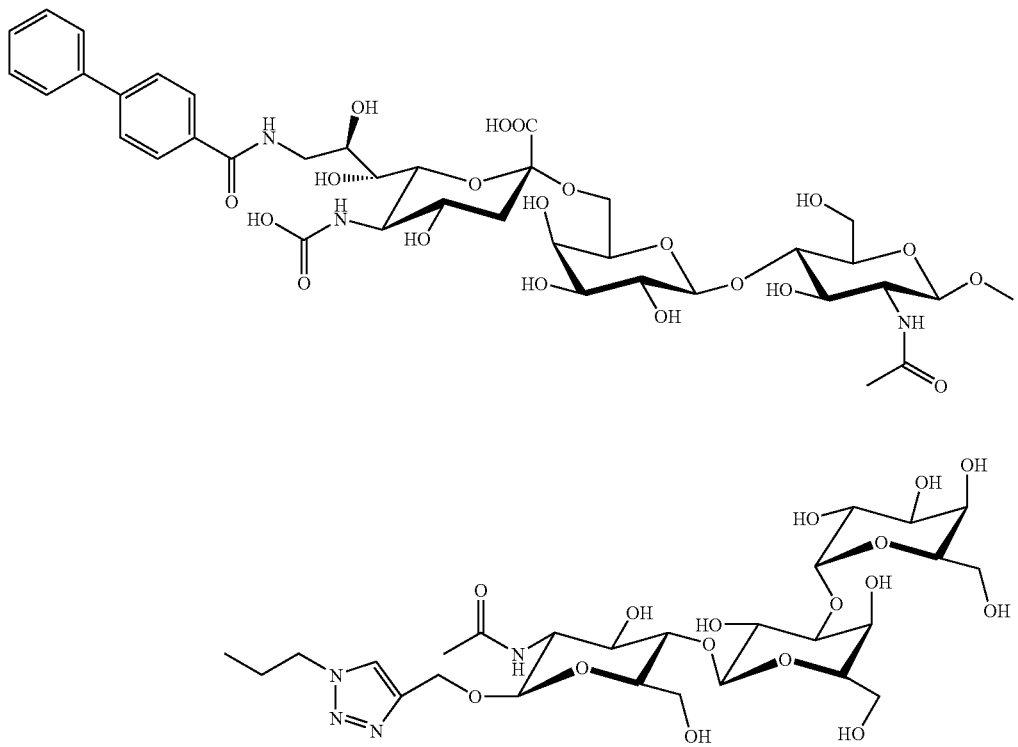

This CD22-α-Gal ligand has a CD22 ligand (R$_9$-NeuAc-α(2,6)-Galβ(1,4)-GlcNAc, shown as the left half of the above structure) and an α-Gal antigen (shown as the light half of the above structure). The CD22 ligand is covalently linked through a 1,4-triazole moiety to the α-Gal epitope.

As shown in previous Examples, the CD22 ligand is efficiently bound to cells that display CD22, especially when a multivalent version of the CD22 ligand is used where several copies of the CD22 ligand are bound to a single carrier molecule.

In this Example, the CD22-α-Gal ligand is designed to self-assemble in vivo using anti-α-Gal antibodies as a carrier because such anti-α-Gal antibodies are endogenously present in all humans. When the CD22-α-Gal ligand-antibody complex binds to CD22-expressing cells, the CD22-expressing cells are killed by the immune system, through activation of serum complement factors, and opsonization of antibody-CD22 complex. Opsonization is the process whereby opsonins make an invading microorganism more susceptible to phagocytosis. An opsonin is an antibody in blood serum that attaches to invading microorganisms and other antigens to make them more susceptible to the action of phagocytes. Here, the α-Gal portion of the ligand is an antigen normally found on bacteria and not found in human tissues. Since, essentially all humans have been exposed to bacteria and have developed antibodies against the α-Gal bacterial antigen, the CD22-α-Gal ligand-antibody complex bound to CD22-expressing cells will, in essence, be treated as an invading bacterium, and the immune system will destroy the CD22 cells. As described herein, this CD22-α-Gal ligand is designed to be a therapeutic agent for treating leukemia and other B-cell conditions because CD22 is a B cell marker.

The two tri-saccharide building blocks shown below will be chemo-enzymatically synthesized using procedures described in Chen et al., Production of α-Galactosyl Epitopes via Combined Use of Two Recombinant Whole Cells Harboring UDP-Galactose 4-Epimerase and α-1,3-Galactosyl-transferase, Biotechnol. Prog. 16: 595-599 (2000)(incorporated herein by reference). The final coupling of the two trisaccharides will be achieved through a Cu(I) catalyzed 1,3-dipolar Huisgen reaction ("click chemistry") as described in Kolb et al., *The growing impact of click chemistry on drug discovery*, Drug Discovery Today 8: 1128-37 (2003).

complement, opsonization of antibody-CD22 complex as well as antibody-dependent cell-mediated cytotoxicity (ADCC) of natural killer (NK) lymphocytes is expected to lead to efficient BJAB cell killing. An anti-cancer drug will therefore be developed for targeting B-cell leukemia and lymphomas.

References:

Aikawa, Y., and T. F. Martin. 2003. ARF6 regulates a plasma membrane pool of phosphatidylinositol(4,5)bisphosphate required for regulated exocytosis. *J. Cell Biol.* 162:647-59.

Angata, T., R. Hingorani, N. M. Varki, and A. Varki. 2001. Cloning and characterization of a novel mouse Siglec, mSiglec-F: differential evolution of the mouse and human (CD33) Siglec-3-related gene clusters. *J Biol. Chem.* 276: 45128-36.

Arnaoutova, I., C. L. Jackson, O. S. Al-Awar, J. G. Donaldson, and Y. P. Loh. 2003. Recycling of Raft-associated prohormone sorting receptor carboxypeptidase E requires interaction with ARF6. *Mol Biol Cell.* 14:4448-57.

Augustin, R., J. Riley, and K. H. Moley. 2005. GLUT8 contains a [DE]XXXL[LI] sorting motif and localizes to a late endosomal/lysosomal compartment. *Traffic.* 6:1196-212.

Bakker, T. R., Piperi, C., Davies, E. A. & Merwe, P. A. Comparison of CD22 binding to native CD45 and synthetic oligosaccharide. *Eur J Immunol* 32, 1924-1932 (2002).

Blixt, O., Collins, B. E., van den Nieuwenhof, I. M., Crocker, P. R. & Paulson, J. C. Sialoside specificity of the siglec family assessed using novel multivalent probes: identification of potent inhibitors of myelin-associated glycoprotein. *J Biol Chem* 278, 31007-31019 (2003).

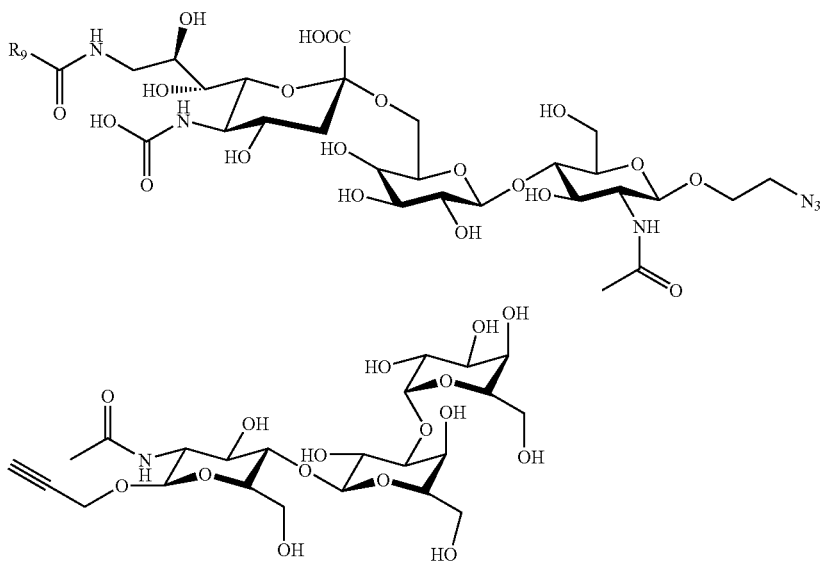

An ELISA type assay will be used to determine the binding affinity of the CD22-α-Gal ligand to recombinant a CD22-Fc chimera. Cell binding experiments will be performed on asialo-, sialo-human lymphoma BJAB cells as well as native B cells. Binding will be detected by flow cytometry and studies will be performed to ascertain whether the CD22-α-Gal ligand can compete with, and displace cis CD22 ligands that are naturally present on CD22-expressing cells.

Anti-Gal mediated cell killing will be evaluated with BJAB cells in the medium of human blood. A combination of anti-Gal mediated effector functions, such as activation of serum Bochner, B. S., R. A. Alvarez, P. Mehta, N. V. Bovin, O. Blixt, J. R. White, and R. L. Schnaar. 2005. Glycan array screening reveals a candidate ligand for Siglec-8. *J Biol. Chem.* 280:4307-12.

Brinkman-Van der Linden, E. C. et al. Loss of N-glycolylneuraminic acid in human evolution. Implications for sialic acid recognition by siglecs. *J Biol Chem* 275, 8633-8640 (2000).

Brown, F. D., A. L. Rozelle, H. L. Yin, T. Balla, and J. G. Donaldson. 2001. Phosphatidylinositol 4,5-bisphosphate and Arf6-regulated membrane traffic. *J. Cell Biol.* 154: 1007-17.

Chan, C. H., J. Wang, R. R. French, and M. J. Glennie. 1998. Internalization of the lymphocytic surface protein CD22 is controlled by a novel membrane proximal cytoplasmic motif. *J Biol. Chem.* 273:27809-15.

Chava, A. K., S. Bandyopadhyay, M. Chatterjee, and C. Mandal. 2004. Sialoglycans in protozoal diseases: their detection, modes of acquisition and emerging biological roles. *Glycoconj J.* 20:199-206.

Coleman, M. et al. Epratuzumab: targeting B-cell malignancies through CD22. *Clin Cancer Res* 9, 3991β-3994S (2003).

Collins, B. E. et al. Constitutively unmasked CD22 on B cells of ST6Gal I knockout mice: novel sialoside probe for murine CD22. *Glycobiology* 12, 563-571 (2002).

Collins, B. E. et al. Masking of CD22 by cis ligands does not prevent redistribution of CD22 to sites of cell contact. *Proc Natl Acad Sci USA* 101, 6104-6109 (2004).

Collins, B. E., B. A. Smith, P. Bengtson, and J. C. Paulson. 2006. Ablation of CD22 in ligand-deficient mice restores B cell receptor signaling. *Nat. Immunol.* 7:199-206.

Conner, S. D., and S. L. Schmid. 2003. Regulated portals of entry into the cell. *Nature.* 422:37-44.

Cornall, R. J. et al. Polygenic autoimmune traits: Lyn, CD22, and SHP-1 are limiting elements of a biochemical pathway regulating BCR signaling and selection. *Immunity* 8, 497-508 (1998).

Crocker, P. R. Siglecs: sialic-acid-binding immunoglobulin-like lectins in cell-cell interactions and signaling. *Curr Opin Struct Biol* 12, 609-615 (2002).

Crocker, P. R. Siglecs in innate immunity. *Curr Opin Pharmacol* 5, 431-437 (2005).

Cyster, J. G. & Goodnow, C. C. Tuning antigen receptor signaling by CD22: integrating cues from antigens and the microenvironment. *Immunity* 6, 509-517 (1997).

Damke, H., D. D. Binns, H. Ueda, S. L. Schmid, and T. Baba. 2001. Dynamin GTPase domain mutants block endocytic vesicle formation at morphologically distinct stages. *Mol Biol Cell.* 12:2578-89.

Del Pozo, V., B. De Andres, E. Martin, B. Cardaba, J. C. Fernandez, S. Gallardo, P. Tramon, F. Leyva-Cobian, P. Palomino, and C. Lahoz. 1992. Eosinophil as antigen-presenting cell: activation of T cell clones and T cell hybridoma by eosinophils after antigen processing. *Eur J Immunol.* 22:1919-25.

Delputte, P. L., and H. J. Nauwynck. 2004. Porcine arterivirus infection of alveolar macrophages is mediated by sialic acid on the virus. *J. Virol.* 78:8094-101.

Doody, G. M. et al. A role in B cell activation for CD22 and the protein tyrosine phosphatase SHP. *Science* 269, 242-244 (1995).

Floyd, H., J. Ni, A. L. Cornish, Z. Zeng, D. Liu, K. C. Carter, J. Steel, and P. R. Crocker. 2000. Siglec-8. A novel eosinophil-specific member of the immunoglobulin superfamily. *J Biol. Chem.* 275:861-6.

Gambaryan, A. S., E. Y. Boravleva, T. Y. Matrosovich, M. N. Matrosovich, H. D. Klenk, E. V. Moiseeva, A. B. Tuzikov, A. A. Chinarev, G. V. Pazynina, and N. V. Bovin. 2005. Polymer-bound 6' sialyl-N-acetyllactosamine protects mice infected by influenza virus. *Antiviral Res.* 68:116-23.

Ghetie, M. A., R. D. May, M. Till, J. W. Uhr, V. Ghetie, P. P. Knowles, M. Relf, A. Brown, P. M. Wallace, G. Janossy, and et al. 1988. Evaluation of ricin A chain-containing immunotoxins directed against CD19 and CD22 antigens on normal and malignant human B-cells as potential reagents for in vivo therapy. *Cancer Res.* 48:2610-7.

Ghobrial, I. & Witzig, T. Radioimmunotherapy: a new treatment modality for B cell non-Hodgkin's lymphoma. *Oncology (Williston Park)* 18, 623-630; discussion 633-624, 637-628, 640 (2004).

Glebov, O. O., N. A. Bright, and B. J. Nichols. 2006. Flotillin-1 defines a clathrin-independent endocytic pathway in mammalian cells. *Nat Cell Biol.* 8:46-54.

Han, S., B. E. Collins, P. Bengtson, and J. C. Paulson. 2005. Homomultimeric complexes of CD22 in B cells revealed by protein-glycan cross-linking. *Nat Chem Biol.* 1:93-7.

Hanasaki, K., Powell, L. D. & Varki, A. Binding of human plasma sialoglycoproteins by the B cell-specific lectin CD22. Selective recognition of immunoglobulin M and haptoglobin. *J Biol Chem* 270, 7543-7550 (1995).

Handzel, Z. T., W. W. Busse, J. B. Sedgwick, R. Vrtis, W. M. Lee, E. A. Kelly, and J. E. Gern. 1998. Eosinophils bind rhinovirus and activate virus-specific T cells. *J Immunol.* 160:1279-84.

Henley, J. R., E. W. Krueger, B. J. Oswald, and M. A. McNiven. 1998. Dynamin-mediated internalization of caveolae. *J. Cell Biol.* 141:85-99.

John, B., B. R. Herrin, C. Raman, Y. N. Wang, K. R. Bobbitt, B. A. Brody, and L. B. Justement. 2003. The B cell coreceptor CD22 associates with AP50, a clathrin-coated pit adapter protein, via tyrosine-dependent interaction. *J Immunol.* 170:3534-43.

Jones, C., M. Virji, and P. R. Crocker. 2003. Recognition of sialylated meningococcal lipopolysaccharide by siglecs expressed on myeloid cells leads to enhanced bacterial uptake. *Mol Microbiol.* 49:1213-25.

Juweid, M. Technology evaluation: epratuzumab, Immunomedics/Amgen. *Curr Opin Mol Ther* 5, 192-198 (2003).

Kelm, S. et al. Sialoadhesin, myelin-associated glycoprotein and CD22 define a new family of sialic acid-dependent adhesion molecules of the immunoglobulin superfamily. *Curr Biol* 4, 965-972 (1994).

Kelm, S., Gerlach, J., Brossmer, R., Danzer, C. P. & Nitschke, L. The ligand binding domain of CD22 is needed for inhibition of the B cell receptor signal, as demonstrated by a novel human CD22-specific inhibitor compound. *J Exp Med* 195, 1207-1213 (2002).

Kikly, K. K., B. S. Bochner, S. D. Freeman, K. B. Tan, K. T. Gallagher, J. D'Alessio K, S. D. Holmes, J. A. Abrahamson, C. L. Erickson-Miller, P. R. Murdock, H. Tachimoto, R. P. Schleimer, and J. R. White. 2000. Identification of SAF-2, a novel siglec expressed on eosinophils, mast cells, and basophils. *J Allergy Clin Immunol.* 105:1093-100.

Lanoue, A., Batista, F. D., Stewart, M. & Neuberger, M. S. Interaction of CD22 with alpha2,6-linked sialoglycoconjugates: innate recognition of self to dampen B cell autoreactivity? *Eur J Immunol* 32, 348-355 (2002).

Le, P. U., G. Guay, Y. Altschuler, and I. R. Nabi. 2002. Caveolin-1 is a negative regulator of caveolae-mediated endocytosis to the endoplasmic reticulum. *J Biol Chem.* 277:3371-9.

Lee, N. A., M. P. McGarry, K. A. Larson, M. A. Horton, A. B. Kristensen, and J. J. Lee. 1997. Expression of IL-5 in thymocytes/T cells leads to the development of a massive eosinophilia, extramedullary eosinophilopoiesis, and unique histopathologies. *J Immunol.* 158:1332-44.

Leonard, J. P. et al. Epratuzumab, a humanized anti-CD22 antibody, in aggressive non-Hodgkin's lymphoma: phase I/II clinical trial results. *Clin Cancer Res* 10, 5327-5334 (2004).

Leonard, J. P. et al. Combination antibody therapy with epratuzumab and rituximab in relapsed or refractory non-Hodgkin's lymphoma. *J Clin Oncol* 23, 5044-5051 (2005).

Lizee, G., G. Basha, J. Tiong, J. P. Julien, M. Tian, K. E. Biron, and W. A. Jefferies. 2003. Control of dendritic cell cross-presentation by the major histocompatibility complex class I cytoplasmic domain. *Nat. Immunol.* 4:1065-73.

Mawhorter, S. D., J. W. Kazura, and W. H. Boom. 1994. Human eosinophils as antigen-presenting cells: relative efficiency for superantigen- and antigen-induced CD4+ T-cell proliferation. *Immunology.* 81:584-91.

Mochalova, L., A. Gambaryan, J. Romanova, A. Tuzikov, A. Chinarev, D. Katinger, H. Katinger, A. Egorov, and N. Bovin. 2003. Receptor-binding properties of modem human influenza viruses primarily isolated in Vero and MDCK cells and chicken embryonated eggs. *Virology.* 313:473-80.

Monteiro, V. G., C. S. Lobato, A. R. Silva, D. V. Medina, M. A. de Oliveira, S. H. Seabra, W. de Souza, and R. A. DaMatta. 2005. Increased association of Trypanosoma cruzi with sialoadhesin positive mice macrophages. *Parasitol Res.* 97:380-5.

Mukherjee, S., R. N. Ghosh, and F. R. Maxfield. 1997. Endocytosis. *Physiol Rev.* 77:759-803.

Monteiro, V. G., C. S. Lobato, A. R. Silva, D. V. Medina, M. A. de Oliveira, S. H. Seabra, W. de Souza, and R. A. DaMatta. 2005. Increased association of *Trypanosoma cruzi* with sialoadhesin positive mice macrophages. *Parasitol Res.* 97:380-5.

Mukherjee, S., R. N. Ghosh, and F. R. Maxfield. 1997. Endocytosis. *Physiol Rev.* 77:759-803.

Nakamura, K., T. Yamaji, P. R. Crocker, A. Suzuki, and Y. Hashimoto. 2002. Lymph node macrophages, but not spleen macrophages, express high levels of unmasked sialoadhesin: implication for the adhesive properties of macrophages in vivo. *Glycobiology.* 12:209-16.

Naslavsky, N., R. Weigert, and J. G. Donaldson. 2003. Convergence of non-clathrin- and clathrin-derived endosomes involves Arf6 inactivation and changes in phosphoinositides. *Mol Biol Cell.* 14:417-31.

Naslavsky, N., R. Weigert, and J. G. Donaldson. 2004. Characterization of a nonclathrin endocytic pathway: membrane cargo and lipid requirements. *Mol Biol Cell.* 15:3542-52.

Nitschke, L., R. Carsetti, B. Ocker, G. Kohler, and M. C. Lamers. 1997. CD22 is a negative regulator of B-cell receptor signalling. *Curr Biol.* 7:133-43. Nitschke, L., and T. Tsubata. 2004. Molecular interactions regulate BCR signal inhibition by CD22 and CD72. *Trends Immunol.* 25:543-50.

Nutku, E., H. Aizawa, S. A. Hudson, and B. S. Bochner. 2003. Ligation of Siglec-8: a selective mechanism for induction of human eosinophil apoptosis. *Blood.* 101:5014-20.

Oh, P., D. P. McIntosh, and J. E. Schnitzer. 1998. Dynamin at the neck of caveolae mediates their budding to form transport vesicles by GTP-driven fission from the plasma membrane of endothelium. *J. Cell Biol.* 141:101-14.

O'Keefe, T. L., Williams, G. T., Davies, S. L. & Neuberger, M. S. Hyperresponsive B cells in CD22-deficient mice. *Science* 274, 798-801 (1996).

Otipoby, K. L. et al. CD22 regulates thymus-independent responses and the lifespan of B cells. *Nature* 384, 634-637 (1996).

Pelkmans, L., T. Burli, M. Zerial, and A. Helenius. 2004. Caveolin-stabilized membrane domains as multifunctional transport and sorting devices in endocytic membrane traffic. *Cell.* 118:767-80.

Pelkmans, L., J. Kartenbeck, and A. Helenius. 2001. Caveolar endocytosis of simian virus 40 reveals a new two-step vesicular-transport pathway to the ER. *Nat Cell Biol.* 3:473-83.

Powell, L. D., Jain, R. K., Matta, K. L., Sabesan, S. & Varki, A. Characterization of sialyloligosaccharide binding by recombinant soluble and native cell-associated CD22. Evidence for a minimal structural recognition motif and the potential importance of multisite binding. *J Biol Chem* 270, 7523-7532 (1995).

Prekeris, R., B. Yang, V. Oorschot, J. Klumperman, and R. H. Scheller. 1999. Differential roles of syntaxin 7 and syntaxin 8 in endosomal trafficking. *Mol Biol Cell.* 10:3891-908.

Qu, Z. et al. Development of humanized antibodies as cancer therapeutics. *Methods* 36, 84-95 (2005).

Radhakrishna, H., and J. G. Donaldson. 1997. ADP-ribosylation factor 6 regulates a novel plasma membrane recycling pathway. *J. Cell Biol.* 139:49-61.

Razi, N., and A. Varki. 1998. Masking and unmasking of the sialic acid-binding lectin activity of CD22 (Siglec-2) on B lymphocytes. *Proc Natl Acad Sci USA.* 95:7469-74.

Razi, N., and A. Varki. 1999. Cryptic sialic acid binding lectins on human blood leukocytes can be unmasked by sialidase treatment or cellular activation. *Glycobiology.* 9:1225-34.

Rothenberg, M. E., and S. P. Hogan. 2006. The eosinophil. *Annu Rev Immunol.* 24:147-74.

Santos, S. G., A. N. Antoniou, P. Sampaio, S. J. Powis, and F. A. Arosa. 2006. Lack of Tyrosine 320 Impairs Spontaneous Endocytosis and Enhances Release of HLA-B27 Molecules. *J Immunol.* 176:2942-9.

Sato, S. et al. CD22 is both a positive and negative regulator of B lymphocyte antigen receptor signal transduction: altered signaling in CD22-deficient mice. *Immunity* 5, 551-562 (1996).

Sato, S., J. M. Tuscano, M. Inaoki, and T. F. Tedder. 1998. CD22 negatively and positively regulates signal transduction through the B lymphocyte antigen receptor. *Semin Immunol.* 10:287-97.

Sgroi, D., Varki, A., Braesch-Andersen, S. & Stamenkovic, 1. CD22, a B cell specific immunoglobulin superfamily member, is a sialic acid-binding lectin. *J Biol Chem* 268, 7011-7018 (1993).

Shi, H. Z. 2004. Eosinophils function as antigen-presenting cells. *J Leukoc Biol.* 76:520-7.

Shi, H. Z., A. Humbles, C. Gerard, Z. Jin, and P. F. Weller. 2000. Lymph node trafficking and antigen presentation by endobronchial eosinophils. *J Clin Invest.* 105:945-53.

Sigismund, S., T. Woelk, C. Puri, E. Maspero, C. Tacchetti, P. Transidico, P. P. Di Fiore, and S. Polo. 2005. Clathrin-independent endocytosis of ubiquitinated cargos. *Proc Natl Acad Sci USA.* 102:2760-5.

Signoret, N., L. Hewlett, S. Wavre, A. Pelchen-Matthews, M. Oppermann, and M. Marsh. 2005. Agonist-induced endocytosis of CC chemokine receptor 5 is clathrin dependent. *Mol Biol Cell.* 16:902-17.

Sliedregt, L. A. et al. Design and synthesis of a multivalent homing device for targeting to murine CD22. *Bioorg Med Chem* 9, 85-97 (2001).

Tateno, H., P. R. Crocker, and J. C. Paulson. 2005. Mouse Siglec-F and human Siglec-8 are functionally convergent paralogs that are selectively expressed on eosinophils and recognize 6'-sulfo-sialyl Lewis X as a preferred glycan ligand. *Glycobiology.* 15:1125-35.

Tedder, T. F., J. C. Poe, and K. M. Haas. 2005. CD22: A Multifunctional Receptor That Regulates B Lymphocyte Survival and Signal Transduction. *Adv Immunol.* 88:1-50.

Tuscano, J. M., R. T. O'Donnell, L. A. Miers, L. A. Kroger, D. L. Kukis, K. R. Lamborn, T. F. Tedder, and G. L. DeNardo. 2003. Anti-CD22 ligand-blocking antibody HB22.7 has independent lymphoinacidal properties and augments the efficacy of 90Y-DOTA-peptide-Lym-1 in lymphoma xenografts. *Blood.* 101:3641-7.

Uthayakumar, S., and B. L. Granger. 1995. Cell surface accumulation of overexpressed hamster lysosomal membrane glycoproteins. *Cell Mol Biol Res.* 41:405-20.

Vanderheijden, N., P. L. Delputte, H. W. Favoreel, J. Vandekerckhove, J. Van Damme, P. A. van Woensel, and H. J. Nauwynck. 2003. Involvement of sialoadhesin in entry of porcine reproductive and respiratory syndrome virus into porcine alveolar macrophages. *J Virol.* 77:8207-15.

van Rossenberg, S. M. et al. A structure-function study of ligand recognition by CD22beta. *J Biol Chem* 276, 12967-12973 (2001).

Varki, A., and T. Angata. 2006. Siglecs—the major subfamily of I-type lectins. *Glycobiology.* 16: 1R-27R.

Vimr, E. R., K. A. Kalivoda, E. L. Deszo, and S. M. Steenbergen. 2004. Diversity of microbial sialic acid metabolism. *Microbiol. Mol Biol Rev.* 68:132-53.

Vitetta, E. S., M. Stone, P. Amlot, J. Fay, R. May, M. Till, J. Newman, P. Clark, R. Collins, D. Cunningham, and et al. 1991. Phase I immunotoxin trial in patients with B-cell lymphoma. *Cancer Res.* 51:4052-8.

Vivier, E., and M. Daeron. 1997. Immunoreceptor tyrosine-based inhibition motifs. *Immunol Today.* 18:286-91.

Wakarchuk, W., A. Martin, M. P. Jennings, E. R. Moxon, and J. C. Richards. 1996. Functional relationships of the genetic locus encoding the glycosyltransferase enzymes involved in expression of the lacto-N-neotetraose terminal lipopolysaccharide structure in *Neisseria meningitidis*. *J Biol. Chem.* 271:19166-73.

Walter, R. B., B. W. Raden, D. M. Kamikura, J. A. Cooper, and I. D. Bernstein. 2005. Influence of CD33 expression levels and ITIM-dependent internalization on gemtuzumab ozogamicin-induced cytotoxicity. *Blood.* 105:1295-302.

Weller, P. F., T. H. Rand, T. Barrett, A. Elovic, D. T. Wong, and R. W. Finberg. 1993. Accessory cell function of human eosinophils. HLA-DR-dependent, MHC-restricted antigen-presentation and IL-1 alpha expression. *J Immunol.* 150:2554-62.

Yamashiro, D. J., B. Tycko, S. R. Fluss, and F. R. Maxfield. 1984. Segregation of transferrin to a mildly acidic (pH 6.5) para-Golgi compartment in the recycling pathway. *Cell.* 37:789-800.

Yang, Z. Q., Puffer, E. B., Pontrello, J. K. & Kiessling, L. L. Synthesis of a multivalent display of a CD22-binding trisaccharide. *Carbohydr. Res.* 337: 1605-1613 (2002).

Zaccai, N. R. et al. Structure-guided design of sialic acid-based Siglec inhibitors and crystallographic analysis in complex with sialoadhesin. *Structure (Camb)* 11, 557-567 (2003).

Zhang, J., A. Raper, N. Sugita, R. Hingorani, M. Salio, M. J. Palmowski, V. Cerundolo, and P. R. Crocker. 2006. Characterisation of Siglec-H as a novel endocytic receptor expressed on murine plasmacytoid dendritic cell precursors. *Blood.*

Zhang, J. Q., B. Biedermann, L. Nitschke, and P. R. Crocker. 2004. The murine inhibitory receptor mSiglec-E is expressed broadly on cells of the innate immune system whereas mSiglec-F is restricted to eosinophils. *Eur J Immunol.* 34:1175-84.

Zhang, M., and A. Varki. 2004. Cell surface sialic acids do not affect primary CD22 interactions with CD45 and surface IgM nor the rate of constitutive CD22 endocytosis. *Glycobiology.* 14:939-49.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A compound of formula Ia, Ib, Ic or Id:

[R$_9$-Sia-Sac-Y]$_n$-Carrier     Ia

[R$_9$-Sia-Sac-Y]$_n$~Carrier     Ib

[R$_5$-Sia-Sac-Y]$_n$-Carrier     Ic

[R$_5$-Sia-Sac-Y]$_n$~Carrier     Id wherein:
   R$_5$ and R$_9$ are independently each a hydrogen, hydroxyl, acetylamine, alkyl, alkylamide, cycloalkyl, heteroalkyl, cycloheteroalkyl, aryl, arylalkyl, arylamide or heteroaryl group that can be substituted with one to five alkyl, halo, sulfate or hydroxy groups and R5 and R9 are attached to different positions on the Sia;
   Sia is a sialic acid;
   Sac is a neutral saccharide;
   Y is a covalent bond to Carrier, a linker that can be attached to Carrier or an antigen that can bind to an antibody Carrier;
   the symbol ~ is a non-covalent bond;
   n is an integer of 5 or more; and
   Carrier is a polymer, protein, antibody, antigen, multisubunit protein, protein complex, glycan, lipid, liposome or solid support; and
   wherein at least one of R$_5$ or R$_9$ is an alkyl, alkylamide, cycloalkyl, heteroalkyl, cycloheteroalkyl, aryl, arylalkyl, arylamide or heteroaryl group that can be substituted with one to five alkyl, halo, or sulfate groups.

2. The compound of claim 1, wherein R$_5$ or R$_9$ is an aryl, arylalkyl, arylamide or heteroaryl group.

3. The compound of claim 2, wherein the aryl, arylalkyl, arylamide or heteroaryl group comprises a phenyl ring, a bicyclic ring, or tricyclic ring, with about five to about fourteen ring atoms in which at least one ring is aromatic.

4. The compound of claim 2, wherein the aryl, arylalkyl, arylamide or heteroaryl group comprises a phenyl, biphenyl, naphthalene, anthracene, or a combination thereof.

5. The compound of claim 1, wherein the sialic acid is N-acetylneuraminic acid (Neu5Ac) or N-glycolylneuraminic acid (Neu5Gc).

6. The compound of claim 1, wherein the carrier is a polymer.

7. The compound of claim 1, wherein Y is an antigen.

8. The compound of claim 7, wherein the antigen comprises Galα1-3Gal or nitrophenyl.

9. The compound of claim 1, wherein the carrier is an antibody.

10. The compound of claim 9, wherein the antibody is an IgM antibody.

11. The compound of claim 1, wherein the carrier is polyacrylamide, ROMP, TRIS, amyloid serum protein, glycoprotein or liposome.

12. The compound of claim 1, wherein at least one compound of formula Ia or Ic is covalently attached to the carrier.

13. The compound of claim 1, wherein at least one compound of formula Ib or Id binds to the carrier through non-covalent interactions.

14. A compound of formula IIa or IIb:

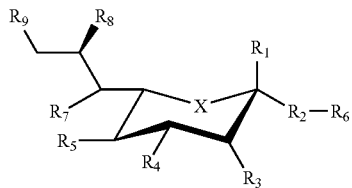

IIa

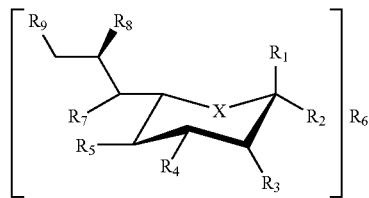

IIb wherein:
X is a methylene or a heteroatom;
R$_1$ is a carboxylate, carboxy, phosphate or sulfate;
R$_2$ is a sugar;
R$_3$, R$_4$, R$_7$ and R$_8$ are each independently a hydrogen, a hydroxyl or an acetylamine;
R$_5$ is a hydrogen, hydroxyl, acetylamine, alkyl, alkylamide, cycloalkyl, heteroalkyl, cycloheteroalkyl, aryl, arylalkyl, arylamide or heteroaryl group that can be substituted with one to five alkyl, halo, or sulfate group;
R$_6$ is hydrogen, a Y group, an alkyl, or a carrier;
Y is a linker that can be attached to a carrier or an antigen that can bind to an antibody carrier; and
R$_9$ is a hydrogen, hydroxyl, alkyl, alkylamide, cycloalkyl, heteroalkyl, cycloheteroalkyl, aryl, arylalkyl, arylamide or heteroaryl group that can be substituted with one to five alkyl, halo, sulfate or hydroxy group; and wherein at least one of R$_5$ or R$_9$ is an alkyl, alkylamide, cycloalkyl, heteroalkyl, cycloheteroalkyl, aryl, arylalkyl, arylamide or heteroaryl group that can be substituted with one to five alkyl, halo, or sulfate groups.

15. The compound of claim 14, wherein the $R_2$ and $R_6$ substituents are joined by a linker.

16. The compound of claim 14, wherein $R_6$ is a non-covalently associated carrier.

17. The compound of claim 14, wherein the aryl is a phenyl ring, a bicyclic ring, or tricyclic ring that has about five to about fourteen ring atoms and where the aryl has at least one aromatic ring.

18. The compound of claim 14, wherein the aryl is phenyl, biphenyl, naphthalene, anthracene, or a combination thereof.

19. The compound of claim 14, wherein the sugar has formula IIa or IIIb:

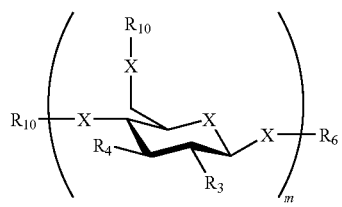

IIIa

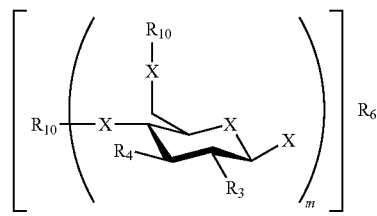

IIIb wherein:
X is methylene or a heteroatom;
$R_3$ and $R_4$ are each independently a hydrogen, a hydroxyl or a acetylamine;
$R_6$ is hydrogen, a Y group, an alkyl, or a carrier;
m is an integer of from 1 to 10; and
each $R_{10}$ is sugar residue, a saccharide or [Ar-Sia], wherein Ar is a bulky aryl group that can be substituted with one to five alkyl groups; and Sia is a sialic acid; and wherein at least one $R_{10}$ is [Ar-Sia].

20. A compound selected from the group consisting of:

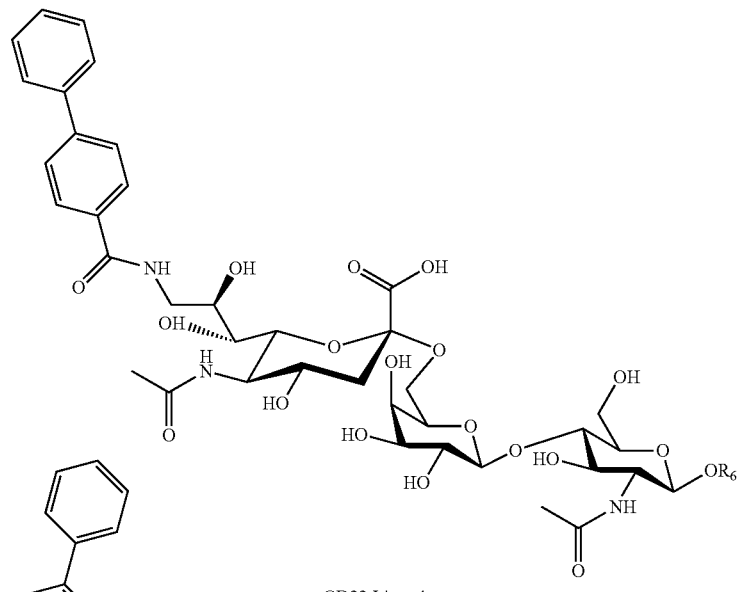

CD22 Ligand

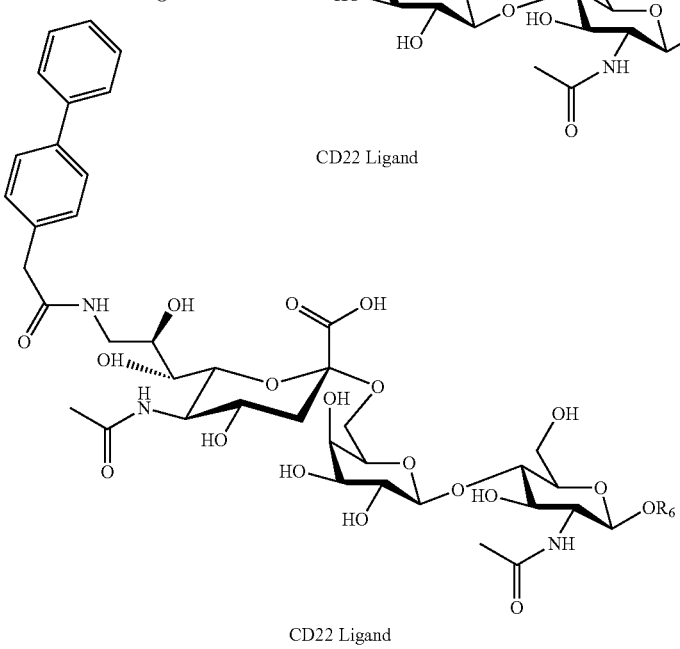

CD22 Ligand

-continued
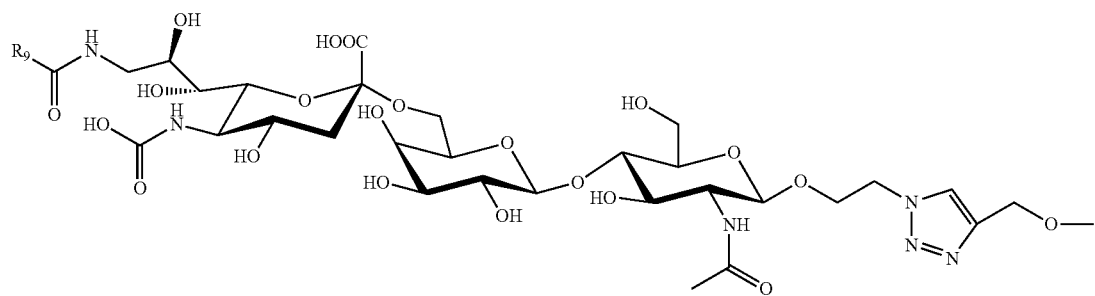
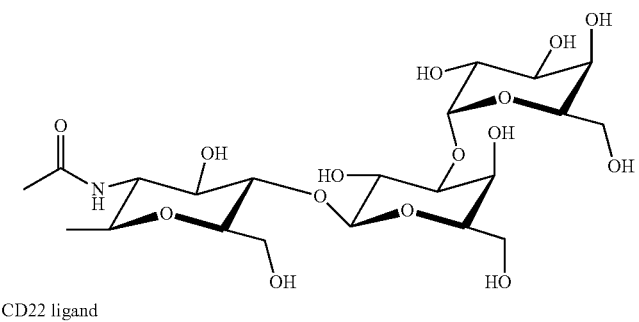
CD22 ligand
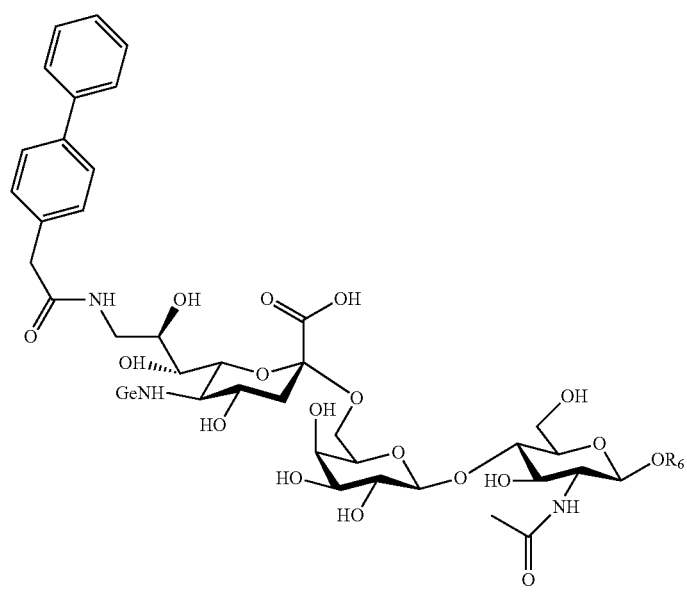
CD22 Ligand wherein:

R$_6$ is hydrogen, a Y group, an alkyl, or a carrier;

Y is a covalent bond to Carrier, a linker that can be attached to Carrier or an antigen that can bind to an antibody Carrier; and R$_9$ is an alkyl, alkylamide, cycloalkyl, heteroalkyl, cycloheteroalkyl, aryl, arylalkyl, arylamide or heteroaryl group that can be substituted with one to five alkyl, halo, sulfate or hydroxy groups.

21. A compound comprising the following formula:

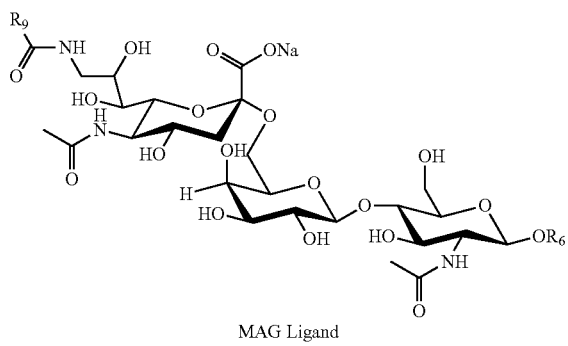

MAG Ligand wherein:

R$_6$ is hydrogen, a Y group, an alkyl, or a carrier;

Y is a covalent bond to Carrier, a linker that can be attached to Carrier or an antigen that can bind to an antibody Carrier;

R$_9$ is moiety of following structure:

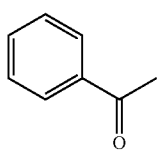 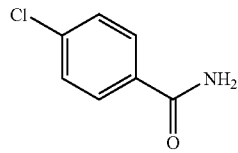

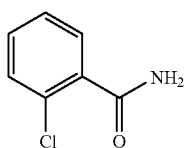 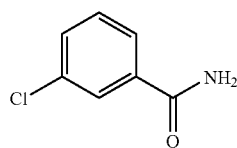

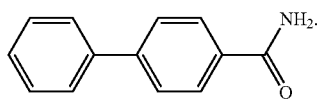

22. A multivalent complex consisting of a Carrier to which 5 to 500 compounds are attached, each compound consisting of a compound of claim 1.

23. An article comprising a solid support and a compound of claim 1.

24. The article of claim 23, wherein the solid support is a magnetic bead, a chromatographic matrix, a microtiter dish or a substrate for an array of ligands.

25. A method of isolating a cell that expresses a Siglec comprising: (a) contacting a mixture of cells that may express a Siglec with the article of claim 23; (b) washing the article; and (c) eluting cells from the article.

26. The method of claim 25, wherein the cell is a B cell.

27. The method of claim 25, wherein the cell is a leukemia cell or a lymphoma cell.

28. The method of claim 25, wherein the cell is an eosinophil.

29. The method of claim 25, wherein the mixture of cells is a test sample.

30. The method of claim 29, wherein the test sample is a blood sample from a patient suspected of having a B cell disorder.

31. The method of claim 29, wherein the test sample is a pulmonary exudate, lymph sample or blood sample from a patient suspected of having an eosinophil-related disease or condition.

32. A composition comprising a pharmaceutically acceptable carrier and a therapeutically effective amount of a compound of claim 1 or the multivalent complex of claim 22.

33. The composition of claim 32, wherein the compound or complex is covalently or non-covalently linked to a therapeutic agent.

34. The composition of claim 33, wherein the therapeutic agent is an anti-tumor agent, an antigen or an antibody.

35. A method for intracellular delivery of an agent into a cell, comprising contacting the cell with a compound of claim 1 or the multivalent complex of claim 22, wherein the cell expresses a Siglec and the compound is directly or indirectly linked to the agent.

36. The method of claim 35, wherein the Siglec is CD22, Siglec-8, CD33 or myelin associated glycoprotein.

37. The method of claim 35, wherein the cell is a B cell.

38. The method of claim 35, wherein the cell is a leukemia cell or a lymphoma cell.

39. The method of claim 35, wherein the cell is an eosinophil.

40. The method of claim 35, wherein the agent is an anti-tumor agent.

41. The method of claim 35, wherein the agent is an antibody.

42. The method of claim 35, wherein the agent is linked to the compound by a liposome carrier in which the agent is encapsulated and to which the compound is attached.

43. The method of claim 35 wherein the cell expresses CD22 and the Siglec ligand is a compound selected from the group consisting of:

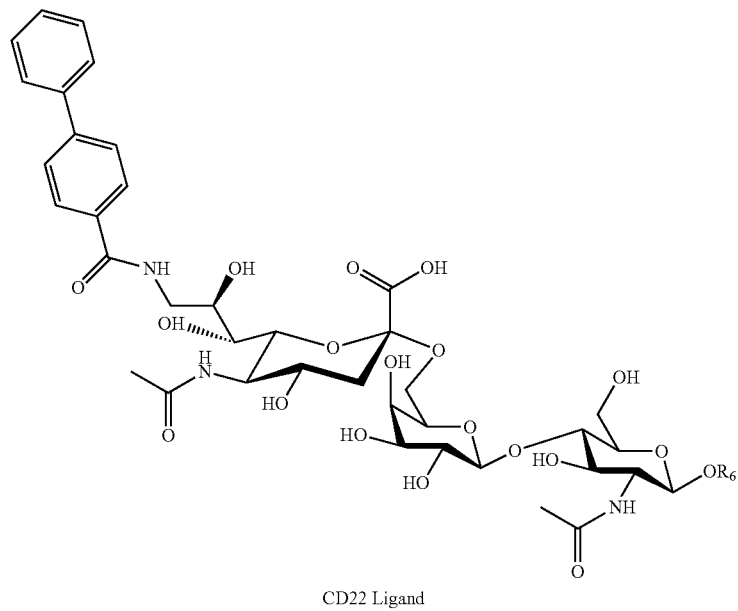
CD22 Ligand
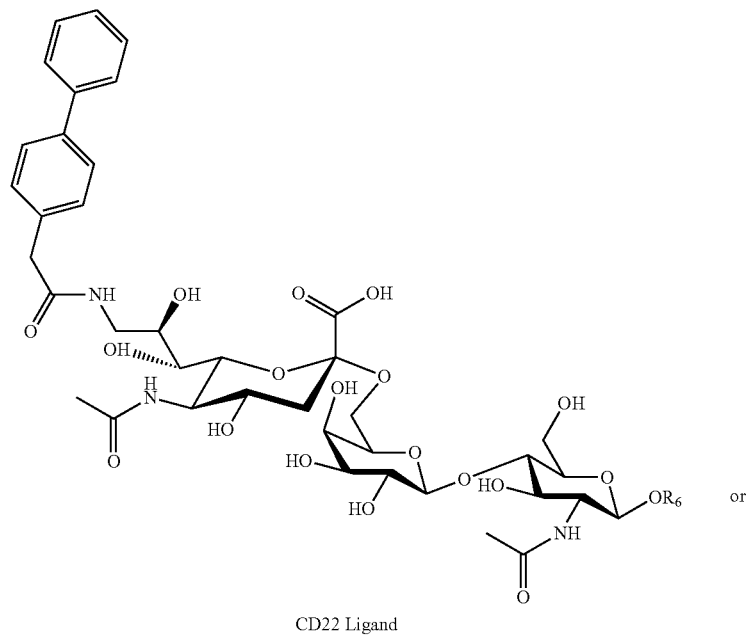
CD22 Ligand or

-continued
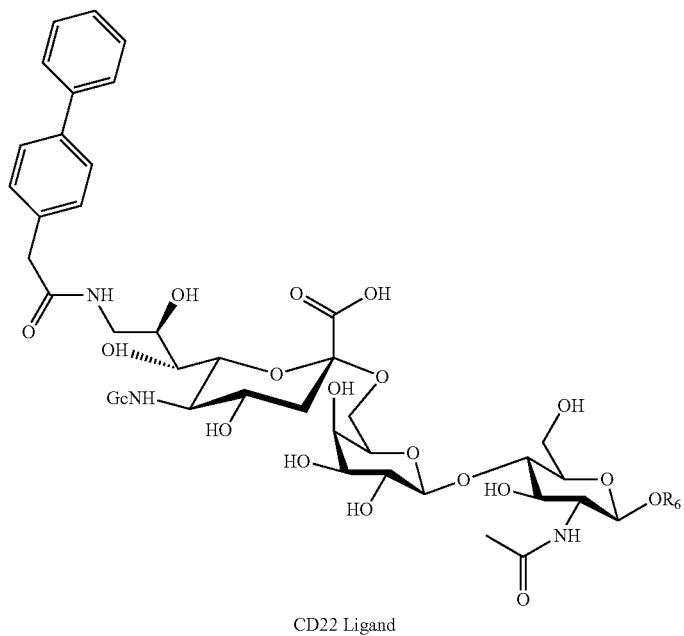
CD22 Ligand
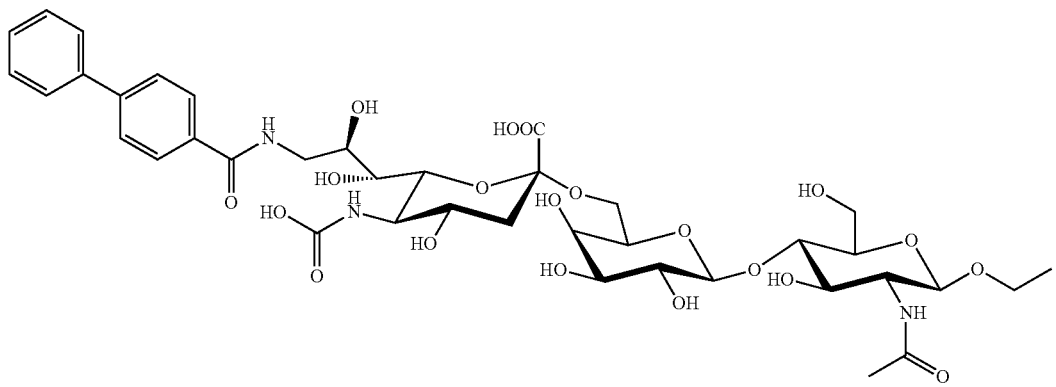
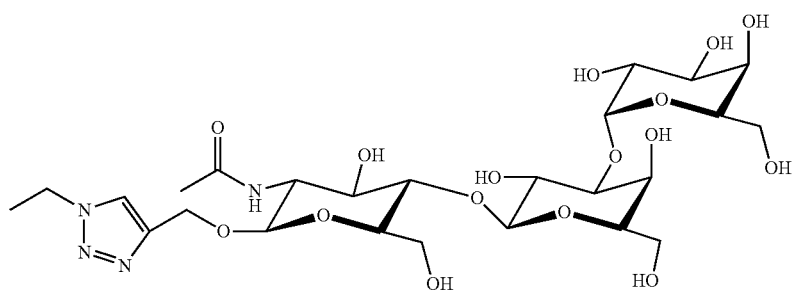
CD22 ligand wherein R₆ is a carrier to which at least five of the Siglec ligands and at least one molecule of the agent are covalently or non-covalently attached.

44. The method of cell 35, wherein the cell expresses Siglec-8 and the Siglec ligand compound has the following formula:

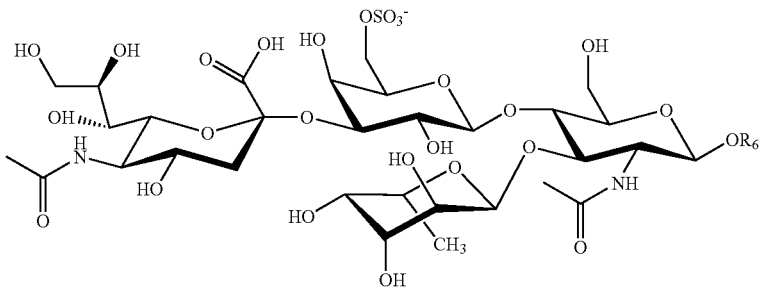

Siglec-8 Ligand wherein R₆ is a carrier to which at least five Siglec ligands and at least one molecule of the agent are covalently or non-covalently attached.

45. The method of claim 44, wherein the cell is an eosinophil.

46. A method of treating cancer in a mammal comprising administering to the mammal an effective amount of a compound of claim 1, or the multivalent complex of claim 22, wherein the compound is linked to an anti-tumor agent.

47. The method of claim 46, wherein the cancer is a lymphoma or leukemia.

48. A method for killing a B cell that expresses CD22 comprising administering to the B cell a Siglec ligand compound and exposing the cell to complement factors, wherein the Siglec ligand compound is selected from the group consisting of:

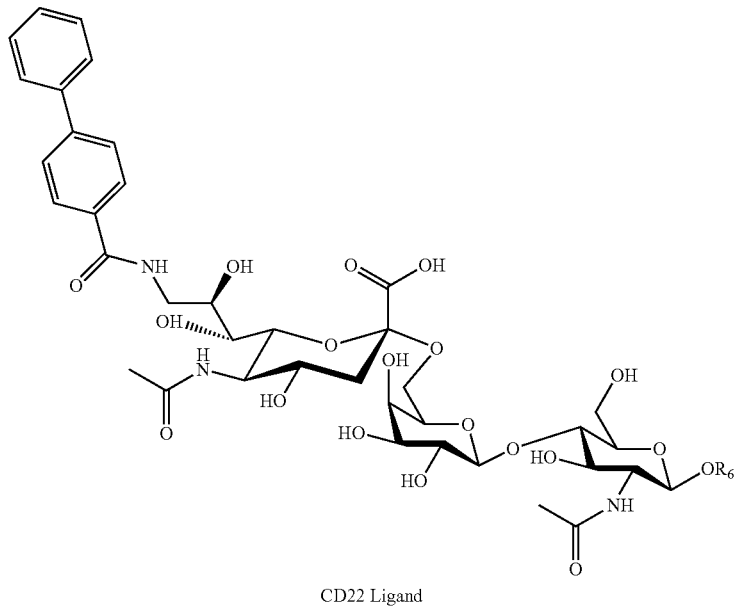

CD22 Ligand

-continued
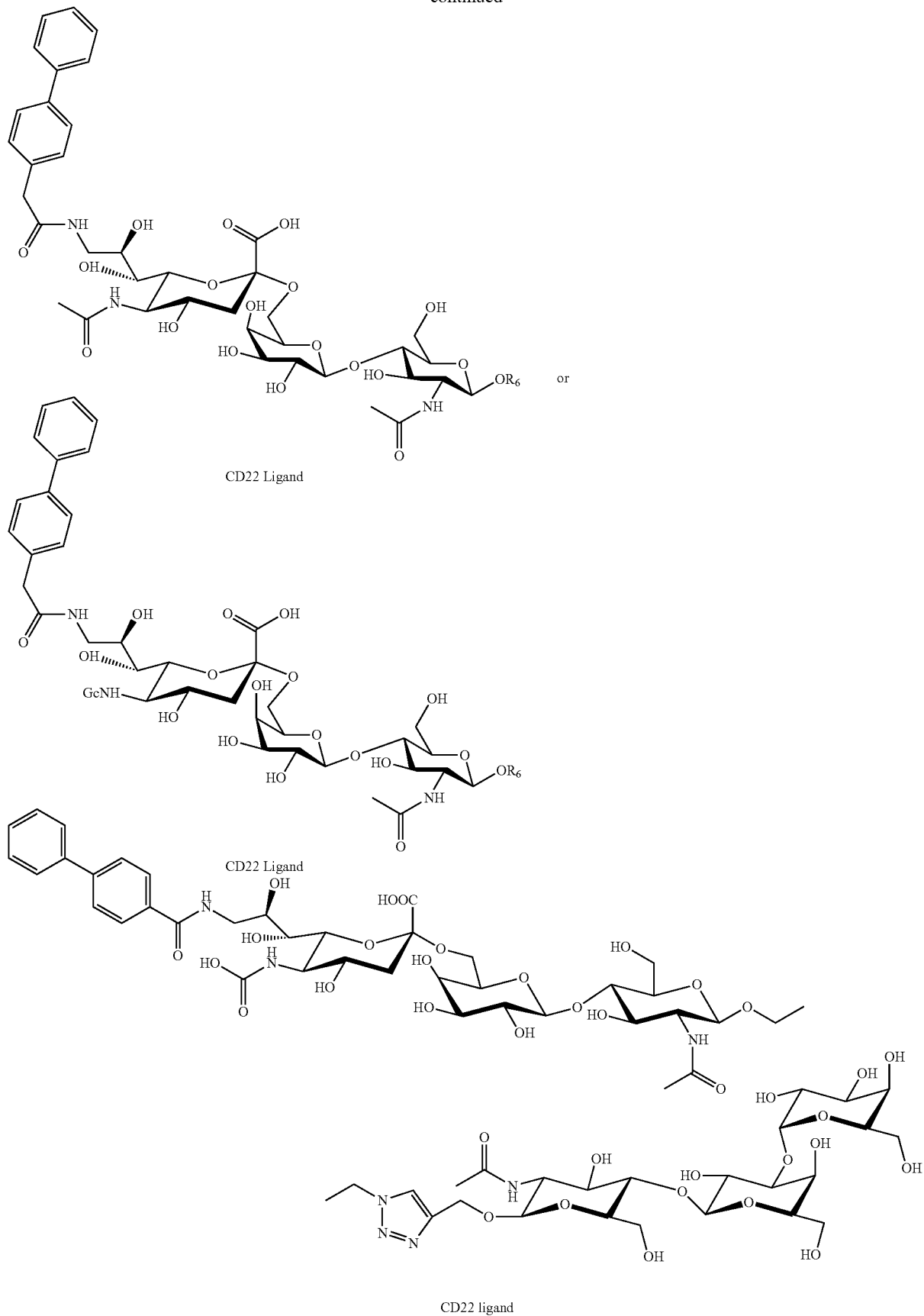
CD22 Ligand
CD22 Ligand
CD22 ligand wherein $R_6$ is a carrier and the carrier is an antigen that binds to an antibody; and the antibody that binds the antigen is bound to the antigen before or after administering the Siglec ligand to the B cell.

49. A method of treating an eosinophil-related disease or condition in a mammal comprising administering to the mammal an effective amount of a compound of the formula:

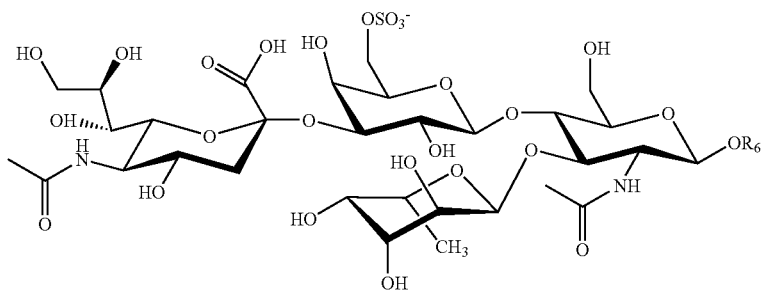

Siglec-8 Ligand wherein $R_6$ is a carrier, or a linker to which the carrier can be attached; and
wherein the carrier further comprises a therapeutic agent.

50. The method of claim 49, wherein the disease or condition is asthma, rhinitis or eczema.

51. A multivalent Carrier-Siglec ligand complex comprising a Siglec ligand, a neutral saccharide and a multivalent Carrier, wherein the Siglec ligand is a compound of formula IIa or IIb:

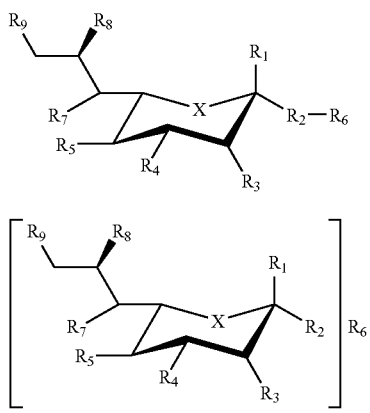

wherein:

X is a methylene or a heteroatom;

$R_1$ is a carboxylate, carboxy, phosphate or sulfate;

$R_2$ is a neutral saccharide;

$R_3$, $R_4$, $R_7$ and $R_8$ are each independently a hydrogen, a hydroxyl or a acetylamine;

$R_5$ is a hydrogen, hydroxyl, acetylamine, alkyl, alkylamide, cycloalkyl, heteroalkyl, cycloheteroalkyl, aryl, arylalkyl, arylamide or heteroaryl group that can be substituted with one to five alkyl, halo, or sulfate group;

$R_6$ is a Y group or a Carrier; and $R_9$ is an acetylamine, alkyl, alkylamide, cycloalkyl, heteroalkyl, cycloheteroalkyl, aryl, arylalkyl, arylamide or heteroaryl group that can be substituted with one to five alkyl, halo, sulfate or hydroxy groups; and Y is a linker attached to a Carrier or an antigen that can bind to an antibody Carrier.

52. The multivalent complex of claim 51, wherein the Carrier is a polymer, protein, antibody, antigen, multi-subunit protein, protein complex, glycan, lipid, liposome, nucleic acid, polysaccharide, glycoprotein, glycolipid, lipoprotein, bead or solid support.

* * * * *

UNITED STATES PATENT AND TRADEMARK OFFICE
CERTIFICATE OF CORRECTION

| | | |
|---|---|---|
| PATENT NO. | : 8,357,671 B2 | Page 1 of 1 |
| APPLICATION NO. | : 12/084723 | |
| DATED | : January 22, 2013 | |
| INVENTOR(S) | : Paulson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1226 days.

*In The Claims*

In column 67, line 31, in Claim 1, delete "R5" and insert --$R_5$--, therefor

In column 67, line 32, in Claim 1, delete "R9" and insert --$R_9$--, therefor

In column 68, line 63, in Claim 14, after "and", insert --¶--, therefor

In column 69, line 12, in Claim 19, delete "IIa" and insert --IIIa--, therefor

In column 79, line 4, in Claim 44, delete "cell" and insert --claim--, therefor

In column 83, line 2, in Claim 48, after "and", insert --¶--, therefor

Signed and Sealed this
Twenty-third Day of December, 2014

Michelle K. Lee
*Deputy Director of the United States Patent and Trademark Office*